United States Patent
McKearn et al.

(12) 
(10) Patent No.: US 6,916,800 B2
(45) Date of Patent: Jul. 12, 2005

(54) COMBINATION THERAPY INCLUDING A MATRIX METALLOPROTEINASE INHIBITOR AND AN ANTINEOPLASTIC AGENT

(75) Inventors: John P. McKearn, Glencoe, MO (US); Gary Gordon, Highland, IL (US); James J. Cunningham, Chicago, IL (US); Stephen T. Gately, Palatine, IL (US); Alane T. Koki, Beaufort, MO (US); Jaime L. Masferrer, Ballwin, MO (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/945,002

(22) Filed: Sep. 20, 2004

(65) Prior Publication Data

US 2005/0058725 A1 Mar. 17, 2005

Related U.S. Application Data

(63) Continuation of application No. 09/857,995, filed as application No. PCT/US99/30699 on Dec. 22, 1999, now Pat. No. 6,858,598.
(60) Provisional application No. 60/113,786, filed on Dec. 23, 1998.

(51) Int. Cl.$^7$ ...................... A61K 31/33; A61K 31/445; C07D 295/00; C07D 211/00; C07D 417/00
(52) U.S. Cl. ................. 514/183; 514/227.5; 514/227.8; 514/283; 514/318; 514/319; 514/321; 514/330; 544/59; 544/60; 546/48; 546/238; 546/263
(58) Field of Search ................................ 514/183, 283, 514/227.5, 319, 227.8, 321; 546/48.238, 236; 544/59, 60

(56) References Cited

PUBLICATIONS

Che,ical abstract 128:12465, also cited as Relias et al in J. Oncology Pharm. Practice 3–4, 173–185(1997).*

\* cited by examiner

*Primary Examiner*—Richard L. Raymond
*Assistant Examiner*—Sudhaker B. Patel
(74) *Attorney, Agent, or Firm*—Peter C. Richardson; Christian M. Smolizza; Garth Butterfield

(57) ABSTRACT

The present invention provides methods to treat or prevent neoplasia disorders in a mammal using a combination of a matrix metalloproteinase inhibitor and an antineoplastic agent.

14 Claims, No Drawings

COMBINATION THERAPY INCLUDING A MATRIX METALLOPROTEINASE INHIBITOR AND AN ANTINEOPLASTIC AGENT

This application is a continuation of application Ser. No. 09/857,995 filed on Oct. 5, 2001 now U.S. Pat. No. 6,858, 598, which is the national stage of International Application No. PCT/US99/30699 filed on Dec. 22, 1999, which claims priority of U.S. provisional application Ser. No. 60/113,786 filed on Dec. 23, 1998.

FIELD OF THE INVENTION

The present invention relates to combinations and methods for treatment or prevention of neoplasia disorders in a mammal using two or more components with at least one component being a matrix metalloproteinase inhibitor.

BACKGROUND OF THE INVENTION

A neoplasm, or tumor, is an abnormal, unregulated, and disorganized proliferation of cell growth. A neoplasm is malignant, or cancerous, if it has properties of destructive growth, invasiveness and metastasis. Invasiveness refers to the local spread of a neoplasm by infiltration or destruction of surrounding tissue, typically breaking through the basal laminas that define the boundaries of the tissues, thereby often entering the body's circulatory system. Metastasis typically refers to the dissemination of tumor cells by lymphotics or blood vessels. Metastasis also refers to the migration of tumor cells by direct extension through serous cavities, or subarachnoid or other spaces. Through the process of metastasis, tumor cell migration to other areas of the body establishes neoplasms in areas away from the site of initial appearance.

Cancer is now the second leading cause of death in the United States and over 8,000,000 persons in the United States have been diagnosed with cancer. In 1995, cancer accounted for 23.3% of all deaths in the United States. (See U.S. Dept. of Health and Human Services, National Center for Health Statistics, Health United States 1996–97 and Injury Chartbook 117 (1997)).

Cancer is not fully understood on the molecular level. It is known that exposure of a cell to a carcinogen such as certain viruses, certain chemicals, or radiation, leads to DNA alteration that inactivates a "suppressive" gene or activates an "oncogene". Suppressive genes are growth regulatory genes, which upon mutation, can no longer control cell growth. Oncogenes are initially normal genes (called prooncogenes) that by mutation or altered context of expression become transforming genes. The products of transforming genes cause inappropriate cell growth. More than twenty different normal cellular genes can become oncogenes by genetic alteration. Transformed cells differ from normal cells in many ways, including cell morphology, cell-to-cell interactions, membrane content, cytoskeletal structure, protein secretion, gene expression and mortality (transformed cells can grow indefinitely).

Cancer is now primarily treated with one or a combination of three types of therapies: surgery, radiation, and chemotherapy. Surgery involves the bulk removal of diseased tissue. While surgery is sometimes effective in removing tumors located at certain sites, for example, in the breast, colon, and skin, it cannot be used in the treatment of tumors located in other areas, such as the backbone, nor in the treatment of disseminated neoplastic conditions such as leukemia.

Chemotherapy involves the disruption of cell replication or cell metabolism. It is used most often in the treatment of breast, lung, and testicular cancer.

The adverse effects of systemic chemotherapy used in the treatment of neoplastic disease is most feared by patients undergoing treatment for cancer. Of these adverse effects nausea and vomiting are the most common and severe side effects. Other adverse side effects include cytopenia, infection, cachexia, mucositis in patients receiving high doses of chemotherapy with bone marrow rescue or radiation therapy; alopecia (hair loss); cutaneous complications (see M. D. Abeloff, et al: Alopecia and Cutaneous Complications. P. 755–56. In Abeloff, M. D., Armitage, J. O., Lichter, A. S., and Niederhuber, J. E. (eds) Clinical Oncology. Churchill Livingston, New York, 1992, for cutaneous reactions to chemotherapy agents), such as pruritis, urticaria, and angioedema; neurological complications; pulmonary and cardiac complications in patients receiving radiation or chemotherapy; and reproductive and endocrine complications.

Chemotherapy-induced side effects significantly impact the quality of life of the patient and may dramatically influence patient compliance with treatment.

Additionally, adverse side effects associated with chemotherapeutic agents are generally the major dose-limiting toxicity (DLT) in the administration of these drugs. For example, mucositis, is one of the major dose limiting toxicity for several anticancer agents, including the antimetabolite cytotoxic agents 5-FU, methotrexate, and antitumor antibiotics, such as doxorubicin. Many of these chemotherapy-induced side effects if severe, may lead to hospitalization, or require treatment with analgesics for the treatment of pain.

The adverse side effects induced by chemotherapeutic agents and radiation therapy have become of major importance to the clinical management of cancer patients.

The use of TNP-470 and minocycline in combination with cyclophasphamide, CDDP, or thiotepa have been observed to substantially increase the tumor growth delay in one pre-clinical solid tumor model. (Teicher, B. A. et al., Breast Cancer Research and Treatment, 36: 227–236, 1995). Additionally, improved results were observed when TNP-470 and minocycline were used in combination with cyclophosphamide and fractionated radiation therapy. (Teicher, B. A. et al., European Journal of Cancer 32A (14): 2461–2466, 1996). Neri et al. examined the use of AG-3340 in combination with carboplatin and taxol for the treatment of cancer. (Neri et al., Proc Am Assoc Can Res, Vol 39, 89 meeting, 302 1998). U.S. Pat. No. 5,837,696 describes the use of tetracycline compounds to inhibit cancer growth. WO 97/48, 685 describes various substituted compounds that inhibit metalloproteases. EP 48/9,577 describes peptidyl derivatives used to prevent tumor cell metastasis and invasion. WO 98/25,949 describes the use of N5-substituted 5-amino-1,3, 4-thiadiazole-2-thiols to inhibit metallopreteinase enzymes. WO 99/21,583 describes a method of inhibiting metastases in patients having cancer in which wildtype p53 is predominantly expressed using a combination of radiation therapy and a selective matrix metalloproteinase-2 inhibitor. WO 98/33,768 describes arylsulfonylamino hydroxamic acid-derivatives in the treatment of cancer. WO 98/30,566 describes cyclic sulfone derivatives useful in the treatment of cancer. WO 98/34,981 describes arylsulfonyl hydroxamic acid derivatives useful in the treatment of cancer. WO 98/33,788 discloses the use of carboxylic or hyroxamic acid derivatives for treatment of tumors. WO 97/41,844 describes a method of using combinations of angiostatic compounds for the prevention and/or treatment of neovascularization in human patients. EP 48/9,579 describes peptidyl derivatives with selective gelatinase action that may be of use in the treatment of cancer and to control tumor metastases. WO 98/11,908 describes the use of carboxylic or hyroxamic acid derivatives and a cyclosporin in combination therapy for treating mammals suffering from arthritic disease. WO 98/03,516 describes phasphinate based compounds useful in the treatment of cancer. WO 95/23,811 describes novel carbocyclic compounds which inhibit platelet aggregation. Wo 93/24,475 describes sulphamide derivatives may be useful in the treatment of cancer to control the development of metastases. WO 98/16,227 describes a method of using [Pyrozol-1-yl]benzenesulfonamides in the treatment of and prevention of neoplasia. WO 98/22,101 describes a method of using [Pyrozol-1-yl]benzenesulfonamides as anti-angiogenic agents. U.S. Pat. No. 5,854,205 describes an isolated endostatin protein that is an inhibitor of endothelial cell proliferation and angiogenesis. U.S. Pat. No. 5,843,925 describes a method for inhibiting angiogenesis and endothelial cell proliferation using a 7-[substituted amino]-9-[(substituted glycyloamido]-6-demethyl-6-deoxytetracycline. U.S. Pat. No. 5,863,538 describes methods and compositions for targeting tumor vasculature of solid tumors using immunological and growth factor-based reagents in combination with chemotherapy and radiation. U.S. Pat. No. 5,837,682 describes the use of fragments of an endothelial cell proliferation inhibitor, angiostatin. U.S. Pat. No. 5,861,372 describes the use of an aggregate endothelial inhibitor, angiostatin, and it use in inhibiting angiogenesis. U.S. Pat. No. 5,885,795 describes methods and compositions for treating diseases mediated by undesired and uncontrolled angiogenesis by administering purified angiostatin or angiostatin derivatives. PCT/GB97/00650 describes the use of cinnoline derivatives for use in the production of an antiangiogenic and/or vascular permeability reducing effect. PCT/US97/09610 describes administration of an anti-endogin monoclonal antibody, or fragments thereof, which is conjugated to at least one angiogenesis inhibitor or antitumor agent for use in treating tumor and angiogenesis-associated diseases. PCT/IL96/00012 describes a fragment of the Thrombin B-chain for the treatment of cancer. PCT/US95/16855 describes compositions and methods of killing selected tumor cells using recombinant viral vectors. Ravaud, A. et al. describes the efficacy and tolerance of interleukin-2 (IL-2), interferon alpha-2a, and fluorouracil in patients with metastatic renal cell carcinoma. J.Clin.Oncol. 16, No. 8, 2728–32, 1998. Stadler, W. M. et al. describes the response rate and toxicity of oral 13-cis-retinoic acid added to an outpatient regimen of subcutaneous interleukin-2 and interferon alpha in patients with metastatic renal cell carcinoma. J.Clin.Oncol. 16, No. 5, 1820–25, 1998 Rosenbeg, S. A. et al. describes treatment of patients with metastatic melanoma using chemotherapy with cisplatin, dacarbazine, and tamoxifen alone or in combination with interleukin-2 and interferon alpha-2b. J.Clin.Oncol. 17, No. 3, 968–75, 1999. Tourani, J-M. et al describes treatment of renal cell carcinoma using interleukin-2, and interferon alpha-2a administered in combination with fluorouracil. J.Clin.Oncol. 16, No. 7, 2505–13, 1998. Majewski, S. describes the anticancer action of retinoids, vitamin D3 and cytokines (interferons and interleukin-12) as related to the antiangiogenic and antiproliferative effects. J.Invest.Dermatol. 108, No. 4, 571, 1997. Ryan, C. W. describes treatment of patients with metastatic renal cell cancer with GM-CSF, Interleukin-2, and interferon-alpha plus oral cis-retinoic acid in patients with metastatic renal cell cancer. J.Invest.Med. 46, No. 7, 274A, 1998. Tai-Ping, D. describes potential anti-angiogenic therapies. Trends Pharmacol.Sci. 16, No. 2, 57–66, 1995. Brembeck, F. H. describes the use of 13-cis retinoic acid and interferon alpha to treat UICC stage III/IV pancreatic cancer. Gastroenterology 114, No. 4, Pt. 2, A569, 1998. Brembeck, F. H. describes the use of 13-cis retinoic acid and interferon alpha in patients with advanced pancreatic carcinoma. Cancer 83, No. 11, 2317–23, 1998. Mackean, M. J. describes the use of roquinimex (Linomide) and alpha interferon in patients with advanced malignant melanoma or renal carcinoma. Br.J.Cancer 78, No. 12, 1620–23, 1998 Jayson, G. C. describes the use of interleukin 2 and interleukin-interferon alpha in advanced renal cancer. Br.J.Cancer 78, No. 3, 366–69, 1998. Abraham, J. M. describes the use of Interleukin-2, interferon alpha and 5-fluorouracil in patients with metastatic renal carcinoma. Br.J.Cancer 78, Suppl. 2, 8, 1998. Soori, G. S. describes the use of chemo-biotherapy with chlorambucil and alpha interferon in patients with non-hodgkins lymphoma. Blood 92, No. 10, Pt. 2 Suppl. 1, 240b, 1998. Enschede, S. H. describes the use of interferon alpha added to an anthracycline-based regimen in treating low grade and intermediate grade non-hodgkin's lymphoma. Blood 92, No. 10, Pt. 1 Suppl. 1, 412a, 1998. Schachter, J. describes the use of a sequential multi-drug chemotherapy and biotherapy with interferon alpha, a four drug chemotherapy regimen and GM-CSF. Cancer Biother.Radiopharm. 13, No. 3, 155–64, 1998. Mross, K. describes the use of retinoic acid, interferon alpha and tamoxifen in metastatic breast cancer patients. J.Cancer Res. Clin. Oncology. 124 Suppl. 1 R123, 1998. Muller, H. describes the use of suramin and tamoxifen in the treatment of advanced and metastatic pancreatic carcinoma. Eur.J.Cancer 33, Suppl. 8, S50, 1997. Rodriguez, M. R. describes the use of taxol and cisplatin, and taxotere and vinorelbine in the treatment of metastatic breast cancer. Eur.J.Cancer 34, Suppl. 4, S17–S18, 1998. Formenti, C. describes concurrent paclitaxel and radiation therapy in locally advanced breast cancer patients. Eur.J.Cancer 34, Suppl. 5, S39, 1998. Durando, A. describes combination chemotherapy with paclitaxel (T) and epirubicin (E) for metastatic breast cancer. Eur.J.Cancer 34, Suppl. 5, S41, 1998. Osaki, A. describes the use of a combination therapy with mitomycin-C, etoposide, doxifluridine and medroxyprogesterone acetate as second-line therapy for advanced breast cancer. Eur.J.Cancer 34, Suppl. 5, S59, 1998.

DESCRIPTION OF THE INVENTION

Treatment or prevention of a neoplasia disorder in a mammal in need of such treatment or prevention is provided by methods and combinations using two or more components with at least one component being a matrix metalloproteinase (MMP) inhibitor.

The method comprises treating said mammal with a therapeutically effective amount of a combination comprising a combination of two or more agents. The first agent is a matrix metalloproteinase inhibitor (MMP), and the additional component or components is optionally selected from (a) an antiangiogenesis agent; (b) an antineoplastic agent; (c) an adjunctive agent; (d) an immunotherapeutic agent; (e) a device; (f) a vaccine; (g) an analgesic agent; and (h) a radiotherapeutic agent; provided that the additional component(s) is other than the cycloxygenase-2 inhibitor selected as the first component and the matrix metalloproteinase inhibitor selected as the second component.

In one embodiment the combination comprises a matrix metalloproteinase inhibitor and an antineoplastic agent.

Besides being useful for human treatment, the present invention is also useful for veterinary treatment of companion animals, exotic animals and farm animals, including mammals, rodents, and the like. More preferred animals include horses, dogs, and cats.

The methods and combinations of the present invention may be used for the treatment or prevention of neoplasia disorders including acral lentiginous melanoma, actinic keratoses, adenocarcinoma, adenoid cycstic carcinoma, adenomas, adenosarcoma, adenosquamous carcinoma, astrocytic tumors, bartholin gland carcinoma, basal cell carcinoma, bronchial gland carcinomas, capillary, carcinoids, carcinoma, carcinosarcoma, cavernous, cholangiocarcinoma, chondosarcoma, choriod plexus papilloma/carcinoma, clear cell carcinoma, cystadenoma, endodermal sinus tumor, endometrial hyperplasia, endometrial stromal sarcoma, endometrioid adenocarcinoma, ependymal, epitheloid, Ewing's sarcoma, fibrolamellar, focal nodular hyperplasia, gastrinoma, germ cell tumors, glioblastoma, glucagonoma, hemangiblastomas, hemangioendothelioma, hemangiomas, hepatic adenoma, hepatic adenomatosis, hepatocellular carcinoma, insulinoma, intaepithelial neoplasia, interepithelial squamous cell neoplasia, invasive squamous cell carcinoma, large cell carcinoma, leiomyosarcoma, lentigo maligna melanomas, malignant melanoma, malignant mesothelial tumors, medulloblastoma, medulloepithelioma, melanoma, meningeal, mesothelial, metastatic carcinoma, mucoepidermoid carcinoma, neuroblastoma, neuroepithelial adenocarcinoma nodular melanoma, oat cell carcinoma, oligodendroglial, osteosarcoma, pancreatic polypeptide, papillary serous adenocarcinoma, pineal cell, pituitary tumors, plasmacytoma, pseudosarcoma, pulmonary blastoma, renal cell carcinoma, retinoblastoma, rhabdomyosarcoma, sarcoma, serous carcinoma, small cell carcinoma, soft tissue carcinomas, somatostatin-secreting tumor, squamous carcinoma, squamous cell carcinoma, submesothelial, superficial spreading melanoma, undifferentiatied carcinoma, uveal melanoma, verrucous carcinoma, vipoma, well differentiated carcinoma, and Wilm's tumor.

The methods and combinations of the present invention provide one or more benefits. Combinations of MMP inhibitors with the compounds, combinations, agents and therapies of the present invention are useful in treating and preventing neoplasia disorders. Preferably, the MMP inhibitor or inhibitors and the compounds, combinations, agents and therapies of the present invention are administered in combination at a low dose, that is, at a dose lower than has been conventionally used in clinical situations.

A benefit of lowering the dose of the compounds, combinations, agents and therapies of the present invention administered to a mammal includes a decrease in the incidence of adverse effects associated with higher dosages. For example, by the lowering the dosage of a chemotherapeutic agent such as methotrexate, a reduction in the frequency and the severity of nausea and vomiting will result when compared to that observed at higher dosages. Similar benefits are contemplated for the compounds, compositions, agents and therapies in combination with the MMP inhibitors of the present invention.

By lowering the incidence of adverse effects, an improvement in the quality of life of a patient undergoing treatment for cancer is contemplated. Further benefits of lowering the incidence of adverse effects include an improvement in patient compliance, a reduction in the number of hospitalizations needed for the treatment of adverse effects, and a reduction in the administration of analgesic agents needed to treat pain associated with the adverse effects.

Alternatively, the methods and combination of the present invention can also maximize the therapeutic effect at higher doses.

When administered as a combination, the therapeutic agents can be formulated as separate compositions which are given at the same time or different times, or the therapeutic agents can be given as a single composition.

When used as a therapeutic the compounds described herein are preferably administered with a physiologically acceptable carrier. A physiologically acceptable carrier is a formulation to which the compound can be added to dissolve it or otherwise facilitate its administration. Examples of physiologically acceptable carriers include, but are not limited to, water, saline, physiologically buffered saline. Additional examples are provided below.

The term "pharmaceutically acceptable" is used adjectivally herein to mean that the modified noun is appropriate for use in a pharmaceutical product. Pharmaceutically acceptable cations include metallic ions and organic ions. More preferred metallic ions include, but are not limited to appropriate alkali metal salts, alkaline earth metal salts and other physiological acceptable metal ions. Exemplary ions include aluminum, calcium, lithium, magnesium, potassium, sodium and zinc in their usual valences. Preferred organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine (N-methylglucamine) and procaine. Exemplary pharmaceutically acceptable acids include without limitation hydrochloric acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid oxalacetic acid, fumaric acid, propionic acid, aspartic acid, glutamic acid, benzoic acid, and the like.

A compound of the present invention can be formulated as a pharmaceutical composition. Such a composition can then be administered orally, parenterally, by inhalation spray, rectally, or topically in dosage unit formulations containing conventional nontoxic pharmaceutically acceptable carriers, adjuvants, and vehicles as desired. Topical administration can also involve the use of transdermal administration such,as transdermal patches or iontophoresis devices. The term parenteral as used herein includes subcutaneous injections, intravenous, intramuscular, intrasternal injection, or infusion techniques. Formulation of drugs is discussed in, for example, Hoover, John E., *Remington's Pharmaceutical Sciences*, Mack Publishing Co., Easton, Pa.; 1975. Other examples of drug formulations can be found in Liberman, H. A. and Lachman, L., Eds., *Pharmaceutical Dosage Forms*, Marcel Decker, New York, N.Y., 1980.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

Dimethyl acetamide, surfactants including ionic and nonionic detergents, polyethylene glycols can be used. Mixtures of solvents and wetting agents such as those discussed above are also useful.

Suppositories for rectal administration of the drug can be prepared by mixing the drug with a suitable nonirritating excipient such as cocoa butter, synthetic mono- di- or triglycerides, fatty acids and polyethylene glycols that are sold at ordinary temperatures but liquid at the rectal temperature and will therefore melt in the rectum and release the drug.

Solid dosage forms for oral administration can include capsules, tablets, pills, powders, and granules. In such solid dosage forms, the compounds of this invention are ordinarily combined with one or more adjuvants appropriate to the indicated route of administration. If administered per os, a contemplated aromatic sulfone hydroximate inhibitor compound can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. A contemplated aromatic sulfone hydroximate inhibitor compound can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredient that can be combined with the carrier materials to produce a single dosage form varies depending upon the mammalian host treated and the particular mode of administration.

The present invention further includes kits comprising a MMP inhibitor and an antineoplastic agent.

The term "treatment" refers to any process, action, application, therapy, or the like, wherein a mammal, including a human being, is subject to medical aid with the object of improving the mammal's condition, directly or indirectly.

The term "inhibition," in the context of neoplasia, tumor growth or tumor cell growth, may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, is referred to herein as prevention or chemoprevention.

The term "prevention" includes either preventing the onset of clinically evident neoplasia altogether or preventing the onset of a preclinically evident stage of neoplasia in individuals at risk. Also intended to be encompassed by this definition is the prevention of initiation for malignant cells or to arrest or reverse the progression of premalignant cells to malignant cells. This includes prophylactic treatment of those at risk of developing the neoplasia.

The term "angiogenesis" refers to the process by which tumor cells trigger abnormal blood vessel growth to create their own blood supply, and is a major target of cancer research. Angiogenesis is believed to be the mechanism via which tumors get needed nutrients to grow and metastasize to other locations in the body. Antiangiogenic agents interfere with these processes and destroy or control tumors.

Angiogenesis is an attractive therapeutic target because it is a multi-step process that occurs in a specific sequence, thus providing several possible targets for drug action. Examples of agents that interfere with several of these steps include thrombospondin-1, angiostatin, endostatin, interferon alpha and compounds such as matrix metalloproteinase (MMP) inhibitors that block the actions of enzymes that clear and create paths for newly forming blood vessels to follow; compounds, such as $\alpha v\beta 3$ inhibitors, that interfere with molecules that blood vessel cells use to bridge between a parent blood vessel and a tumor; agents, such as specific COX-2 inhibitors, that prevent the growth of cells that form new blood vessels; and protein-based compounds that simultaneously interfere with several of these targets.

Antiangiogenic therapy may offer several advantages over conventional chemotherapy for the treatment of cancer. Antiangiogenic agents have low toxicity in preclinical trials and development of drug resistance has not been observed (Folkman, J., *Seminars in Medicine of the Beth Israel Hospital, Boston* 333(26): 1757–1763, 1995). As angiogenesis is a complex process, made up of many steps including invasion, proliferation and migration of endothelial cells, it can be anticipated that combination therapies will be most effective. Kumar and Armstrong describe anti-angiogenesis therapy used as an adjunct to chemotherapy, radiation therapy, or surgery. (Kumar, C C, and Armstrong, L., Tumor-induced angiogenesis: a novel target for drug therapy?, Emerging Drugs (1997), 2, 175–190).

The phrase "therapeutically-effective" is intended to qualify the amount of each agent that will achieve the goal of improvement in neoplastic disease severity and the frequency of neoplastic disease over treatment of each agent by itself, while avoiding adverse side effects typically associated with alternative therapies.

A "therapeutic effect" or "therapeutic effective amount" is intended to qualify the amount of an anticancer agent required to relieve to some extent one or more of the symptoms of a neoplasia disorder, including, but is not limited to: 1) reduction in the number of cancer cells; 2) reduction in tumor size; 3) inhibition (i.e., slowing to some extent, preferably stopping) of cancer cell infiltration into peripheral organs; 3) inhibition (i.e., slowing to some extent, preferably stopping) of tumor metastasis; 4) inhibition, to some extent, of tumor growth; 5) relieving or reducing to some extent one or more of the symptoms associated with the disorder; and/or 6) relieving or reducing the side effects associated with the administration of anticancer agents.

The phrase "combination therapy" (or "co-therapy") embraces the administration of a metalloproteinase inhibitor, and an antineoplastic agent as part of a specific treatment regimen intended to provide a beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" generally is not intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients (such as, but not limited to, a second and different antineoplastic agent) and non-drug therapies (such as, but not limited to, surgery or radiation treatment). Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

The phrases "low dose" or "low dose amount", in characterizing a therapeutically effective amount of the antiangiogenesis agent and the antineoplastic agent or therapy in the combination therapy, defines a quantity of such agent, or a range of quantity of such agent, that is capable of improving the neoplastic disease severity while reducing or avoiding one or more antineoplastic-agent-induced side effects, such as myelosupression, cardiac toxicity, alopecia, nausea or vomiting.

The phrase "adjunctive therapy" encompasses treatment of a subject with agents that reduce or avoid side effects associated with the combination therapy of the present invention, including, but not limited to, those agents, for example, that reduce the toxic effect of anticancer drugs, e.g., bone resorption inhibitors, cardioprotective agents; prevent or reduce the incidence of nausea and vomiting associated with chemotherapy, radiotherapy or operation; or reduce the incidence of infection associated with the administration of myelosuppressive anticancer drugs.

The phrases "low dose", or "low dose amount", in characterizing a therapeutically effective amount of the antiangiogenesis agent and the antineoplastic agent or therapy in the combination therapy, defines a quantity of such agent, or a range of quantity of such agent, that is capable of improving the neoplastic disease severity while reducing or avoiding one or more antineoplastic-agent-induced side effects, such as myelosupression, cardiac toxicity, alopecia, nausea or vomiting.

The phrase "adjunctive therapy" includes agents such as those, for example, that reduce the toxic effect of anticancer drugs, e.g., bone resorption inhibitors, cardioprotective agents; prevent or reduce the incidence of nausea and vomiting associated with chemotherapy, radiotherapy or operation; or reduce the incidence of infection associated with the administration of myelosuppressive anticancer drugs.

The phrase an "immunotherapeutic agent" refers to agents used to transfer the immunity of an immune donor, e.g., another person or an animal, to a host by inoculation. The term embraces the use of serum or gamma gobulin containing performed antibodies produced by another individual or an animal; nonspecific systemic stimulation; adjuvants; active specific immunotherapy; and adoptive immunotherapy. Adoptive immunotherapy refers to the treatment of a disease by therapy or agents that include host inoculation of sensitized lymphocytes, transfer factor, immune RNA, or antibodies in serum or gamma globulin.

The phrase a "device" refers to any appliance, usually mechanical or electrical, designed to perform a particular function.

The phrase a "vaccine" includes agents that induce the patient's immune system to mount an immune response against the tumor by attacking cells that express tumor associated antigens (TAAs).

The phrase "multi-functional proteins" encompass a variety of pro-angiogenic factors that include basic and acid fibroblast growth factors (bFGF and aFGF) and vascular permeability factor/vascular endothelial growth factor (VPF/VEGF) (Bikfalvi, A. et al., *Endocrine Reviews* 18: 26–45, 1997). Several endogenous antiangiogenic factors have also been characterized as multi-functional proteins and include angiostatin (O'Reilly et al., *Cell* (Cambridge, Mass.) 79(2): 315–328, 1994), endostatin (O'Reilly et al, *Cell* (Cambridge, Mass.) 88(2): 277–285, 1997), interferon .alpha. (Ezekowitz et al, *N. Engl. J. Med.*, May 28, 326(22) 1456–1463, 1992), thrombospondin (Good et al, *Proc Natl Acad Sci USA* 87(17): 6624–6628, 1990; Tolsma et al, *J Cell Biol* 122(2): 497–511, 1993), and platelet factor 4 (PF4) (Maione et al, *Science* 247:(4938): 77–79, 1990).

The phrase an "analgesic agent" refers to an agent that relieves pain without producing anesthesia or loss of consciousness generally by altering the perception of nociceptive stimuli.

The phrase a "radiotherapeutic agent" refers to the use of electromagnetic or particulate radiation in the treatment of neoplasia.

The term "pBATT embraces" or "Protein-Based Anti-Tumor Therapies," refers to protein-based therapeutics for solid tumors. The pBATTs include proteins that have demonstrated efficacy against tumors in animal models or in humans. The protein is then modified to increase its efficacy and toxicity profile by enhancing its bioavailability and targeting.

"Angiostatin" is a 38 kD protein comprising the first three or four kringle domains of plasminogen and was first described in 1994 (O'Reilly, M. S. et al., *Cell* (Cambridge, Mass.) 79(2): 315–328, 1994). Mice bearing primary (Lewis lung carcinoma-low metastatic) tumors did not respond to angiogenic stimuli such as bFGF in a corneal micropocket assay and the growth of metastatic tumors in these mice was suppressed until the primary tumor was excised. The factor responsible for the inhibition of angiogenesis and tumor growth was designated mouse angiostatin. Angiostatin was also shown to inhibit the growth of endothelial cells in vitro.

Human angiostatin can be prepared by digestion of plasminogen by porcine elastase (O'Reilly, et al., *Cell* 79(2): 315–328, 1994) or with human metalloelastase (Dong et al., *Cell* 88, 801–810, 1997). The angiostatin produced via porcine elastase digestion inhibited the growth of metastases and primary tumors in mice. O'Reilly et al., (*Cell* 79(2): 315–328, 1994) demonstrated that human angiostatin inhibited metastasis of Lewis lung carcinoma in SCID mice. The same group (O'Reilly, M. S. et al., *Nat. Med.* (N.Y.) 2(6): 689–692, 1996) subsequently showed that human angiostatin inhibited the growth of the human tumors PC3 prostate carcinoma, clone A colon carcinoma, and MDA-MB breast carcinoma in SCID mice. Human angiostatin also inhibited the growth of the mouse tumors Lewis lung carcinoma, T241 fibrosarcoma and M5076 reticulum cell carcinoma in C57B1 mice. Because these enzymatically-prepared angiostatins are not well characterized biochemically, the precise composition of the molecules is not known.

Angiostatins of known composition can be prepared by means of recombinant DNA technology and expression in heterologous cell systems. Recombinant human angiostatin comprising Kringle domains one through four (K1–4) has been produced in the yeast *Pichia pastoris* (Sim et al., *Cancer Res* 57: 1329–1334, 1997). The recombinant human protein inhibited growth of endothelial cells in vitro and inhibited metastasis of Lewis lung carcinoma in C57Bl mice. Recombinant murine angiostatin (K1–4) has been produced in insect cells (Wu et al., *Biochem Biophys Res Comm* 236: 651–654, 1997). The recombinant mouse protein inhibited endothelial cell growth in vitro and growth of primary Lewis lung carcinoma in vivo. These experiments demonstrated that the first four kringle domains are sufficient for angiostatin activity but did not determine which kringle domains are necessary.

Cao et al. (*J. Biol. Chem.* 271: 29461–29467, 1996), produced fragments of human plasminogen by proteolysis and by expression of recombinant proteins in *E. coli*. These authors showed that kringle one and to a lesser extent kringle four of plasminogen were responsible for the inhibition of endothelial cell growth in vitro. Specifically, kringles 1–4 and 1–3 inhibited at similar concentrations, while K1 alone inhibited endothelial cell growth at four-fold higher concentrations. Kringles two and three inhibited to a lesser extent. More recently Cao et al. (*J Biol Chem* 272: 22924–22928, 1997), showed that recombinant mouse or human kringle five inhibited endothelial cell growth at lower concentrations than angiostatin (K1–4). These experiments demonstrated in vitro angiostatin-like activity but did not address in vivo action against tumors and their metastases.

PCT publication WO 95/29242 discloses purification of a protein from blood and urine by HPLC that inhibits proliferation of endothelial cells. The protein has a molecular weight between 38 kilodaltons and 45 kilodaltons and an amino acid sequence substantially similar to that of a murine plasminogen fragment beginning at amino acid number 79 of a murine plasminogen molecule. PCT publication WO 96/41194, discloses compounds and methods for the diagnosis and monitoring of angiogenesis-dependent diseases. PCT publication WO 96/35774 discloses the structure of protein fragments, generally corresponding to kringle structures occurring within angiostatin. It also discloses aggregate forms of angiostatin, which have endothelial cell inhibiting activity, and provides a means for inhibiting angiogenesis of tumors and for treating angiogenic-mediated diseases.

"Endostatin" is a 20-kDa (184 amino acid) carboxy fragment of collagen XVIII, is an angiogenesis inhibitor produced by a hemangioendothelioma (O'Reilly, M. S. et al., *Cell* (Cambridge, Mass.) 88(2): 277–285, 1997); and WO 97/15666). Endostatin specifically inhibits endothelial proliferation and inhibits angiogenesis and tumor growth. Primary tumors treated with non-refolded suspensions of *E. coli*-derived endostatin regressed to dormant microscopic lesions. Toxicity was not observed and immunohistochemical studies revealed a blockage of angiogenesis accompanied by high proliferation balanced by apoptosis in tumor cells.

"Interferon .alpha." (IFN.alpha.) is a family of highly homologous, species-specific proteins that possess complex antiviral, antineoplastic and immunomodulating activities (Extensively reviewed in the monograph "Antineoplastic agents, interferon alfa", American Society of Hospital Pharmacists, Inc., 1996). Interferon .alpha. also has antiproliferative, and antiangiogenic properties, and has specific effects on cellular differentiation (Sreevalsan, in "Biologic Therapy of Cancer", pp. 347–364, (eds. V. T. DeVita Jr., S. Hellman, and S. A. Rosenberg), J.B. Lippincott Co, Philadelphia, Pa., 1995).

Interferon .alpha. is effective against a variety of cancers including hairy cell leukemia, chronic myelogenous leukemia, malignant melanoma, and Kaposi's sarcoma. The precise mechanism by which IFN.alpha. exerts its antitumor activity is not entirely clear, and may differ based on the tumor type or stage of disease. The anti-proliferative properties of IFN.alpha., which may result from the modulation of the expression of oncogenes and/or protooncogenes, have been demonstrated on both tumor cell lines and human tumors growing in nude mice (Gutterman, J. U., *Proc. Natl. Acad. Sci., USA* 91: 1198–1205, 1994).

Interferon is also considered an anti-angiogenic factor, as demonstrated through the successful treatment of hernangiomas in infants (Ezekowitz et al, *N. Engl. J. Med.*, May 28, 326(22) 1456–1463, 1992) and the effectiveness of IFN.alpha. against Kaposi's sarcoma (Krown, *Semin Oncol* 14(2 Suppl 3): 27–33, 1987). The mechanism underlying these anti-angiogenic effects is not clear, and may be the result of IFN.alpha. action on the tumor (decreasing the secretion of pro-angiogenic factors) or on the neo-vasculature. IFN receptors have been identified on a variety of cell types (Navarro et al., *Modern Pathology* 9(2): 150–156, 1996).

U.S. Pat. No. 4,530,901, by Weissmann, describes the cloning and expression of IFN-.alpha.-type molecules in transformed host strains. U.S. Pat. No. 4,503,035, Pestka, describes an improved processes for purifying 10 species of human leukocyte interferon using preparative high performance liquid chromatography. U.S. Pat. No. 5,231,176, Goeddel, describes the cloning of a novel distinct family of human leukocyte interferons containing in their mature form greater than 166 and no more than 172 amino acids.

U.S. Pat. No. 5,541,293, by Stabinsky, describes the synthesis, cloning, and expression of consensus human interferons. These are non-naturally occurring analogues of human (leukocyte) interferon-.alpha. assembled from synthetic oligonucleotides. The sequence of the consensus interferon was determined by comparing the sequences of 13 members of the IFN-.alpha. family of interferons and selecting the preferred amino acid at each position. These variants differ from naturally occurring forms in terms of the identity and/or location of one or more amino acids, and one or more biological and pharmacological properties (e.g., antibody reactivity, potency, or duration effect) but retain other such properties.

"Thrombospondin-1" (TSP-1) is a trimer containing three copies of a 180 kDa polypeptide. TSP-1 is produced by many cell types including platelets, fibroblasts, and endothelial cells (see Frazier, $Curr\ Opin\ Cell\ Biol$ 3(5): 792–799, 1991) and the cDNA encoding the subunit has been cloned (Hennessy, et al., 1989, $J\ Cell\ Biol$ 108(2): 729–736; Lawler and Hynes, $J\ Cell\ Biol$ 103(5): 1635–1648, 1986). Native TSP-1 has been shown to block endothelial cell migration in vitro and neovascularization in vivo (Good et al, $Proc\ Natl\ Acad\ Sci\ USA$ 87(17): 6624–6628, 1990). Expression of TSP-1 in tumor cells also suppresses tumorigenesis and tumor-induced angiogenesis (Sheibani and Frazier, $Proc\ Natl\ Acad\ Sci\ USA$ 92(15) 6788–6792, 1995; Weinstat-Saslow et al., $Cancer\ Res$ 54(24):6504–6511, 1994). The antiangiogenic activity of TSP-1 has been shown to reside in two distinct domains of this protein (Tolsma et al, $J\ Cell\ Biol$ 122(2): 497–511, 1993). One of these domains consists of residues 303 to 309 of native TSP-1 and the other consists of residues 481 to 499 of TSP-1. Another important domain consists of the sequence CSVTCG which appears to mediate the binding of TSP-1 to some tumor cell types (Tuszynski and Nicosia, $Bioessays$ 18(1): 71–76, 1996).

The phrase "integrin antagonist" includes agents that impair endothelial cell adhesion via the various integrins. Integrin antagonists induce improperly proliferating endothelial cells to die, by interfering with molecules that blood vessel cells use to bridge between a parent blood vessel and a tumor.

Adhesion forces are critical for many normal physiological functions. Disruptions in these forces, through alterations in cell adhesion factors, are implicated in a variety of disorders, including cancer, stroke, osteoporosis, restenosis, and rheumatoid arthritis (A. F. Horwitz, $Scientific American$, 276:(5): 68–75, 1997).

Integrins are a large family of cell surface glycoproteins which mediate cell adhesion and play central roles in many adhesion phenomena. Integrins are heterodimers composed of noncovalently linked alpha and beta polypeptide subunits. Currently eleven different alpha subunits have been identified and six different beta subunits have been identified. The various alpha subunits can combine with various beta subunits to form distinct integrins.

One integrin known as $a_vb_3$ (or the vitronectin receptor) is normally associated with endothelial cells and smooth muscle cells. $a_vb_3$ integrins can promote the formation of blood vessels (angiogenesis) in tumors. These vessels nourish the tumors and provide access routes into the bloodstream for metastatic cells.

The $a_vb_3$ integrin is also known to play a role in various other disease states or conditions including tumor metastasis, solid tumor growth (neoplasia), osteoporosis, Paget's disease, humoral hypercalcemia of malignancy, angiogenesis, including tumor angiogenesis, retinopathy, arthritis, including rheumatoid arthritis, periodontal disease, psoriasis, and smooth muscle cell migration (e.g. restenosis).

Tumor cell invasion occurs by a three step process: 1) tumor cell attachment to extracellular matrix; 2) proteolytic dissolution of the matrix; and 3) movement of the cells through the dissolved barrier. This process can occur repeatedly and can result in metastases at sites distant from the original tumor.

The $a_vb_3$ integrin and a variety of other $a_v$-containing integrins bind to a number of Arg-Gly-Asp (RGD) containing matrix macromolecules. Compounds containing the RGD sequence mimic extracellular matrix ligands and bind to cell surface receptors. Fibronectin and vitronectin are among the major binding partners of $a_vb_3$ integrin. Other proteins and peptides also bind the $a_vb_3$ ligand. These include the disintegrins (M. Pfaff et al., $Cell\ Adhes.\ Commun.$ 2(6): 491–501, 1994), peptides derived from phage display libraries (Healy, J. M. et al., $Protein\ Pept.\ Lett.$ 3(1): 23–30, 1996; Hart, S. L. et al., $J.\ Biol.\ Chem.$ 269(17): 12468–12474, 1994) and small cyclic RGD peptides (M. Pfaff et al., $J.\ Biol.\ Chem.$, 269(32): 20233–20238, 1994). The monoclonal antibody LM609 is also an $a_vb_3$ integrin antagonist (D. A. Cheresh et al., $J.\ Biol.\ Chem.$, 262(36): 17703–17711, 1987).

$A_vb_3$ inhibitors are being developed as potential anti-cancer agents. Compounds that impair endothelial cell adhesion via the $a_vb_3$ integrin induce improperly proliferating endothelial cells to die.

The $a_vb_3$ integrin has been shown to play a role in melanoma cell invasion (Seftor et al., $Proc.\ Natl.\ Acad.\ Sci.\ USA$, 89: 1557–1561, 1992). The $a_vb_3$ integrin expressed on human melanoma cells has also been shown to promote a survival signal, protecting the cells from apoptosis (Montgomery et al., $Proc.\ Natl.\ Acad.\ Sci.\ USA$, 91: 8856–8860, 1994).

Mediation of the tumor cell metastatic pathway by interference with the $a_vb_3$ integrin cell adhesion receptor to impede tumor metastasis would be beneficial. Antagonists of $a_vb_3$ have been shown to provide a therapeutic approach for the treatment of neoplasia (inhibition of solid tumor growth) because systemic administration of $a_vb_3$ antagonists causes dramatic regression of various histologically distinct human tumors (Brooks et al., $Cell$, 79: 1157–1164, 1994).

The adhesion receptor identified as integrin $a_vb_3$ is a marker of angiogenic blood vessels in chick and man. This receptor plays a critical role in angiogenesis or neovascularization. Angiogenesis is characterized by the invasion, migration and proliferation of smooth muscle and endothelial cells by new blood vessels. Antagonists of $a_vb_3$ inhibit this process by selectively promoting apoptosis of cells in the neovasculature. The growth of new blood vessels, also contributes to pathological conditions such as diabetic retinopathy (Adonis et al., $Amer.\ J.\ Ophthal.$, 118. 445–450, 1994) and rheumatoid arthritis (Peacock et al., $J.\ Exp.\ Med.$, 175: 1135–1138, 1992). Therefore, $a_vb_3$ antagonists can be useful therapeutic targets for treating such conditions associated with neovascularization (Brooks et al., $Science$, 264: 569–571, 1994).

The $a_vb_3$ cell surface receptor is also the major integrin on osteoclasts responsible for the attachment to the matrix of bone. Osteoclasts cause bone resorption and when such bone resorbing activity exceeds bone forming activity, osteoporosis (a loss of bone) results, which leads to an increased number of bone fractures, incapacitation and increased mortality. Antagonists of $a_vb_3$ have been shown to be potent inhibitors of osteoclastic activity both in vitro (Sato et al., $J.\ Cell.\ Biol.$, 111: 1713–1723, 1990) and in vivo (Fisher et al., $Endocrinology$, 132: 1411–1413, 1993). Antagonism of $a_vb_3$ leads to decreased bone resorption and therefore assists in restoring a normal balance of bone forming and resorbing activity. Thus it would be beneficial to provide antagonists of osteoclast $a_vb_3$ which are effective inhibitors of bone resorption and therefore are useful in the treatment or prevention of osteoporosis.

PCT Int. Appl. Wo 97/08145 by Sikorski et al., discloses meta-guanidine, urea, thiourea or azacyclic amino benzoic acid derivatives as highly specific $a_vb_3$ integrin antagonists. PCT Int. Appl. WO 96/00574 A1 960111 by Cousins, R. D. et. al., describe preparation of 3-oxo-2,3,4,5-tetrahydro-1H-1,4-benzodiazepine and -2-benzazepine derivatives and analogs as vitronectin receptor antagonists. PCT Int. Appl. WO 97/23480 A1 970703 by Jadhav, P. K. et. al. describe annelated pyrazoles as novel integrin receptor antagonists. Novel heterocycles including 3-[1-[3-(imidazolin-2-ylamino)propyl]indazol-5-ylcarbonylamino]-2-(benzyl oxycarbonylamino)propionic acid, which are useful as antagonists of the $a_vb_3$ integrin and related cell surface adhesive protein receptors. PT Int. Appl. WO 97/26250 A1 970724 by Hartman, G. D. et al., describe the preparation of arginine dipeptide mimics as integrin receptor antagonists. Selected compounds were shown to bind to human integrin $a_vb_3$ with EIB <1000 nM and claimed as compounds, useful for inhibiting the binding of fibrinogen to blood platelets and for inhibiting the aggregation of blood platelets. PCT Int. Appl. WO 97/23451 by Diefenbach, B. et. al. describe a series of tyrosine-derivatives used as alpha v-integrin inhibitors for treating tumors, osteoporosis, osteolytic disorder and for suppressing angiogenesis. PCT Int. Appl. WO 96/16983 A1 960606, by Vuori, K. and Ruoslahti, E. describe cooperative combinations of $a_vb_3$ integrin ligand and second ligand contained within a matrix, and use in wound healing and tissue regeneration. The compounds contain a ligand for the $a_vb_3$ integrin and a ligand for the insulin receptor, the PDGF receptor, the IL-4 receptor, or the IGF receptor, combined in a biodegradable polymeric (e.g. hyaluronic acid) matrix. PCT Int. Appl. WO 97/10507 A1 970320 by Ruoslahti, E; and Pasqualini, R. describe peptides that home to a selected organ or tissue in vivo, and methods of identifying them. A brain-homing peptide, nine amino acid residues long, for example, directs red blood cells to the brain. Also described is use of in vivo panning to identify peptides homing to a breast tumor or a melanoma. PCT Int. Appl. Wo 96/01653 A1 960125 by Thorpe, Philip E.; Edgington, Thomas S. describes bifunctional ligands for specific tumor inhibition by blood coagulation in tumor vasculature. The disclosed bispecific binding ligands bind through a first binding region to a disease-related target cell, e.g. a tumor cell or tumor vasculature; the second region has coagulation-promoting activity or is a binding region for a coagulation factor. The disclosed bispecific binding ligand may be a bispecific (monoclonal) antibody, or the two ligands may be connected by a (selectively cleavable) covalent bond, a chemical linking agent, an avidin-biotin linkage, and the like. The target of the first binding region can be a cytokine-inducible component, and the cytokine can be released in response to a leukocyte-activating antibody; this may be a bispecific antibody which crosslinks activated leukocytes with tumor cells.

The phrase "cyclooxygenase-2 inhibitor" or "COX-2 inhibitor" or "cyclooxygenase-II inhibitor" includes agents that specifically inhibit a class of enzymes, cyclooxygenase-2, without significant inhibition of cyclooxygenase-1. Preferably, it includes compounds which have a cyclooxygenase-2 $IC_{50}$ of less than about 0.2 $\mu$M, and also have a selectivity ratio of cyclooxygenase-2 inhibition over cyclooxygenase-1 inhibition of at least 50, and more preferably of at least 100. Even more preferably, the compounds have a cyclooxygenase-1 $IC_{50}$ of greater than about 1 $\mu$M, and more preferably of greater than 10 $\mu$M.

Studies indicate that prostaglandins synthesized by cyclooxygenases play a critical role in the initiation and promotion of cancer. Moreover, COX-2 is overexpressed in neoplastic lesions of the colon, breast, lung, prostate, esophagus, pancreas, intestine, cervix, ovaries, urinary bladder, and head & neck. In several in vitro and animal models, COX-2 inhibitors have inhibited tumor growth and metastasis. Non-limiting examples of COX-2 inhibitors include rofecoxib and JTE-522.

The phrase "matrix metalloproteinase inhibitor" or "MMP inhibitor" includes agents that specifically inhibit a class of enzymes, the zinc metalloproteinases (metalloproteases). The zinc metalloproteinases are involved in the degradation of connective tissue or connective tissue components. These enzymes are released from resident tissue cells and/or invading inflammatory or tumor cells. Blocking the action of zinc metalloproteinases interferes with the creation of paths for newly forming blood vessels to follow. Examples of MMP inhibitors are described in Golub, L M, Inhibition of Matrix Metalloproteinases: Therapeutic Applications (Annals of the New York Academy of Science, Vol 878). Robert A. Greenwald and Stanley Zucker (Eds.), June 1999), and is hereby incorporated by reference.

Connective tissue, extracellular matrix constituents and basement membranes are required components of all mammals. These components are the biological materials that provide rigidity, differentiation, attachments and, in some cases, elasticity to biological systems including human beings and other mammals. Connective tissues components include, for example, collagen, elastin, proteoglycans, fibronectin and laminin. These biochemicals makeup, or are components of structures, such as skin, bone, teeth, tendon, cartilage, basement membrane, blood vessels, cornea and vitreous humor.

Under normal conditions, connective tissue turnover and/or repair processes are controlled and in equilibrium. The loss of this balance for whatever reason leads to a number of disease states. Inhibition of the enzymes responsible loss of equilibrium provides a control mechanism for this tissue decomposition and, therefore, a treatment for these diseases.

Degradation of connective tissue or connective tissue components is carried out by the action of proteinase enzymes released from resident tissue cells and/or invading inflammatory or tumor cells. A major class of enzymes involved in this function are the zinc metalloproteinases (metalloproteases).

The metalloprotease enzymes are divided into classes with some members having several different names in common use. Examples are: collagenase I (MMP-1, fibroblast collagenase; EC 3.4.24.3); collagenase II (MMP-8, neutrophil collagenase; EC 3.4.24.34), collagenase III (MMP-13), stromelysin 1 (MMP-3; EC 3.4.24.17), stromelysin 2 (MMP-10; EC 3.4.24.22), proteoglycanase, matrilysin (MMP-7), gelatinase A (MMP-2, 72 kDa gelatinase, basement membrane collagenase; EC 3.4.24.24), gelatinase B (MMP-9, 92 kDa gelatinase; EC 3.4.24.35), stromelysin 3 (MMP-11), metalloelastase (MMP-12, HME, human macrophage elastase) and membrane MMP (MMP-14). MMP is an abbreviation or acronym representing the term Matrix Metalloprotease with the attached numerals providing differentiation between specific members of the MMP group.

The uncontrolled breakdown of connective tissue by metalloproteases is a feature of many pathological conditions. Examples include rheumatoid arthritis, osteoarthritis, septic arthritis; corneal, epidermal or gastric ulceration; tumor metastasis, invasion or angiogenesis; periodontal disease; proteinuria; Alzheimer's Disease; coronary thrombosis and bone disease. Defective injury repair processes also occur. This can produce improper wound healing leading to weak repairs, adhesions and scarring. These latter defects can lead to disfigurement and/or permanent disabilities as with post-surgical adhesions.

Matrix metalloproteases are also involved in the biosynthesis of tumor necrosis factor (TNF) and inhibition of the production or action of TNF and related compounds is an important clinical disease treatment mechanism. TNF-α, for example, is a cytokine that at present is thought to be produced initially as a 28 kD cell-associated molecule. It is released as an active, 17 kD form that can mediate a large integer of deleterious effects in vitro and in vivo. For example, TNF can cause and/or contribute to the effects of inflammation, rheumatoid arthritis, autoimmune disease, multiple sclerosis, graft rejection, fibrotic disease, cancer, infectious diseases, malaria, mycobacterial infection, meningitis, fever, psoriasis, cardiovascular/pulmonary effects such as post-ischemic reperfusion injury, congestive heart failure, hemorrhage, coagulation, hyperoxic alveolar injury, radiation damage and acute phase responses like those seen with infections and sepsis and during shock such as septic shock and hemodynamic shock. Chronic release of active TNF can cause cachexia and anorexia. TNF can be lethal.

TNF-α convertase is a metalloproteinase involved in the formation of active TNF-α. Inhibition of TNF-α convertase inhibits production of active TNF-α. Compounds that inhibit both MMPs activity have been disclosed in, for example PCT Publication WO 94/24140. Other compounds that inhibit both MMPs activity have also been disclosed in WO 94/02466. Still other compounds that inhibit both MMPs activity have been disclosed in WO 97/20824.

There remains a need for effective MMP and TNF-α convertase inhibiting agents. Compounds that inhibit MMPs such as collagenase, stromelysin and gelatinase have been shown to inhibit the release of TNF (Gearing et al. *Nature* 376, 555–557 (1994)). McGeehan et al., *Nature* 376, 558–561 (1994) also reports such findings.

MMPs are involved in other biochemical processes in mammals as well. Included is the control of ovulation, post-partum uterine involution, possibly implantation, cleavage of APP (β-Amyloid Precursor Protein) to the amyloid plaque and inactivation of $\alpha_1$-protease inhibitor ($\alpha_1$-PI). Inhibition of these metalloproteases permits the control of fertility and the treatment or prevention of Alzheimers Disease. In addition, increasing and maintaining the levels of an endogenous or administered serine protease inhibitor drug or biochemical such as $\alpha_1$-PI supports the treatment and prevention of diseases such as emphysema, pulmonary diseases, inflammatory diseases and diseases of aging such as loss of skin or organ stretch and resiliency.

Inhibition of selected MMPs can also be desirable in other instances. Treatment of cancer and/or inhibition of metastasis and/or inhibition of angiogenesis are examples of approaches to the treatment of diseases wherein the selective inhibition of stromelysin (MMP-3), gelatinase (MMP-2), or collagenase III (MMP-13) are the relatively most important enzyme or enzymes to inhibit especially when compared with collagenase I (MMP-1). A drug that does not inhibit collagenase I can have a superior therapeutic profile.

Inhibitors of metalloproteases are known. Examples include natural biochemicals such as tissue inhibitor of metalloproteinase (TIMP), $\alpha_2$-macroglobulin and their analogs or derivatives. These are high molecular weight protein molecules that form inactive complexes with metalloproteases. An integer of smaller peptide-like compounds that inhibit metalloproteases have been described. Mercaptoamide peptidyl derivatives have shown ACE inhibition in vitro and in vivo. Angiotensin converting enzyme (ACE) aids in the production of angiotensin II, a potent pressor substance in mammals and inhibition of this enzyme leads to the lowering of blood pressure.

Thiol group-containing amide or peptidyl amide-based metalloprotease (MMP) inhibitors are known as is shown in, for example, WO 95/12389. Thiol group-containing amide or peptidyl amide-based metalloprotease (MMP) inhibitors are also shown in WO 96/11209. Still furhter Thiol group-containing amide or peptidyl amide-based metalloprotease (MMP) inhibitors are shown in U.S. Pat. No. 4,595,700. Hydroxamate group-containing MMP inhibitors are disclosed in a number of published patent applications that disclose carbon back-boned compounds, such as in WO 95/29892. Other published patents include Wo 97/24117. Additionally, EP 0 780 386 further discloses hydroxamate group-containing MMP inhibitors. WO 90/05719 disclose hydroxamates that have a peptidyl back-bones or peptidomimetic back-bones. WO 93/20047 also discloses hydroxamates that have a peptidyl back-bones or peptidomimetic back-bones. Additionally, WO 95/09841 discloses disclose hydroxamates that have peptidyl back-bones or peptidomimetic back-bones. And WO 96/06074 further discloses hydroxamates that have peptidyl back-bones or peptidomimetic back-bones. Schwartz et al., *Progr. Med. Chem.*, 29:271–334(1992) also discloses disclose hydroxamates that have peptidyl back-bones or peptidomimetic back-bones. Furthermore, Rasmussen et al., *Pharmacol. Ther.*, 75(1): 69–75 (1997) discloses hydroxamates that have peptidyl back-bones or peptidomimetic back-bones. Also, Denis et al., *Invest. New Drugs*, 15(3): 175–185 (1997) discloses hydroxamates that have a peptidyl back-bones or peptidomimetic back-bones as well.

One possible problem associated with known MMP inhibitors is that such compounds often exhibit the same or similar inhibitory effects against each of the MMP enzymes. For example, the peptidomimetic hydroxamate known as batimastat is reported to exhibit $IC_{50}$ values of about 1 to about 20 nanomolar (nM) against each of MMP-1, MMP-2, MMP-3, MMP-7, and MMP-9. Marimastat, another peptidomimetic hydroxamate was reported to be another broad-spectrum MMP inhibitor with an enzyme inhibitory spectrum very similar to batimastat, except that marimastat exhibited an $IC_{50}$ value against MMP-3 of 230 nM. Rasmussen et al., *Pharmacol. Ther.*, 75(1): 69–75 (1997).

Meta analysis of data from Phase I/II studies using marimastat in patients with advanced, rapidly progressive, treatment-refractory solid tumor cancers (colorectal, pancreatic, ovarian, prostate), indicated a dose-related reduction in the rise of cancer-specific antigens used as surrogate markers for biological activity. The most common drug-related toxicity of marimastat in those clinical trials was musculoskeletal pain and stiffness, often commencing in the small joints in the hands, spreading to the arms and shoulder. A short dosing holiday of 1–3 weeks followed by dosage reduction permits treatment to continue. Rasmussen et al., *Pharmacol. Ther.*, 75(1): 69–75 (1997). It is thought that the lack of specificity of inhibitory effect among the MMPs may be the cause of that effect.

In view of the importance of hydroxamate MMP inhibitor compounds in the treatment of several diseases and the lack of enzyme specificity exhibited by two of the more potent drugs now in clinical trials, it would be beneficial to use hydroxamates of greater enzyme specificity. This would be particularly the case if the hydroxamate inhibitors exhibited limited inhibition of MMP-1 that is relatively ubiquitous and as yet not associated with any pathological condition, while exhibiting quite high inhibitory activity against one or more of MMP-2, MMP-9 or MMP-13 that are associated with several pathological conditions.

Non-limiting examples of matrix metalloproteinase inhibitors that may be used in the present invention are identified in Table No. 1, below.

TABLE No. 1

Matrix metalloproteinase inhibitors.

| Compound | Trade Name | Reference | Dosage |
|---|---|---|---|
| Biphenyl hydroxamate | | WO 97/18188 | |
| | AG-3067 (Agouron Pharm. Inc.) | Winter Conf. Med. Bio-organic Chem. 1997 January, 26–31 | |
| | AG-3340 (Agouron Pharm. Inc.) | WO 97/20824 | 50 mg/kg treatment of Lewis lung carcinomas in test animals |
| | AG-2024 (Agouron Pharm. Inc.) | | |
| | AG-3365 (Agouron Pharm. Inc.) | | |
| 3(S)-N-hydroxy-4-(4-[4-(imidazol-1-yl)phenoxy] benzenesulfonyl)-2,2-dimethyl-tetrahydro-2H-1,4-thiazine-3-carboxamide, and derivatives thereof | | WO 97/20824. FEBS (1992) 296 (3):263 | In female Lewis rats, arthritis model: dose of 25 mg/kg/day gave 97.5% weight loss inhibition |
| Heteroaryl succinamides derivatives | | WO 98/17643 | |
| | AG-3296 (Agouron Pharm. Inc.) | | |
| | AG-3287 (Agouron Pharm. Inc.) | | |
| | AG-3293 (Agouron Pharm. Inc.) | | |
| | AG-3294 (Agouron Pharm. Inc.) | | |
| | AG-3067 (Agouron Pharm. Inc.) | Winter Conf Med Bio-organic Chem 1997 January 26–31 EP 0818443 | |
| 2R,4S)-4-hydroxy-2-isobutyl-5-mercapto-N-[(1S)-2,2-dimethyl-1-methylcarbamoyl-propyl] pentanamide | | | |
| N-alkyl, N-phenylsulfonyl-N'-hydroxamic acid derivatives of heteroaryl carboxylic acids | | WO 98/16520 | |
| Novel N-alkyl, phenylsulfonyl - N'-hydroxamic acid derivatives of heteroaryl carboxylic acids | | WO 98/16514 | |
| Novel N-alkyl, phenylsulfonyl-N'-hydroxamic acid derivatives of cycloalkane carboxylic acids | | WO 98/16506 | |
| Novel N-alkyl, N-phenylsulfonyl-N'-hydroxamic acid derivatives of anthranilic acid | | WO 98/16503 | |
| sulfonamido-hydroxamic acid derivatives | | EP 03/98753 | |
| TIMP-3: polynucleotides encoding endogenous (human) peptides (3alpha, 5beta, 6alpha, 7alphabeta)-4',4'-(hexahydro-2,2-dimethyl-1,3-benzodioxole-5,6-diyl)bis(2,6-piperazinedione) and derivatives thereof | | WO 95/09918 WO 93/23075 | |
| | BE-16627B | WO 91/08222. Int. J. Cancer 1994 58 5 730–735 | |
| (2S)-4-(4-(4-chlorophenyl) phenyl)-4-oxo-2-(2-phthalimidoethyl) butanoic acid | | WO 96/15096 | |
| | Bay-12-9566 | WO 96/15096 | 10 to 400 mg/day |
| 4-oxo-2-(2-phthalimidoethyl alkanoic acid derivatives | | WO 97/43238 | |
| Novel 4-(4-Alkynylphenyl) 4-oxobutanoic acid derivatives | | WO 97/43237 | |
| Substituted 4-biarylbutyric or biarylpentanoic acids and derivatives | | WO 96/15096 | |
| Substituted 4-biphenyl-4-hydroxybutyric acid derivatives | | WO 98/22436 | |

TABLE No. 1-continued

Matrix metalloproteinase inhibitors.

| Compound | Trade Name | Reference | Dosage |
|---|---|---|---|
| 2R,S)-HONH-CO-CH(i-Bu)-CO-Ala-Gly-NH2, | | J Med Chem 1998 41 3 339–345 | |
| batimastat; BB-94; Hydroxamic acid based collagenase inhibitors | | WO 90/05719 | 15 to 135 mg/m2 administered intrapleurally |
| Hydroxamic acid based collagenase inhibitors | | WO 90/05719 | |
| marimastat BB-2516; Hydroxamic acid derivatives | | WO 94/02447 | 5 to 800 mg daily |
| alpha-cycloalkyl analogs of marimastat | | Bio-organic Med Chem Lett 1998 8 11 1359–1364 | |
| | GI-245402 (BB-2983) | | |
| Hydroxamic acid derivatives | | WO 94/21625 | |
| Succinyl hydroxamic acid, N-formyl-N-hydroxy amino carboxylic acid and succinic acid amide derivatives | | WO 95/32944 | |
| hydroxamic acid, N-formyl-N-hydroxyamino and carboxylic acid derivatives, pseudopeptide | | WO 97/19053 | |
| hydroxamic and carboxylic acid derivatives from the corresponding lactone and alpha-amino acid | | WO 97/19050 | |
| Succinic acid amide derivatives | | WO 97/03966. GB 95/00111. GB 95/00121. | |
| Hydroxamic acid derivatives | | WO 97/02239 | |
| Succinamidyl (alpha substituted) hydroxamic acid derivatives | | WO 96/33165 | |
| (2S,3R)-3-[2,2-dimethyl-1S-(thiazol-2-ylcarbamoyl)propylcarbamoyl[-5-methyl-2-(prop-2-enyl)hexano-hydroxanic acid and derivatives thereof | | WO 96/25156 | |
| Hydroxamic or carboxylic acid derivatives | | WO 96/16931 | |
| hydroxamic and carboxylic acids | | WO 96/06074 | |

TABLE No. 1-continued

Matrix metalloproteinase inhibitors.

| Compound | Trade Name | Reference | Dosage |
|---|---|---|---|
| 2-[(1S)-1-((1R)-2-[[1,1'-biphenyl]-4-ylmethylthio]-1-[(1S)-2,2-dimethyl-1-(methylcarbamoyl)propylcarbamoyl]ethylcarbamoyl)-4-(1,3-dioxo-1,3-dihydroisoindol-2-yl)butylthio]-acetate, and derivatives thereof | | WO 98/23588 | |
| Hydroxamic acid derivatives as inhibitors of cytokine production | | WO 95/09841 | |
| Hydroxamic acid derivatives | | WO 94/24140 | |
| Aromatic or heteroaryl substituted hydroxamic or carboxylic acid derivatives | | WO 95/19956 | |
| Hydroxamic acid derivatives | | WO 95/19957 | Doses are preferably 1 to 100 mg/kg. |
| Hydroxamic acid and carboxylic acid derivatives | | WO 95/19961 | Doses are preferably 1 to 100 mg/kg. |
| Butanediamide, N1-[1(cyclohexyl-methyl)-2(methylamino)-2-oxoethyl]-N4,3-dihydroxy-2-(2-methylpropyl)-, [2R[N1(S*),2R*,3S*]]- | BB-1433 | | At 50 mg/kg bid. p.o. inhibited bone mineral density loss |
| tetracycline analogs and D-penicillamine | | EP 733369 | D-penicillamine reduced allergic encephalitis symptom scores in a dose dependent manner at 27, 125 and 375 mug with complete inhibition |
| | CDP-845 | Biochem Pharmacol 1990 39 12 2041–2049 | |

TABLE No. 1-continued

Matrix metalloproteinase inhibitors.

| Compound | Trade Name | Reference | Dosage |
|---|---|---|---|
| succinamide derivatives | | WO 95/04033 | oral bioavailability by murine pleural cavity assay in the presence of gelatinase: Between 73% and 100% inhibition was displayed at 10 mg/kg for six of the compounds. The seventh displayed 100% inhibition at 80 mg/kg. |
| Peptidyl derivatives | | WO 94/25435. WO 94/25434 | |
| Mercaptoalkyl-peptidyl compounds having an imidazole substituent | | WO 97/19075 | |
| mercaptoalkyl-peptide derivatives | | WO 97/38007. WO 95/12389. WO 96/11209. | |
| Mercaptoalkyl-amide derivatives | | WO 97/37974 | |
| arylsulfonyl-hydrazine derivatives | | WO 97/37973. WO 95/12389 | |
| N-acetylthio-lacetyl-N-(3-phthalimidopropyl)-L-leucyl-L-phenylalanine N-methylamide | | WO 96/35714 | |
| 2-acetylsulfanyl-5-phthalimido-pentanoyl-L-leucineN-(2-phenylethyl)-amide | | WO 96/35712 | dosages of about 0.5 mg to 3.5 g per day for the treatment of inflammation |
| 5-phthalimido-pentanoyl-L-leucyl-L-phenylalanineN-methylamide | | WO 96/35711 | |
| peptidyl derivatives | | WO 98/06696 | |
| 4-[4-(methoxycarbonyl methoxy)-3,5-dimethylphenyl]-2-methyl-1(2H)-phthalazinone, and hydroxamic and carboxylic acid derivatives | | WO 98/05635 | |
| thio-substituted peptides | | WO 97/12902 | |
| Mercaptoamides Peptidyl derivatives having SH or acylo groups which are amides, primary amides or thioamides | | WO 97/12861 WO 96/35687 | |
| | D-5410 (Chiroscience Group plc) | WO 95/13289 | |
| | CH-104, (Chiroscience Group plc) D-2163 (Chiro Science Ltd.) D-1927 (Chiro Science Ltd.) Dermastat (Colla-Genex Pharmaceutical Inc.) Metastat (Colla-Genex) Osteostat (Colla-Genex Pharmaceutical Inc.) doxycycline; Roche; Periostat | | Gingival crevicular fluid collagenase is reported to be inhibited at concentrations of 5–10 microg/ml or 15–30 microM |
| 2S, 5R, 6S-3-aza-4-oxo-10-oxa-5-isobutyl-2-(N-methylcarbox-amido)-[10]paracyclo-phane-6-N-hydroxycarbox-amide | | WO 97/18207 | |
| hydroxamic acid and amino-carboxylate compounds | | WO 96/33176 | |
| N-hydroxamic derivatives of succinamide | | WO 96/33166 | |

TABLE No. 1-continued

Matrix metalloproteinase inhibitors.

| Compound | Trade Name | Reference | Dosage |
|---|---|---|---|
| Macrocyclic amino carboxylates | SE-205 (DuPont Merck Pharm Co.) | J Med Chem 1998 41 11 1749–1751 Bio-organic Med Chem Lett 1998 8 7 837–842. J Med Chem 1998 41 11 1745–1748 | |
| macrocyclic matrix metalloprotease-8 inhibitors | | | |
| Hydroxamic acid and carboxylic acid derivatives | | WO 95/22966 | |
| succinamid derivatives | | U.S. Pat. No. 5256657 | |
| mercaptosulfide derivatives | | WO 95/09833 | |
| sulfoximine and sulfodiimine derivatised peptides | | WO 95/09620 | |
| water soluble MMP inhibitors | | WO 96/33968 | |
| hydantoin derivatives | | EP 06/40594 | |
| Piperazine derivatives | | WO 98/27069 | |
| | GI-155704A | J Med Chem 1994 37 5 674. Bioorganic Med Chem Lett 1996 6 16 1905–1910 | |
| Cyclic imide derivatives. | | EP 05/20573 | |
| 3-(mercapto-methyl) hexa-hydro-2,5-pyrazinedione derivatives | | WO 97/48685 | |
| beta-mercaptoketone and beta-mercaptoalcohol derivatives | | WO 96/40738 | |
| | ilomastat MPI; GM-6001; Galardin | U.S. Pat. No. 5114953. Cancer Res 1994 54 17 4715–4718 | eye drops containing ilomastat (800 microg/ml |
| Cyclic and heterocyclic N-substituted alpha-iminohydroxamic and carboxylic acids | | WO 97/18194 | |
| Aminomethyl-phosphonic and aminomethyl-phosphinic acids derivatives | | EP 703239 | |
| 3-Mercapto-acetylamino-1,5-substituted-2-oxo-azepan derivatives | | WO 98/12211 | |
| 2-substituted indane-2-mercaptoacetyl-amide tricyclic derivatives | | WO 94/04531 | |
| | Ro-2756 (Roche Holding AG) | | |
| | Ro-26-4325 (Roche Holding AG) | | |
| | Ro-26-5726 (Roche Holding AG) | | |
| | Ro-26-6307 (Roche Holding AG) | | |
| | Ro-31-9790 (Roche Holding AG) | J Am Soc Nephrol 1995 6 3 904. Inflamm Res 1995 44 8 345–349 | mono-arthritis in rat: 100 mg/kg/day |
| substituted and unsubstituted hydroxamates (specifically N-[D,L-2-isobutyl-3-(N'-hydroxy-carbonyl-amido)-propanoyl]trypto-phanmethylamide) GM6001, N-(2(R)-2-(hydroxyamino-carbonylmethyl)-4-methylpentanoyl) -L-tryptophan methylamide. | | WO 92/09556 | |
| Oligonucleotice (c-jun) | | WO 95/24921 | |
| Sulfated polysaccharides | | WO 98/11141 | |
| | KB-R7785; KB-R8301; KB-R8845 | Life Sci 1997 61 8 795–803 | |
| Fas ligand solubilization inhibitor gelastatin AB, KRIBB | | WO 97/09066 | |
| | KT5-12 (Kotobuki Seiyaku Co Ltd.) | Faseb J 1998 12 5 A773 (4482) | |
| 2-(N2-[(2R)-2-(2-hydroxyamino-2-oxoethyl)-5-(4-methoxyphenoxy)p pentanoyl]-L-phenylalanylamino) ethanesulfonamide, and carboxylic acid derivatives thereof | | GB 23/18789 | |

TABLE No. 1-continued

Matrix metalloproteinase inhibitors.

| Compound | Trade Name | Reference | Dosage |
|---|---|---|---|
| Chromone derivatives | | EP 758649 | 2-Pyrolylthio-chromone in a murine melanoma model produced 37% inhibition at 100 mg/kg |
| Esculetin derivatives, substituted and unsubstituted hyroxyureas and reverse hydroxamates | | EP 719770 WO 92/09563 | |
| Synthetic MMP inhibitors (ex. N-(D,L-2-isobutyl-3-(N'-hydroxycarbonyl-amido)propanoyl) tryptophan methylamide) | | WO 94/22309 | |
| Reverse hydroxamates and hydroxyureas | | WO 95/19965 | in female mice infected w/murine melanoma - init 80 mug followed by 150 mg/kg/day |
| N-(mercaptoacyl)-aryl derivatives of leucine and phenylalanine | | U.S. Pat. No. 5629343 | |
| N-carboxyalkyl derivatives | | WO 95/29689 | |
| Substituted cyclic derivatives | | GB 22/82598 | Inflammation is stated to be effectively treated by oral administration of 0.01 to 50 mg/kg |
| Substituted n-carboxyalkyldi-peptides | | GB 22/72441 | |
| (2S,4R)-2-methyl-4-(phenylamino-carbonylmethyl-aminocarbonyl)-6-(4-propyl-phenyl)hexanoic acid, and carboxylic acid derivatives | | WO 97/11936 | |
| Substituted cyclic derivatives | | U.S. Pat. No. 5403952 | |
| Thiol sulfonamide metalloprotease inhibitors | | WO 98/03166 | |
| Thiol sulfone metalloprotein-ase inhibitors | | WO 98/03164 | |
| formulations containing vanadium compounds and N-acetylcysteine | | WO 97/47296 | |
| | NSC-683551; COL-3 (National Cancer Institute) BB-3644 (Neures Ltd.) | | |
| Arylsulfonamido-substituted hydroxamic acids | CGS-27023A; CGS-25966 | Int Congr Inflamm Res Assoc 1994 7th Abs 73. EP 606046 | 600 mg tid (Ph I - colorectal and melanoma patients); 100 mg/kg in food in osteoarthritis model rabbits |
| alpha-Substituted arylsulfonamido hydroxamic acid derivatives | | WO 97/22587 | |
| Arylsulfonamido-substituted hydroxamic acids | | U.S. Pat. No. 5455258 | active at 30 mg/kg in in vivo assay |
| Arylsulfonamido-substituted hydroxamic acids 2S,3S)-N-hydroxy-5-methyl-2-[2-(2-methoxyethoxy) ethoxymethyl[-3-(N-[(1S)-1-(N-methylcarbamoyl)-2-phenylethyl]carb-amoyl)hexanamide and Hydroxamic acid deriva-tives | | WO 96/00214 WO 98/14424 | |
| arylsulfonamido-substituted hydroxamic acids | | WO 96/40101 | in tumor model mice: administered for 7 to 17 days at a dosage of 30 mg/kg twice daily |
| Aryl (sulfide, sulfoxide and sulfone) derivatives | | WO 97/49679 | |
| Phenylsulfon-amide derivatives | | WO 97/45402 | |
| Arylsulfonamido-aminoacid derivative | | EP 757037 | |
| A1PDX (Oregon Health Sciences University) | | | |

TABLE No. 1-continued

Matrix metalloproteinase inhibitors.

| Compound | Trade Name | Reference | Dosage |
|---|---|---|---|
| futoenone analogs | | Bio-organic Med Chem Lett 1995 5 15 1637–1642 | |
| debromohymenialdisine and related compounds | | WO 96/40147 | preferred 1–30 mg/day |
| amide derivatives of 5-amino-1,3,4-thiadiazolones | | WO 96/40745 | |
| 3S-(4-(N-hydroxylamino)-2R-isobutylsuccinyl)amino-1-methoxymethyl-3,4-dihydrocarbostyril and deriviatives therof | | WO 94/21612 | |
| Carbostyryl derivatives | | JP 8325232 | |
| OPB-3206 (Otsuka Pharmaceutical Co, Ltd.) | | | |
| Arylsulfonyl hydroxamic acid derivatives | | WO 96/33172 | |
| Cyclic sulfone derivatives | | EP 816442 | |
| arylsulfonamido N-hydroxamic acid derivatives of butyric acid | | WO 96/27583 | |
| Arylsulfonyl-amino hydroxamic acid derivatives | | WO 98/07697 | |
| phosphinate-based derivatives | | WO 98/03516 | |
| cyclopentyl-substituted glutaramide derivatives | | WO 92/14706 | |
| N-hydroxamic acid succinamide derivatives | | WO 97/49674 | |
| Thiadiazole amide MMP inhibitors. | | WO 97/48688 | |
| (S)-1-[2-[[[(4,5-Dihydro-5-thioxo-1,3,4-thiadiazol-2-yl)amino]-carbonyl)amino]-1-oxo-3-(pentafluoro-phenyl)propyl]-4-(2-pyridinyl)-piperazine | | WO 97/40031 | |
| hydroxamic acid derivatives of pyrrolidone-3-acetamide. | | WO 97/32846 | |
| alpha-arylsulfonamido-N-hydroxamic acid derivatives | | WO 98/17645 | |
| beta-Sulfonylhydroxamic acids | | WO 98/13340 | |
| Hydroxamic acid derivatives | PNU-99533 (Pharmacia & UpJohn Inc.) PNU-143677 (Pharmacia & UpJohn Inc.) POL-641 (Polifarma) | U.S. Pat. No. 5712300 | |
| Peptidomimetic inhibitors | | WO 96/20,18. WO 96/29313. WO 98/08814. WO 98/08815. WO 98/08850. WO 98/08822. WO 98/08823. WO 98/08825. WO 98/08827. | |
| 2R)-N-hydroxycarbox-amidedemethyl-decanoic acid amide of 1N-(carbomethoxymethyl) | (	)-caprol-actam-(3S)-amine | WO 96/29313 | rheumatoid arthritis: female subject - 50 mg po for 2 yrs; male subject - 70 mg po daily for 5 yrs; corneal ulcer: male subject 0 10 mg in saline soln for 2 months, 2 times/day |
| 3-(N-[(N-Hydroxyamino-carbonyl)methyl]-N-isobutylamino-carbonyl)-2-(R)-isobutylpropanoyl-L-phenylalanine amide | | WO 96/20918 | |
| N-hydroxy-phosphinic acid amides | | WO 98/08853 | |
| N'-arylsulfonyl derivatives of spirocyclic-N-hydroxycarbox-amides | | WO 98/08850 | |
| N'-arylsulfonyl derivatives of thiazepinone and azepinone-N-hydroxycarbox-amides | | WO 98/08827 | |
| Substituted piperazine derivatives | | WO 98/08825 | |

TABLE No. 1-continued

Matrix metalloproteinase inhibitors.

| Compound | Trade Name | Reference | Dosage |
|---|---|---|---|
| N'-arylsulfonyl derivatives of pyrimidine, thiazepine and diazepine-N-hydroxycarbox-amides | | WO 98/08823 | |
| Substituted pyrrolidine derivatives | | WO 98/08815 | |
| Substituted heterocycles | | WO 98/08814 | |
| Substituted 1,3-diheterocyclic derivatives | | WO 09/08822 | |
| substituted 5-amino-1,2,4-thiadiazole-2-thiones | | WO 98/25949 | |
| Hydroxamic acid derivatives which inhibit TNF production. | | WO 97/24117 | |
| 6-methoxy-1,2,3,4-tetrahydro-norharman-1-carboxylic acid | | WO 97/37658 | |
| | RS-130830 | Arthritis Rheum 1997 40 9 SUPPL. S128 | |
| Aralkyl MMP inhibitors (ex. N-(2R-carboxymethyl-5-(biphen-4-yl)pentanoyl)-L-t-butylglycine-N'-(pyridin-4-yl)carboxamide) | | WO 96/16027 | |
| | Ro-32-3555 (Roche Holding AG) | | |
| | Ro-32-1278 (Roche Holding AG) | | |
| | Ro-32-1541 (Roche Holding AG) | | |
| | Ro-31-3790 (Roche Holding AG) | | Arthritic model rats: Protection of cartilage degradation |
| (3R,11S)-N-hydroxy-5-methyl-3-(10-oxo-1,9-diazatricyclo-(11.6.1.014,19) eicosa-13(20),14(19),15,17-tetraen-11-ylcarbamoyl) hexanamide and derivatives thereof | | WO 95/04735 | following oral administration; ED50 = 10 mg/kg po |
| Bridged indoles (Roche Holding AG) | | WO 96/23791 | |
| substituted phenylsulfonyl acetamide, propionamide and carboxamide compounds | | EP 780386 | |
| 5-(4'-biphenyl)-5-[N-(4-nitrophenyl) piperazinyl] barbituric acid | | WO 97/23465 | |
| Malonic acid based matrix metalloproteinase inhibitors | | EP 716086 | |
| phenyl carboxamide derivatives | | WO 95/12603 | |
| Malonic acid based mmp inhibitors (specifically 2-(4-acetylamino-benzoyl)-4-methylpentanoic acid) | | EP 716086 | |
| Hydroxyl amine derivatives | Ro-31-4724; Ro-31-7467; | EP 236872 | |

The following individual patent references listed in Table No. 3 below, hereby individually incorporated by reference, describe various MMP inhibitors suitable for use in the present invention described herein, and processes for their manufacture.

TABLE No. 3

| MMP inhibitors | | | |
|---|---|---|---|
| EP 189784 | U.S. Pat. No. 4609667 | WO 98/25949 | WO 98/25580 |
| JP 10130257 | WO 98/17655 | WO 98/17645 | U.S. Pat. No. 5760027 |
| U.S. Pat. No. 5756545 | WO 98/22436 | WO 98/16514 | WO 98/16506 |
| WO 98/13340 | WO 98/16520 | WO 98/16503 | WO 98/12211 |
| WO 98/11908 | WO 98/15525 | WO 98/14424 | WO 98/09958 |
| WO 98/09957 | GB 23/18789 | WO 98/09940 | WO 98/09934 |
| JP 10045699 | WO 98/08853 | WO 98/06711 | WO 98/05635 |
| WO 98/07742 | WO 98/07697 | WO 98/03516 | WO 98/03166 |

TABLE No. 3-continued

MMP inhibitors

| | | | |
|---|---|---|---|
| WO 98/03164 | GB 23/17182 | WO 98/05353 | WO 98/04572 |
| WO 98/04287 | WO 98/02578 | WO 97/48688 | WO 97/48685 |
| WO 97/49679 | WO 97/47599 | WO 97/43247 | WO 97/43240 |
| WO 97/43238 | EP 818443 | EP 818442 | WO 97/45402 |
| WO 97/40031 | WO 97/44315 | WO 97/38705 | U.S. Pat. No. 5679700 |
| WO 97/43245 | WO 97/43239 | WO 97/43237 | JP 09227539 |
| WO 97/42168 | U.S. Pat. No. 5686419 | WO 97/37974 | WO 97/36580 |
| WO 97/25981 | WO 97/24117 | U.S. Pat. No. 5646316 | WO 97/23459 |
| WO 97/22587 | EP 780386 | DE 19548624 | WO 97/19068 |
| WO 97/19075 | WO 97/19050 | WO 97/18188 | WO 97/18194 |
| WO 97/18183 | WO 97/17088 | DE 19542189 | WO 97/15553 |
| WO 97/12902 | WO 97/12861 | WO 97/11936 | WO 97/11693 |
| WO 97/09066 | JP 09025293 | EP 75/8649 | WO 97/03966 |
| WO 97/03783 | EP 75/7984 | WO 97/02239 | WO 96/40745 |
| WO 96/40738 | WO 96/40737 | JP 08/311096 | WO 96/40204 |
| WO 96/40147 | WO 96/38434 | WO 96/35714 | WO 96/35712 |
| WO 96/35711 | WO 96/35687 | EP 74,3,070 | WO 96/33968 |
| WO 96/33165 | WO 96/33176 | WO 96/33172 | WO 96/33166 |
| WO 96/33161 | GB 23/00190 | WO 96/29313 | EP 73/6302 |
| WO 96/29307 | EP 733369 | WO 96/26223 | WO 96/27583 |
| WO 96/25156 | GB 22/98423 | WO 96/23791 | WO 96/23505 |
| GB 22/97324 | DE 19501032 | WO 96/20918 | U.S. Pat. No. 5532265 |
| EP 719770 | WO 96/17838 | WO 96/16931 | WO 96/16648 |
| WO 96/16027 | EP 716086 | WO 96/15096 | JP 08104628 |
| WO 96/13523 | JP 08081443 | WO 96/11209 | EP 703239 |
| WO 96/06074 | WO 95/35276 | WO 96/00214 | WO 95/33731 |
| WO 95/33709 | WO 95/32944 | WO 95/29892 | WO 95/29689 |
| CA 21/16924 | WO 95/24921 | WO 95/24199 | WO 95/23790 |
| WO 95/22966 | GB 22/87023 | WO 95/19965 | WO 95/19961 |
| WO 95/19956 | WO 95/19957 | WO 95/13,289 | WO 95/13380 |
| WO 95/12603 | WO 95/09918 | WO 95/09841 | WO 95/09833 |
| WO 95/09620 | WO 95/08327 | GB 22/82598 | WO 95/07695 |
| WO 95/05478 | WO 95/04735 | WO 95/04033 | WO 95/02603 |
| WO 95/02045 | EP 626378 | WO 94/25435 | WO 94/25434 |
| WO 94/21612 | WO 94/24140 | WO 94/24140 | EP 622079 |
| WO 94/22309 | JP 06256209 | WO 94/21625 | FR 27/03053 |
| EP 606046 | WO 94/12169 | WO 94/11395 | GB 22/72441 |
| WO 94/07481 | WO 94/04190 | WO 94/00119 | GB 22/68934 |
| WO 94/02446 | EP 575844 | WO 93/24475 | WO 93/24449 |
| U.S. Pat. No. 5270326 | U.S. Pat. No. 5256657 | WO 93/20047 | WO 93/18794 |
| WO 93/14199 | WO 93/14096 | WO 93/13741 | WO 93/09090 |
| EP 53/2465 | EP 532156 | WO 93/00427 | WO 92/21360 |
| WO 92/09563 | WO 92/09556 | EP 48/9579 | EP 489577 |
| U.S. Pat. No. 5114953 | EP 45/5818 | U.S. Pat. No. 5010062 | AU 90/53158 |
| WO 97/19075 | U.S. Pat. No. 7488460 | U.S. Pat. No. 7494796 | U.S. Pat. No. 7317407 |
| EP 277428 | EP 23/2027 | WO 96/15096 | WO 97/20824 |
| U.S. Pat. No. 5837696 | | | |

The Marimastat used in the therapeutic combinations of the present invention can be prepared in the manner set forth in WO 94/02,447.

The Bay-12-9566 used in the therapeutic combinations of the present invention can be prepared in the manner set forth in WO 96/15,096.

The AG-3340 used in the therapeutic combinations of the present invention can be prepared in the manner set forth in WO 97/20,824.

The Metastat used in the therapeutic combinations of the present invention can be prepared in the manner set forth in U.S. Pat. No. 5,837,696.

The D-2163 used in the therapeutic combinations of the present invention can be prepared in the manner set forth in WO 97/19,075.

More preferred zinc matrix metalloproteinase inhibitors include those described in the individual U.S. Patent applications, PCT publications and U.S. Patents listed below in Table No. 4, and are hereby individually incorporated by reference.

TABLE No. 4

More preferred zinc matrix metalloproteinase inhibitors

U.S. patent application Ser. No. 97/12,873
U.S. patent application Ser. No. 97/12,874
U.S. patent application Ser. No. 98/04,299
U.S. patent application Ser. No. 98/04,273
U.S. patent application Ser. No. 98/04,297
U.S. patent application Ser. No. 98/04,300
U.S. patent application Ser. No. 60/119,181
WO 94/02447
WO 96/15096
WO 97/20824
WO 97/19075
U.S. Pat. No. 5837696

Even more preferred zinc matrix metalloproteinase inhibitors that may be used in the present invention include:

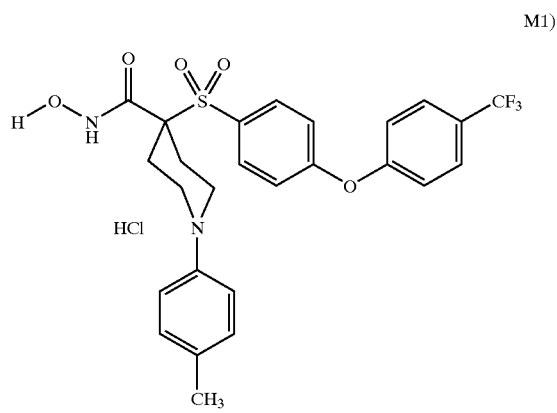

N-hydroxy-1-(4-methylphenyl)-4-[[4-[4-(trifluoromethyl) phenoxy]phenyl]sulfonyl]-4-piperidinecarboxamide monohydrochloride;

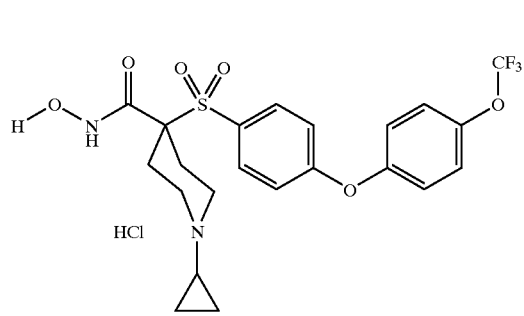

1-cyclopropyl-N-hydroxy-4-[[4-[4-(trifluoromethoxy) phenoxy]phenyl]sulfonyl]-4-piperidinecarboxamide monohydrochloride;

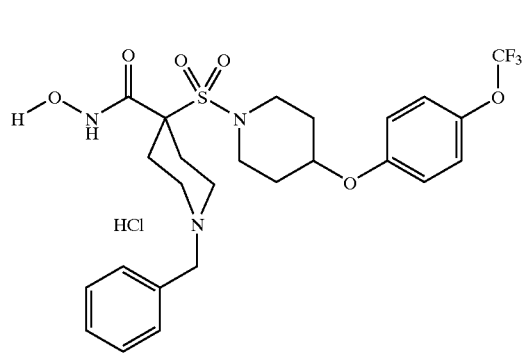

N-hydroxy-1-(phenylmethyl)-4-[[4-[4-(trifluoromethoxy) phenoxy]-1-piperidinyl]sulfonyl]-4-piperidinecarboxamide monohydrochloride;

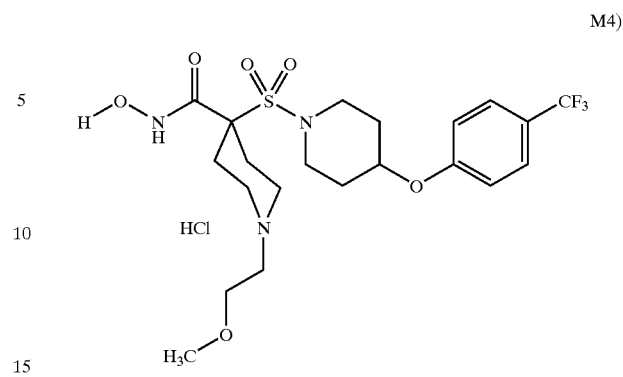

N-hydroxy-1-(4-pyridinylmethyl)-4-[[4-[4-(trifluoromethyl)phenoxy]phenyl]sulfonyl]-4-piperidinecarboxamide dihydrochloride;

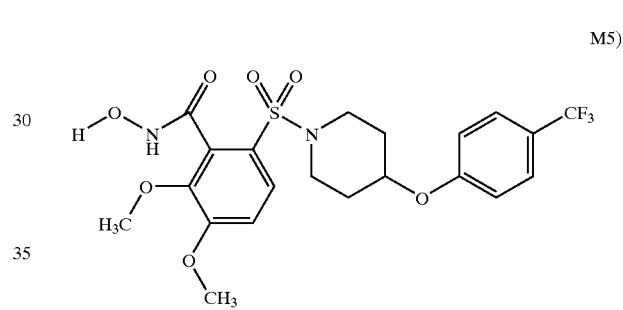

N-hydroxy-2,3-dimethoxy-6-[[4-[4-(trifluoromethyl) phenoxy]-1-piperidinyl]sulfonyl]benzamide;

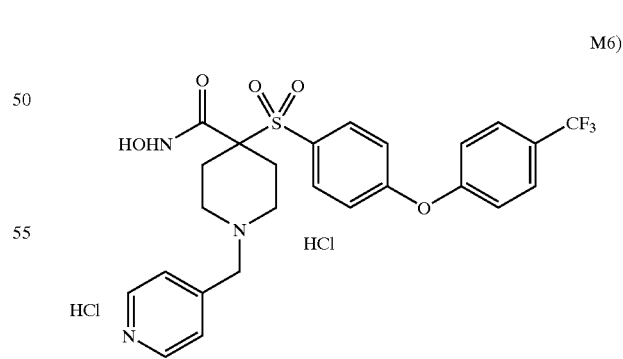

N-hydroxy-1-(4-pyridinylmethyl)-4-[[4-[4-(trifluoromethyl)phenox]phenyl]sulfonyl]-4-piperidinecarboxamide dihydrochloride;

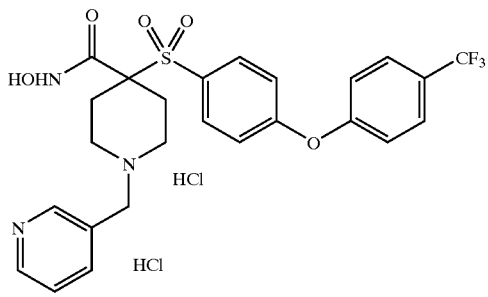

N-hydroxy-1-(3-pyridinylmethyl)-4-[[4-[4-(trifluoromethyl)phenoxy]phenyl]sulfonyl]-4-piperidinecarboxamide dihydrochloride;

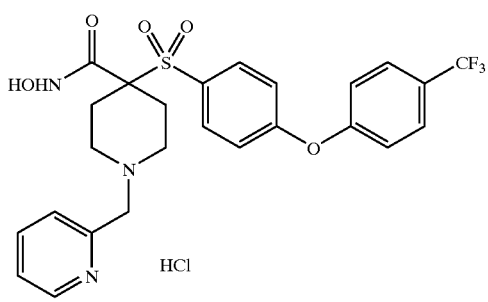

N-hydroxy-1-(2-pyridinylmethyl)-4-[[4-[4-(trifluoromethyl)phenoxy]phenyl]sulfonyl]-4-piperidinecarboxamide monohydrochloride;

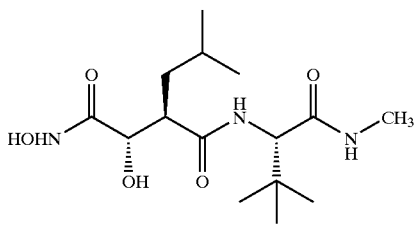

British Biotech BB-2516 (Marimastat), N4-[2,2-dimethyl-1-[(methylamino)carbonyl]propyl]-N1,2-dihydroxy-3-(2-methylpropyl)-, [2S-[N4(R*),2R*,3S*]]-);

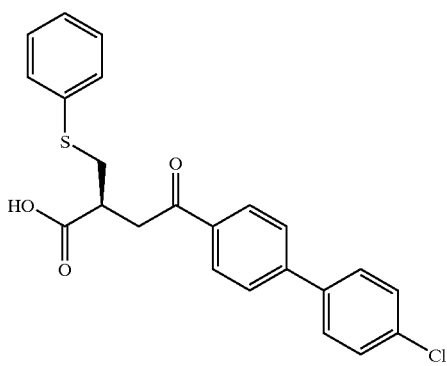

Bayer Ag Bay-12-9566, 4-[(4'-chloro[1,1'-iphenyl]-4-yl)oxy]-2-[(phenylthio)methyl]butanoic acid;

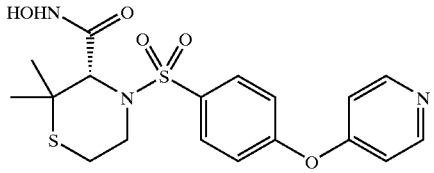

Agouron Pharmaceuticals AG-3340, N-hydroxy-2,2 dimethyl-4-[[4-(4-pyridinyloxy)phenyl]-sulfonyl]-3-thiomorpholinecarboxamide;

M12) CollaGenex Pharmaceuticals CMT-3 (Metastat), 6-demethyl-6-deoxy-4-dedimethylaminotetracycline;

M13) Chiroscience D-2163, 2-[1S-([(2R,S)-acetylmercapto-5-phthalimido]pentanoyl-L-leucyl)amino-3-methylbutyl] imidazole;

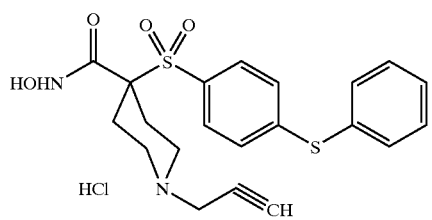

N-hydroxy-4-[[4-(phenylthio)phenyl]sulfonyl]-1-(2-propynyl)-4-piperidinecarboxamide monohydrochloride;

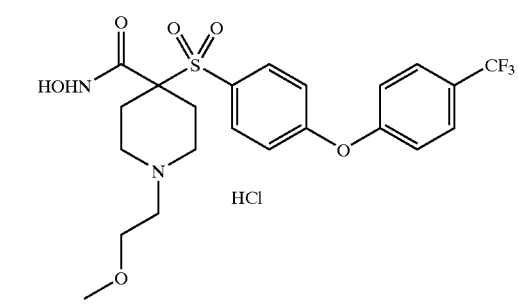

N-hydroxy-1-(2-methoxyethyl)-4-[[4-[4-(trifluoromethbxy)phenoxy]phenyl]sulfonyl]-4-piperidinecarboxamide mono-hydrochloride;

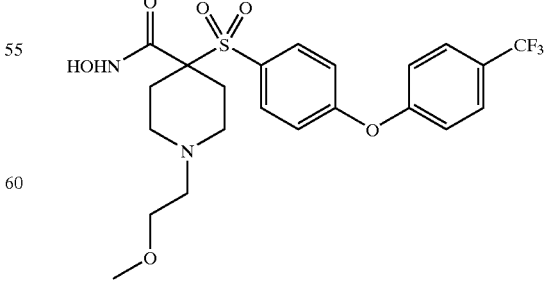

N-hydroxy-1-(2-methoxyethyl)-4-[[4-[4-(trifluoromethyl)phenoxy]phenyl]sulfonyl]-4-piperidinearboxamide;

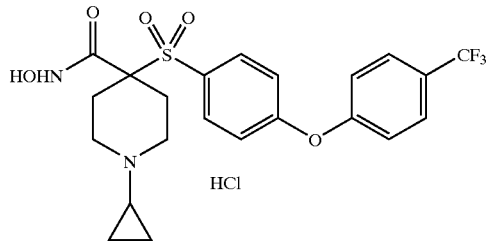

M17)

1-cyclopropyl-N-hydroxy-4-[[4-[4-(trifluoromethyl)phenoxy]phenyl]sulfonyl]-4-piperidinecarboxamide monohydrochloride;

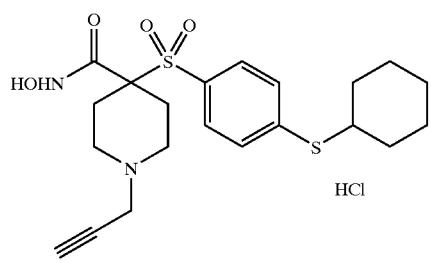

M18)

4-[[4-(cyclohexylthio)phenyl]sulfonyl]-N-hydroxy-1-(2-propynyl)-4-piperidinecarboxamide monohydrochloride;

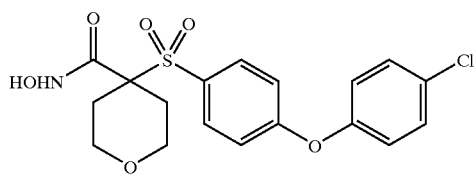

M19)

4-[[4-(4-chlorophenoxy)phenyl]sulfonyl]tetrahydro-N-hydroxy-2H-pyran-4-carboxamide;

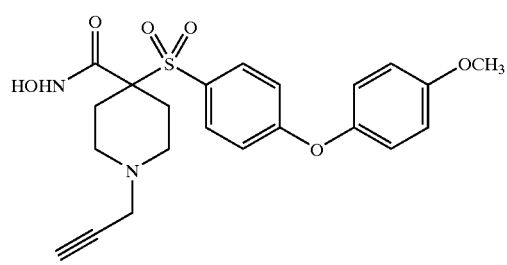

M20)

N-hydroxy-4-[[4-(4-methoxyphenoxy)phenyl]sulfonyl]-1-(2-propynyl)-4-piperidinecarboxamide;

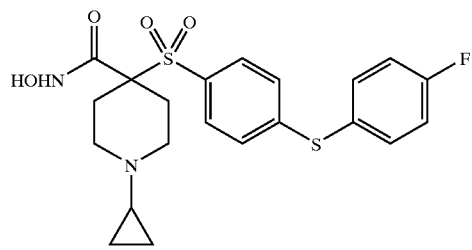

M21)

1-cyclopropyl-4-[[4-[(4-fluorophenyl)thio]phenyl]sulfonyl]-N-hydroxy-4-piperidinecarboxamide;

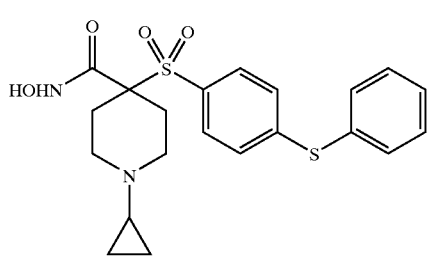

M22)

1-cyclopropyl-N-hydroxy-4-[[4-(phenylthio)phenyl]sulfonyl]-4-piperidinecarboxamide;

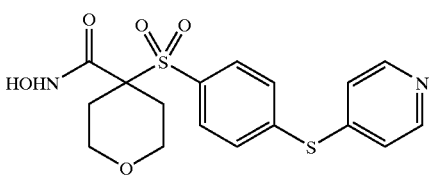

M23)

tetrahydro-N-hydroxy-4-[[4-(4-pyridinylthio)phenyl]sulfonyl]-2H-pyran-4-carboxamide;

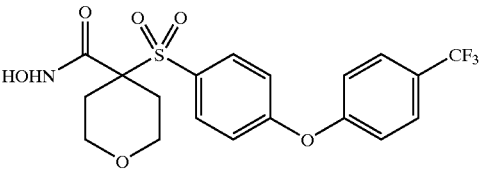

M24)

tetrahydro-N-hydroxy-4-[[4-[4-(trifluoromethyl)phenoxy]phenyl]sulfonyl]-2H-pyran-4-carboxamide.

Still more preferred MMP inhibitors include:

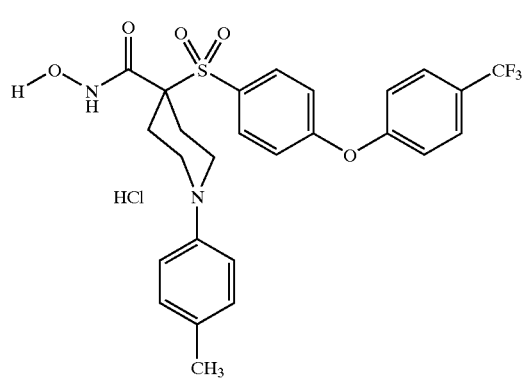

N-hydroxy-1-(4-methylphenyl)-4-[[4-[4-(trifluoromethyl)phenoxy]phenyl]sulfonyl]-4-piperidinecarboxamide monohydrochloride;

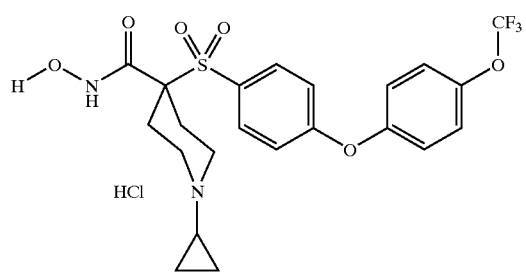

1-cyclopropyl-N-hydroxy-4-[[4-[4-(trifluoromethoxy)phenoxy]phenyl]sulfonyl]-4-piperidinecarboxamide monohydrochloride;

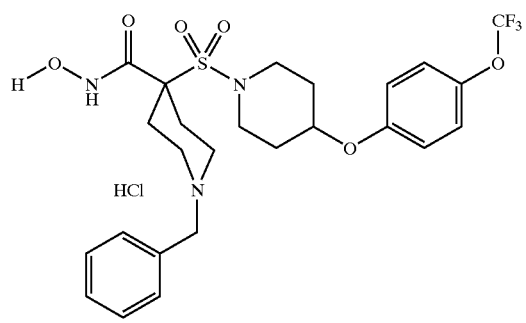

N-hydroxy-1-(phenylmethyl)-4-[[4-[4-(trifluoromethoxy)phenoxy]-1-piperidinyl]sulfonyl]-4-piperidinecarboxamide monohydrochloride;

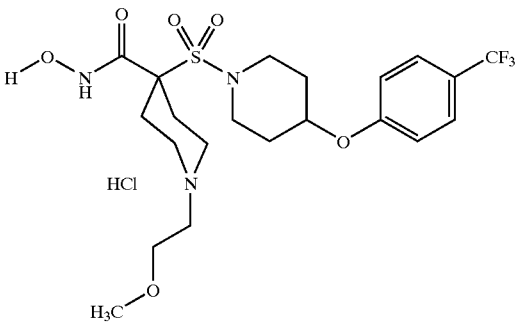

N-hydroxy-1-(4-pyridinylmethyl)-4-[[4-[4-(trifluoromethyl)phenoxy]phenyl]sulfonyl]-4-piperidinecarboxamide dihydrochloride;

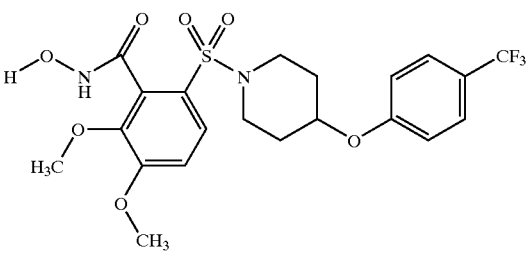

N-hydroxy-2,3-dimethoxy-6-[[4-[4-(trifluoromethyl)phenoxy]-1-piperidinyl]sulfonyl]benzamide;

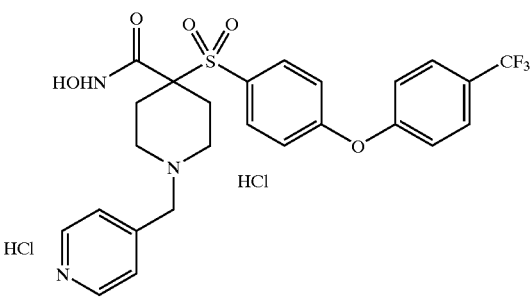

N-hydroxy-1-(4-pyridinylmethyl)-4-[[4-[4-(trifluoromethyl)phenoxy]phenyl]sulfonyl]-4-piperidinecarboxamide dihydrochloride;

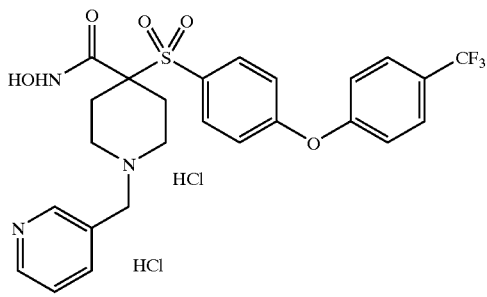

N-hydroxy-1-(3-pyridinylmethyl)-4-[[4-[4-(trifluoromethyl)phenoxy]phenyl]sulfonyl]-4-piperidinecarboxamide dihydrochloride;

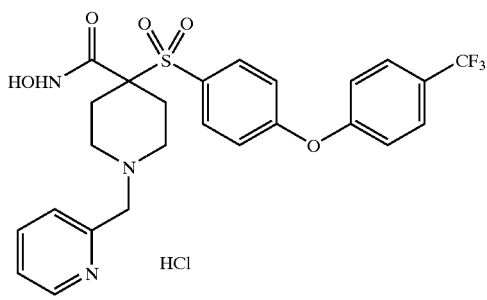

N-hydroxy-1-(2-pyridinylmethyl)-4-[[4-[4-(trifluoromethyl)phenoxy]phenyl]sulfonyl]-4-piperidinecarboxamide monohydrochloride;

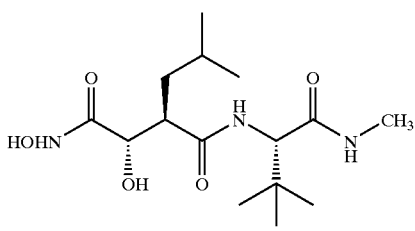

British Biotech BB-2516 (Marimastat), N4-[2,2-dimethyl-1-[(methylamino)carbonyl]propyl]-N1,2-dihydroxy-3-(2-methylpropyl)-, [2S-[N4(R*),2R*,3S*]]-);

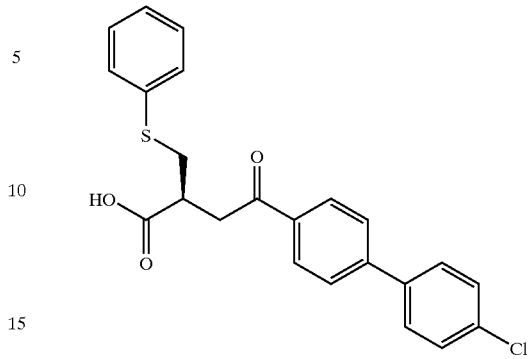

Bayer Ag Bay-12-9566, 4-[(4'-chloro[1,1'-iphenyl]-4-yl)oxy]-2-[(phenylthio)methyl]butanoic acid;

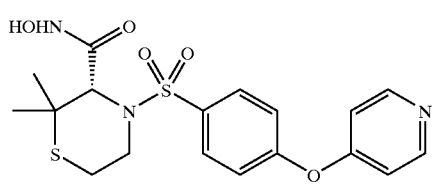

Agouron Pharmaceuticals AG-3340, N-hydroxy-2,2-dimethyl-4-[[4-(4-pyridinyloxy)phenyl]sulfonyl]-3-thiomorpholinecarboxamide;
M12) CollaGenex Pharmaceuticals CMT-3 (Metastat), 6-demethyl-6-deoxy-4-dedimethylaminotetracycline;
M13) Chiroscience D-2163, 2-[1S-([(2R,S)-acetylmercapto-5-phthalimido]pentanoyl-L-leucyl)amino-3-methylbutyl] imidazole.

Also included in the combination of the invention are the isomeric forms and tautomers of the described compounds and the pharmaceutically-acceptable salts thereof. Illustrative pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, b-hydroxybutyric, galactaric and galacturonic acids.

Suitable pharmaceutically-acceptable base addition salts of compounds of the present invention include metallic ion salts and organic ion salts. More preferred metallic ion salts include, but are not limited to appropriate alkali metal (group Ia) salts, alkaline earth metal (group IIa) salts and other physiological acceptable metal ions. Such salts can be made from the ions of aluminum, calcium, lithium, magnesium, potassium, sodium and zinc. Preferred organic salts can be made from tertiary amines and quaternary ammonium salts, including in part, trimethylamine, diethylamine, N,N'-dibenzylethylenediamine, chloroprocaine, choline, diethanolamine, ethylenediamine, meglumine (N-methylglucamine) and procaine. All of the above salts can be prepared by those skilled in the art by conventional means from the corresponding compound of the present invention.

A MMP inhibitor of the present invention can be formulated as a pharmaceutical composition. Such a composition can then be administered orally, parenterally, by inhalation spray, rectally, or topically in dosage unit formulations containing conventional nontoxic pharmaceutically acceptable carriers, adjuvants, and vehicles as desired. Topical administration can also involve the use of transdermal administration such as transdermal patches or iontophoresis devices. The term parenteral as used herein includes subcutaneous injections, intravenous, intramuscular, intrasternal injection, or infusion techniques. Formulation of drugs is discussed in, for example, Hoover, John E., *Remington's Pharmaceutical Sciences*, Mack Publishing Co., Easton, Pa. 1975. Another discussion of drug formulations can be found in Liberman, H. A. and Lachman, L., Eds., *Pharmaceutical Dosage Forms*, Marcel Decker, New York, N.Y., 1980.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful.

Suppositories for rectal administration of the drug can be prepared by mixing the drug with a suitable nonirritating excipient such as cocoa butter, synthetic mono- di- or triglycerides, fatty acids and polyethylene glycols that are solid at ordinary temperatures but liquid at the rectal temperature and will therefore melt in the rectum and release the drug.

Solid dosage forms for oral administration can include capsules, tablets, pills, powders, and granules. In such solid dosage forms, the compounds of this invention are ordinarily combined with one or more adjuvants appropriate to the indicated route of administration. If administered per os, a contemplated aromatic sulfone hydroximate inhibitor compound can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. A contemplated MMP inhibitor compound can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredient that can be combined with the carrier materials to produce a single dosage form varies depending upon the mammalian host treated and the particular mode of administration.

Dosage of MMP Inhibitors

Dosage levels of MMP inhibitors on the order of about 0.1 mg to about 10,000 mg of the active ingredient compound are useful in the treatment of the above conditions, with preferred levels of about 1.0 mg to about 1,000 mg. The amount of active ingredient that may be combined with other anticancer agents to produce a single dosage form will vary depending upon the host treated and the particular mode of administration.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration.

Treatment dosages generally may be titrated to optimize safety and efficacy. Typically, dosage-effect relationships from in vitro initially can provide useful guidance on the proper doses for patient administration. Studies in animal models also generally may be used for guidance regarding effective dosages for treatment of cancers in accordance with the present invention. In terms of treatment protocols, it should be appreciated that the dosage to be administered will depend on several factors, including the particular agent that is administered, the route administered, the condition of the particular patient, etc. Generally speaking, one will desire to administer an amount of the compound that is effective to achieve a serum level commensurate with the concentrations found to be effective in vitro. Thus, where an compound is found to demonstrate in vitro activity at, e.g., 10 $\mu$M, one will desire to administer an amount of the drug that is effective to provide about a 10 $\mu$M concentration in vivo. Determination of these parameters are well within the skill of the art.

These considerations, as well as effective formulations and administration procedures are well known in the art and are described in standard textbooks.

The phrase "antineoplastic agents" includes agents that exert antineoplastic effects, i.e., prevent the development, maturation, or spread of neoplastic cells, directly on the tumor cell, e.g., by cytostatic or cytocidal effects, and not indirectly through mechanisms such as biological response modification. There are large numbers of antineoplastic agents available in commercial use, in clinical evaluation and in pre-clinical development, which could be included in the present invention for treatment of neoplasia by combination drug chemotherapy. For convenience of discussion, antineoplastic agents are classified into the following classes, subtypes and species:

ACE inhibitors,
alkylating agents,
angiogenesis inhibitors,
angiostatin,
anthracyclines/DNA intercalators,
anti-cancer antibiotics or antibiotic-type agents,
antimetabolites,
antimetastatic compounds,
asparaginases,
bisphosphonates,
cGMP phosphodiesterase inhibitors,
calcium carbonate,
cyclooxygenase-2 inhibitors
DHA derivatives,
DNA topoisomerase,
endostatin,
epipodophylotoxins,
genistein,
hormonal anticancer agents,
hydrophilic bile acids (URSO),
immunomodulators or immunological agents,
integrin antagonists
interferon antagonists or agents,
MMP inhibitors,
miscellaneous antineoplastic agents,
monoclonal antibodies,
nitrosoureas,
NSAIDs,
ornithine decarboxylase inhibitors,
pBATTs,
radio/chemo sensitizers/protectors,
retinoids
selective inhibitors of proliferation and migration of endotheliai cells,
selenium,
stromelysin inhibitors,
taxanes,
vaccines, and
vinca alkaloids.

The major categories that some preferred antineoplastic agents fall into include antimetabolite agents, alkylating agents, antibiotic-type agents, hormonal anticancer agents, immunological agents, interferon-type agents, and a category of miscellaneous antineoplastic agents. Some antineoplastic agents operate through multiple or unknown mechanisms and can thus be classified into more than one category.

A first family of antineoplastic agents which may be used in combination with the present invention consists of antimetabolite-type antineoplastic agents. Antimetabolites are typically reversible or irreversible enzyme inhibitors, or compounds that otherwise interfere with the replication, translation or transcription of nucleic acids. Suitable antimetabolite antineoplastic agents that may be used in the present invention include, but are not limited to acanthifolic acid, aminothiadiazole, anastrozole, bicalutamide, brequinar sodium, capecitabine, carmofur, Ciba-Geigy CGP-30694, cladribine, cyclopentyl cytosine, cytarabine phosphate stearate, cytarabine conjugates, cytarabine ocfosfate, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, finasteride, floxuridine, fludarabine phosphate, N-(2'-furanidyl)-5-fluorouracil, Daiichi Seiyaku FO-152, fluorouracil (5-FU), 5-FU-fibrinogen, isopropyl pyrrolizine, Lilly LY-188011, Lilly LY-264618, methobenzaprim, methotrexate, Wellcome MZPES, nafarelin, norspermidine, nolvadex, NCI NSC-127716, NCI NSC-264880, NCI NSC-39661, NCI NSC-612567, Warner-Lambert PALA, pentostatin, piritrexim, plicamycin, Asahi Chemical PL-AC, stearate; Takeda TAC-788, thioguanine, tiazofurin, Erbamont TIF, trimetrexate, tyrosine kinase inhibitors, tyrosine protein kinase inhibitors, Taiho UFT, toremifene, and uricytin.

Preferred antimetabolite agents that may be used in the present invention include, but are not limited to, those identified in Table No. 5, below.

TABLE No. 5

Antimetabolite agents

| Compound | Common Name/ Trade Name | Company | Reference | Dosage |
|---|---|---|---|---|
| 1,3-Benzenediacetonitrile, alpha, alpha, alpha', alpha'-tetramethyl-5-(1H-1,2,4-triazol-1-yl-methyl)- | anastrozole; ARIMIDEX ® | Zeneca | EP 296749 | 1-mg/day |
| Propanamide, N-[4-cyano-3-(trifluoromethyl) phenyl)-3-[(4-fluorophenyl) sulfonyl]-2-hydroxy-2-methyl-, (+/−)- | bicalutamide; CASODEX ® | Zeneca | EP 100172 | 50 mg once daily |
|  | capecitabine | Roche | U.S. Pat. No. 5472949 |  |

TABLE No. 5-continued

Antimetabolite agents

| Compound | Common Name/ Trade Name | Company | Reference | Dosage |
|---|---|---|---|---|
| Adenosine, 2-chloro-2'-deoxy-; 2-chloro-2'-deoxy-(beta)-D-adenosine) | cladribine; 2-CdA; LEUSTAT; LEUSTA-TIN ® LEUSTA-TIN ® in-jection; LEUSTATINE ®; RWJ-26251; | Johnson & Johnson | EP 173059 | 0.09 mg/kg/ day for 7 days. |
| 2(1H)-Pyrimidione, 4-amino-1-[5-O-[hydroxy(octa-decyloxy)phos-phinyl]-beta-D-arabinofuran-osyl]-monosodium salt | cytarabine ocfosfate; ara CMP stearyl ester; C-18-PCA; cytarabine phosphate stearate; Starasid; YNK-O1; CYTOSAR-U ® | Yamasa Corp | EP 239015 | 100–300 mg/day for 2 weeks |
| 4-Azaandrost-1-ene-17-carboxamide, N-(1,1-diethylethyl)-3-oxo-(5alpha, 17beta)- | finasteride; PROPECIA ® | Merck & Co | EP 155096 | |
| | fluorouracil (5-FU) | | U.S. Pat. No. 4336381 | |
| Fludarabine phosphate. 9H-Purin-6-amine, 2-fluoro-9-(5-O-phosphono-beta-D-arabinofuran-osyl) | fludarabine phosphate; 2-F-araAMP; Fludara; Fludara iv; Fludara Oral; NSC-312887; SH-573; SH-584; SH-586; | Southern Research Institute; Berlex | U.S. Pat. No. 4357324 | 25 mg/ m²/d IV over a period of approxi-mately 30 minutes daily for 5 consec-utive days com-menced every 28 days. |
| | gemcit-abine | Eli Lily | U.S. Pat. No. 4526988 | |
| N-(4-(((2,4-diamino-6-pteridinyl) methyl)methyl-amino)benzoyl)-L-glutamic acid | methotrexate iv, Hyal; HA + methotrexate, Hyal; methotrexate iv, HIT Technolog; | Hyal Pharma-ceutical; American Home Products; Lederle | U.S. Pat. No. 2512572 | tropho-blastic diseases: 15 to 30 mg/d orally or intra-muscularly in a five-day course (repeated 3 to 5 times as needed) |

TABLE No. 5-continued

Antimetabolite agents

| Compound | Common Name/ Trade Name | Company | Reference | Dosage |
|---|---|---|---|---|
| Luteinizing hormone-releasing factor (pig), 6-[3-(2-napthalenyl)-D-alanine]- | nafarelin | Roche | EP 21234 | |
| | pentostatin; CI-825; DCF; deoxycoformycin; Nipent; NSC-218321; Oncopent; | Warner-Lambert | U.S. Pat. No. 3923785 | |
| Ethanamine, 2-[4-(4-chloro-1,2-diphenyl-1-butenyl)phenoxy]-N,N-dimethyl-(Z)- | toremifene; FARESTON ® | Orion Pharma | EP 95875 | 60 mg/d |

A second family of antineoplastic agents which may be used in combination with the present invention consists of alkylating-type antineoplastic agents. The alkylating agents are believed to act by alkylating and cross-linking guanine and possibly other bases in DNA, arresting cell division. Typical alkylating agents include nitrogen mustards, ethyleneimine compounds, alkyl sulfates, cisplatin, and various nitrosoureas. A disadvantage with these compounds is that they not only attack malignant cells, but also other cells which are naturally dividing, such as those of bone marrow, skin, gastro-intestinal mucosa, and fetal tissue. Suitable alkylating-type antineoplastic agents that may be used in the present invention include, but are not limited to, Shionogi 254-S, aldo-phosphamide analogues, altretamine, anaxirone, Boehringer Mannheim BBR-2207, bestrabucil, budotitane, Wakunaga CA-102, carboplatin, carmustine (BiCNU), Chinoin-139, Chinoin-153, chlorambucil, cisplatin, cyclophosphamide, American Cyanamid CL-286558, Sanofi CY-233, cyplatate, dacarbazine, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, etoposide phosphate, fotemustine, Unimed G-6-M, Chinoin GYKI-17230, hepsul-fam, ifosfamide, iproplatin, lomustine, mafosfamide, mitolactol, mycophenolate, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, thiotepa, Yakult Honsha SN-22, spiromus-tine, Tanabe Seiyaku TA-077, tauromustine, temozolomide, teroxirone, tetraplatin and trimelamol.

Preferred alkylating agents that may be used in the present invention include, but are not limited to, those identified in Table No. 6, below.

TABLE No. 6

Alkylating agents

| Compound | Common Name/ Trade Name | Company | Reference | Dosage |
|---|---|---|---|---|
| Platinum, diammine [1,1-cyclo-butanedi-carboxylato (2-)]-, (SP-4-2)- | carboplatin; PARA-PLATIN ® | Johnson Matthey | U.S. Pat. No. 4657927. U.S. Pat. No. 4140707. | 360 mg/ml (squared) I.V. on day 1 every 4 weeks. |
| Carmustine, 1,3-bis (2-chloroethyl)-1-nitro-sourea | BiCNU ® | Ben Venue Laboratories, Inc. | JAMA 1985; 253 (11): 1590–1592. | Preferred: 150 to 200 mg/m² every 6 wks. |
| | etoposide phosphate | Bristol-Myers Squibb | U.S. Pat. No. 4564675 | |
| Platinum, diamminedi-chloro-, (SP-4-2)- | thiotepa cisplatin; PLATINOL-AQ | Bristol-Myers Squibb | U.S. Pat. No. 4177263 | |
| dacarbazine | DTIC Dome | Bayer | | 2 to 4.5 mg/kg/day for 10 days; 250 mg/ square meter body surface/ day I.V. for 5 days every 3 weeks |

TABLE No. 6-continued

Alkylating agents

| Compound | Common Name/ Trade Name | Company | Reference | Dosage |
|---|---|---|---|---|
| ifosfamide | IFEX | Bristol-Meyers Squibb | | 4–5 g/m (square) single bolus dose, or 1.2–2 g/m (square) I.V. over 5 days. |
| | cyclophosphamide | | U.S. Pat. No. 4537883 | |
| cis-diaminedichloroplatinum | Platinol Cisplatin | Bristol-Myers Squibb | | 20 mg/M$^2$ IV daily for a 5 day cycle. |

A third family of antineoplastic agents which may be used in combination with the present invention consists of antibiotic-type antineoplastic agents. Suitable antibiotic-type antineoplastic agents that may be used in the present invention include, but are not limited to Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

Preferred antibiotic anticancer agents that may be used in the present invention include, but are not limited to, those agents identified in Table No. 7, below.

TABLE No. 7

Antibiotic anticancer agents

| Compound | Common Name/ Trade Name | Company | Reference | Dosage |
|---|---|---|---|---|
| 4-Hexenoic acid, 6-(1,3-dihydro-4-hydroxy-6-methoxy-7-methyl-3-oxo-5-isobenzo-furanyl)-4-methyl-, 2-(4-morpholinyl) ethyl ester, (E)- | mycophenolate mofetil | Roche | WO 91/19498 | 1 to 3 gm/d |
| | mitoxantrone | | U.S. Pat. No. 4310666 | |
| | doxorubicin | | U.S. Pat. No. 3590028 | |
| Mitomycin and/or mitomycin-C | Mutamycin | Bristol-Myers Squibb Oncology/ Immunology | | After full hematological recovery from any previous chemotherapy: 20 mg/m$^2$ intravenously as a single dose via a functioning intravenous catheter. |

A fourth family of antineoplastic agents which may be used in combination with the present invention consists of synthetic nucleosides. Several synthetic nucleosides have been identified that exhibit anticancer activity. A well known nucleoside derivative with strong anticancer activity is 5-fluorouracil (5-FU). 5-Fluorouracil has been used clinically in the treatment of malignant tumors, including, for example, carcinomas, sarcomas, skin cancer, cancer of the digestive organs, and breast cancer. 5-Fluorouracil, however, causes serious adverse reactions such as nausea, alopecia, diarrhea, stomatitis, leukocytic thrombocytopenia, anorexia, pigmentation, and edema. Derivatives of 5-fluorouracil with anti-cancer activity have been described in U.S. Pat. No. 4,336,381. Further 5-FU derivatives have been described in the following patents listed in Table No. 8, hereby individually incorporated by reference herein.

TABLE No. 8

5-Fu derivatives

| | | |
|---|---|---|
| JP 50-50383 | JP 50-50384 | JP 50-64281 |
| JP 51-146482 | JP 53-84981 | |

U.S. Pat. No. 4,000,137 discloses that the peroxidate oxidation product of inosine, adenosine, or cytidine with methanol or ethanol has activity against lymphocytic leukemia. Cytosine arabinoside (also referred to as Cytarabin, araC, and Cytosar) is a nucleoside analog of deoxycytidine that was first synthesized in 1950 and introduced into clinical medicine in 1963. It is currently an important drug in the treatment of acute myeloid leukemia. It is also active against acute lymphocytic leukemia, and to a lesser extent, is useful in chronic myelocytic leukemia and non-Hodgkin's lymphoma. The primary action of araC is inhibition of nuclear DNA synthesis. Handschumacher, R. and Cheng, Y., "Purine and Pyrimidine Antimetabolites", Cancer Medicine, Chapter XV-1, 3rd Edition, Edited by J. Holland, et al., Lea and Febigol, publishers.

5-Azacytidine is a cytidine analog that is primarily used in the treatment of acute myelocytic leukemia and myelodysplastic syndrome.

2-Fluoroadenosine-5'-phosphate (Fludara, also referred to as FaraA) is one of the most active agents in the treatment of chronic lymphocytic leukemia. The compound acts by inhibiting DNA synthesis. Treatment of cells with F-araA is associated with the accumulation of cells at the G1/S phase boundary and in S phase; thus, it is a cell cycle S phase-specific drug. InCorp of the active metabolite, F-araATP, retards DNA chain elongation. F-araA is also a potent inhibitor of ribonucleotide reductase, the key enzyme responsible for the formation of DATP. 2-Chlorodeoxyadenosine is useful in the treatment of low grade B-cell neoplasms such as chronic lymphocytic leukemia, non-Hodgkins' lymphoma, and hairy-cell leukemia. The spectrum of activity is similar to that of Fludara. The compound inhibits DNA synthesis in growing cells and inhibits DNA repair in resting cells.

A fifth family of antineoplastic agents which may be used in combination with the present invention consists of hormonal agents. Suitable hormonal-type antineoplastic agents that may be used in the present invention include, but are not limited to Abarelix; Abbott A-84861; Abiraterone acetate; Aminoglutethimide; anastrozole; Asta Medica AN-207; Antide; Chugai AG-041R; Avorelin; aseranox; Sensus B2036-PEG; Bicalutamide; buserelin; BTG CB-7598; BTG CB-7630; Casodex; cetrolix; clastroban; clodronate disodium; Cosudex; Rotta Research CR-1505; cytadren; crinone; deslorelin; droloxifene; dutasteride; Elimina; Laval University EM-800; Laval University EM-652; epitiostanol; epristeride; Mediolanum EP-23904; EntreMed 2-ME; exemestane; fadrozole; finasteride; flutamide; formestane; Pharmacia & Upjohn FCE-24304; ganirelix; goserelin; Shire gonadorelin agonist; Glaxo Wellcome GW-5638; Hoechst Marion Roussel Hoe-766; NCI hCG; idoxifene; isocordoin; Zeneca ICI-182780; Zeneca ICI-118630; Tulane University J015X; Schering Ag J96; ketanserin; lanreotide; Milkhaus LDI-200; letrozol; leuprolide; leuprorelin; liarozole; lisuride hydrogen maleate; loxiglumide; mepitiostane; Leuprorelin; Ligand Pharmaceuticals LG-1127; LG-1447; LG-2293; LG-2527; LG-2716; Bone Care International LR-103; Lilly LY-326315; Lilly LY-353381-HCl; Lilly LY-326391; Lilly LY-353381; Lilly LY-357489; miproxifene phosphate; Orion Pharma MPV-2213ad; Tulane University MZ-4-71; nafarelin; nilutamide; Snow Brand NKS01; octreotide; Azko Nobel ORG-31710; Azko Nobel ORG-31806; orimeten; orimetene; orimetine; ormeloxifene; osaterone; Smithkline Beecham SKB-105657; Tokyo University OSW-1; Peptech PTL-03001; Pharmacia & Upjohn PNU-156765; quinagolide; ramorelix; Raloxifene; statin; sandostatin LAR; Shionogi S-10364; Novartis SMT-487; somavert; somatostatin; tamoxifen; tamoxifen methiodide; teverelix; toremifene; triptorelin; TT-232; vapreotide; vorozole; Yamanouchi YM-116; Yamanouchi YM-511; Yamanouchi YM-55208; Yamanouchi YM-53789; Schering AG ZK-1911703; Schering AG ZK-230211; and Zeneca ZD-182780.

Preferred hormonal agents that may be used in the present invention include, but are not limited to, those identified in Table No. 9, below.

TABLE 9

Hormonal agents

| Compound | Common Name/ Trade Name | Company | Reference | Dosage |
|---|---|---|---|---|
| 2-methoxyestradiol | EntreMed; 2-Me | EntreMed | | |
| N-(S)-tetrahydrofuroyl-Gly-D2Nal-D4ClPhe-D3Pal-Ser-NMeTyr-DLys(Nic)-Leu-Lys(Isp)-Pro-DAla-NH2 | A-84861 | Abbott | | |
| | raloxifene | | | |
| [3R-1-(2,2-Dimethoxyethyl)-3-((4-methylphenyl)aminocarbonyl-methyl)-3-(N'-(4-methylphenyl)ureido)-indoline-2-one] | AG-041R | Chugai | WO 94/19322 | |
| | AN-207 | Asta Medica | WO 97/19954 | |
| Ethanamine, 2-[4-(4-chloro-1,2-diphenyl-1-butenyl)phenoxy]-N,N-dimethyl-,(Z)- | toremifene; FARESTON ® | Orion Pharma | EP 95875 | 60 mg/d |
| Ethanamine, 2-[4-(1,2-diphenyl-1-butenyl)phenoxy]-N,N-dimethyl-,(Z)- | tamoxifen NOLVADEX(R) | Zeneca | US 4536516 | For patients with breast cancer, the recommended daily dose is 20–40 mg. Dosages greater than 20 mg per day should be divided (morning and evening). |
| D-Alaninamide N-acetyl-3-(2-naphthalenyl)-D-alanyl-4-chloro-D-phenylalanyl-3-(3-pyridinyl)-D-alanyl-L-seryl-N6-(3-pyridinylcarbonyl)-L-lysyl-N6-(3-pyridinyl-carbonyl)-D-lysyl-L-leucyl-N6-(1-methylethyl)-L-lysyl-L-prolyl- | Antide; ORF-23541 | Ares-Serono | WO 89/01944 | 25 or 50 microg/kg sc |
| | B2036-PEG; Somaver; Trovert | Senus | | |

TABLE 9-continued

Hormonal agents

| Compound | Common Name/ Trade Name | Company | Reference | Dosage |
|---|---|---|---|---|
| 4-Methyl-2-[4-[2-(1-piperidinyl)ethoxy]phenyl]-7-(pivaloyloxy)-3-[4-(pivaloyloxy)phenyl]-2H-1-benzopyran | EM-800; EM-652 | Laval University | | |
| | letrozol | | US 4749346 | |
| | goserelin | | US 4100274 | |
| 3-[4-[1,2-Diphenyl-1(Z)-butenyl]phenyl]-2(E)-propenoic acid | GW-5638 | Glaxo Wellcome | | |
| Estra-1,3,5(10)-triene-3,17-diol, 7-[9-[(4,4,5,5,5-pentafluoropentyl)sulfinyl]nonyl]-, (7alpha,17beta)- | ICI-182780; Faslodex; ZD-182780 | Zeneca | EP 34/6014 | 250 mg/mth |
| | J015X | Tulane University | | |
| | LG-1127; LG-1447 | Ligand Pharmaceuticals | | |
| | LG-2293 | Ligand Pharmaceuticals | | |
| | LG-2527; LG-2716 | Ligand Pharmaceuticals | | |
| | buserelin, Peptech; deslorelin, Peptech; PTL-03001; triptorelin, Peptech | Peptech | | |
| | LR-103 | Bone Care International | | |
| [2-(4-Hydroxyphenyl)-6-hydroxynaphthalen-1-yl] [4-[2-(1-piperdinyl)ethoxy]phenyl] methane hydrochloride | LY-326315 | Lilly | WO 9609039 | |
| | LY-353381-HCl | Lilly | | |
| | LY-326391 | Lilly | | |
| | LY-353381 | Lilly | | |
| | LY-357489 | Lilly | | |
| | MPV-2213ad | Orion Pharma | EP 476944 | 0.3–300 mg |
| Isobutyryl-Tyr-D-Arg-Asp-Ala-Ile-(4-Cl)-Phe-Thr-Asn-Ser-Tyr-Arg-Lys-Val-Leu-(2-aminobutyryl)-Gln-Leu-Ser-Ala-Arg-Lys-Leu-Leu-Gln-Asp-Ile-Nle-Ser 4-guanidinobutyl-amide | MZ-4-71 | Tulane University | | |
| Androst-4-ene-3,6,17-trione, 14-hydroxy- | NKS01; 14alpha-OHAT; 14OHAT | Snow Brand | EP 300062 | |
| 3beta,16beta,17alpha-trihydroxycholest-5-en-22-one-16-O-(2-0-4-methoxybenzoyl-beta-D-xylopyranosyl)-(1-3) (2-0-acetyl-alpha-L-arabinopyranoside) | OSW-1 | | | |
| Spiro[estra-4,9-diene-17,2'(3'H)-furan]-3-one, 11-[4-(dimethylamino)phenyl]-4',5'-dihydro-6-methyl-, (6beta,11beta,17beta)- | Org-31710; Org-31806 | Akzo Nobel | EP 289073 | |
| (22RS)-N-(1,1,1-trifluoro-2-phenylprop-2-yl)-3-oxo-4-aza-5alpha-androst-1-ene-17beta-carboxamide | PNU-156765; FCE-28260 | Pharmacia & Upjohn | | |
| 1-[(benzofuran-2yl)-4-chlorophenylmethyl]imidazole | | Menarini | | |
| Tryptamine derivatives | | Rhone-Poulenc Rorer | WO 96/35686 | |
| Permanently ionic derivatives of steroid hormones and their antagonists | | Pharmos | WO 95/26720 | |
| Novel tetrahydronaphthofuranone derivatives | | Meiji Seika | WO 97/30040 | |
| | SMT-487; 90Y-octreotide | Novartis | | |
| D-Phe-Cys-Tyr-D-Trp-Lys-Cys-Thr-NH2 | TT-232 | | | |

TABLE 9-continued

Hormonal agents

| Compound | Common Name/ Trade Name | Company | Reference | Dosage |
|---|---|---|---|---|
| 2-(1H-imidazol-4-ylmethyl)-9H-carbazole monohydrochloride monohydrate | YM-116 | Yamanouchi | | |
| 4-[N-(4-bromobenzyl)-N-(4-cyanophenyl) amino]-4H-1,2,4-triazole | YM-511 | Yamanouchi | | |
| 2-(1H-imidazol-4-ylmethyl)-9H-carbazole monohydrochloride monohydrate | YM-55208; YM-53789 | Yamanouchi | | |
| | ZK-1911703 ZK-230211 abarelix | Schering AG Schering AG Praecis Pharmaceuticals | | |
| Androsta-5,16-dien-3-ol, 17-(3-pyridinyl)-, acetate (ester), (3beta)- | abiraterone acetate; CB-7598; CB-7630 | BTG | | |
| 2,6-Piperidinedione, 3-(4-aminophenyl)-3-ethyl- | aminoglutethimide; Ciba-16038; Cytadren; Elimina; Orimeten; Orimetene; Orimetine | Novartis | US 3944671 | |
| 1,3-Benzenediacetonitrile,alpha,alpha,alpha',alpha'-tetramethyl-5-(1H-1,2,4-triazol-1-ylmethyl)- | anastrozole; Arimidex; ICI-D1033; ZD-1033 | Zeneca | EP 296749 | 1 mg/day |
| 5-Oxo-L-prolyl-L-histidyl-L-tryptophyl-L-seryl-L-tyrosyl-2-methyl-D-tryptophyl-L-leucyl-L-arginyl-N-ethyl-L-prolinamide | avorelin; Meterelin | Mediolanum | EP 23904 | |
| Propanamide, N-[4-cyano-3-(trifluoromethyl)phenyl]-3-[(4-fluorophenyl)sulfonyl]-2-hydroxy-2-methyl-, (+/−)- | bicalutamide; Casodex; Cosudex; ICI-176334 | Zeneca | EP 100172 | |
| Luteinizing hormone-releasing factor (pig), 6-[O-(1,1-dimethylethyl)-D-serine]-9-(N-ethyl-L-prolinamide)-10-deglycinamide- | buserelin; Hoe-766; Profact; Receptal; S-746766; Suprecor; Suprecur; Suprefact; Suprefakt | Hoechst Marion Roussel | GB 15/23623 | 200–600 microg/day |
| D-Alaninamide, N-acetyl-3-(2-naphthalenyl)-D-alanyl-4-chloro-D-phenylalanyl-3-(3-pyridinyl)-D-alanyl-L-seryl-L-tyrosyl-N5-(aminocarbonyl)-D-ol-L-leucyl-L-arginyl-L-prolyl- | cetrorelix; SB-075; SB-75 | Asta Medica | EP 29/9402 | |
| Phosphonic acid, (dichloromethylene) bis-, disodium salt- | clodronate disodium, Leiras; Bonefos; Clastoban; KCO-692 | Schering AG | | |
| Luteninizing hormone-releasing factor (pig), 6-D-tryptophan-9-(N-ethyl-L-prolinamide)-10-deglycinamide- | deslorelin; gonadorelin analogue, Roberts; LHRH analogue, Roberts; Somagard | Roberts | US 4034082 | |
| Phenol, 3-[1-[4-[2-(dimethylamino)ethoxy]phenyl]-2-phenyl-1-butenyl]-, (E)-[CA S] | droloxifene; FK-435; K-060; K-21060E; RP 60850 | Klinge | EP 54168 | |
| 4-Azaandrost-1-ene-17-carboxamide, N-(2,5-bis(trifluoromethyl)phenyl)-3-oxo-, (5alpha, 17beta)- | dutasteride; GG-745; GI-198745 | Glaxo Wellcome | | |
| Androstan-17-ol, 2,3-epithio-, (2alpha,3alpha,5alpha,17beta)- | epitiostanol; 10275-S; epithiondrostanol; S-10275; Thiobrestin; Thiodrol | Shionogi | US 3230215 | |
| Androsta-3,5-diene-3-carboxylic acid, 17-(((1,1-dimethylethyl)amino)carbonyl)-(17beta)- estrone 3-O-sulfamate | epristeride; ONO-9302; SK&F-105657; SKB-105657 estrone 3-O-sulfamate | Smith-Kline Beecham | EP 289327 | 0.4–160 mg/day |

TABLE 9-continued

Hormonal agents

| Compound | Common Name/ Trade Name | Company | Reference | Dosage |
|---|---|---|---|---|
| 19-Norpregna-1,3,5(10)-trien-20-yne-3,17-diol, 3-(2-propanesulfonate), (17alpha)- | ethinyl estradiol sulfonate; J96; Turisteron | Schering AG | DE 1949095 | |
| Androsta-1,4-diene-3,17-dione, 6-methylene | exemestane; FCE-24304 | Pharmacia & Upjohn | DE 3622841 | 5 mg/kg |
| Benzonitrile, 4-(5,6,7,8-tetrahydroimidazo[1,5-a]pyridin-5-yl)-, monohydrochloride | fadrozole; Afema; Arensin; CGS-16949; CGS-16949A; CGS-20287; fadrozole monohydrochloride | Novartis | EP 165904 | 1 mg po bid |
| 4-Azaandrost-1-ene-17-carboxamide, N-(1,1-dimethylethyl)-3-oxo-, (5alpha,17beta)- | finasteride; Andozac; ChibroProscar; Finastid; MK-0906; MK-906; Procure; Prodel; Propecia; Proscar; Proskar; Prostide; YM-152 | Merck & Co | EP 155096 | 5 mg/day |
| Propanamide, 2-methyl-N-[4-nitro-3-(trifluoromethyl)phenyl]- | Flutamide; Drogenil; Euflex; Eulexin; Eulexine; Flucinom; Flutamida; Fugerel; NK-601; Odyne; Prostogenat; Sch-13521 | Schering Plough | US 4329364 | |
| Androst-4-ene-3,17-dione, 4-hydroxy- | formestane; 4-Had; 4-OHA; CGP-32349; CRC-82/01; Depot; Lentaron | Novartis | EP 346953 | 250 or 600 mg/day po |
| [N-Ac-D-Nal,D-pCl-Phe,D-Pal,D-hArg(Et)2,hArg(Et)2,D-Ala]GnRH- | ganirelix; Org-37462; RS-26306 | Roche | EP 312052 | |
| | gonadorelin agonist, Shire | Shire | | |
| Luteinizing hormone-releasing factor (pig), 6-[O-(1,1-dimethylethyl)-D-serine]-10-deglycinamide-, 2-(aminocarbonyl)hydrazide | goserelin; ICI-118630; Zoladex; Zoladex LA | Zeneca | US 4100274 | |
| | hCG; gonadotrophin; LDI-200 | Milkhaus | | |
| | human chorionic gonadotrophin; hCG | NIH | | |
| Pyrrolidine, 1-[2-[4-[1-(4-iodophenyl)-2-phenyl-1-butenyl]phenoxy]ethyl]-, (E)- | idoxifene; CB-7386; CB-7432; SB-223030 | BTG | EP 260066 | |
| 2,4(1H,3H)-Quinazolinedione, 3-[2-[4-(4-fluorobenzoyl)-1-piperidinyl]ethyl]- | isocordoin ketanserin; Aseranox; Ketensin; KJK-945; ketanserine; Perketan; R-41468; Serefrex; Serepress; Sufrexal; Taseron | Indena Johnson & Johnson | EP 13612 | |
| L-Threoninamide, 3-(2-naphthalenyl)-D-alanyl-L-cysteinyl-L-tyrosyl-D-tryptophyl-L-lysyl-L-valyl-L-cysteinyl-, cyclic (2-7)-disulfide | lanreotide; Angiopeptin; BIM-23014; Dermopeptin; Ipstyl; Somatuline; Somatuline LP | Beaufour-Ipsen | EP 215171 | |
| Benzonitrile, 4,4'-(1H-1,2,4-triazol-1-ylmethylene)bis- | letrozole; CGS-20267; Femara | Novartis | EP 236940 | 2.5 mg/day |
| Luteinizing hormone-releasing factor (pig), 6-D-leucine-9-(N-ethyl-L-prolinamide)-10-deglycinamide- | leuprolide, Atrigel; leuprolide, Atrix | Atrix | | |
| Luteinizing hormone-releasing factor (pig), 6-D- | Leuprorelin; Abbott-43818; | Abbott | US 4005063 | 3.75 microg sc q 28 days |

TABLE 9-continued

Hormonal agents

| Compound | Common Name/ Trade Name | Company | Reference | Dosage |
|---|---|---|---|---|
| leucine-9-(N-ethyl-L-prolinamide)-10-deglycinamide- | Carcinil Enantone; Leuplin; Lucrin; Lupron; Lupron Depot; leuprolide, Abbott; leuprolide, Takeda; leuprorelin, Takeda; Procren Depot; Procrin; Prostap; Prostap SR; TAP-144-SR | | | |
| Luteinizing hormone-releasing factor (pig), 6-D-leucine-9-(N-ethyl-L-prolinamide)-10-deglycinamide- | leuprore-lin, DUROS; leuprolide, DUROS; leuprore-lin | Alza | | |
| 1H-Benzimidazole, 5-[(3-chlorophenyl)-1H-imidazol-1-ylmethyl]- | liaro-zole; Liazal; Liazol; liarozole fumarate; R-75251; R-85246; Ro-85264 | Johnson & Johnson | EP 260744 | 300 mg bid |
| Urea, N'-[(8alpha)-9,10-didehydro-6-methylergolin-8-yl]-N,N-diethyl-, (Z)-2-butenedioate (1:1) | lisuride hydrogen maleate; Cuvalit; Dopergin; Dopergine; Eunal; Lysenyl; Lysenyl Forte; Revanil | VUFB | | |
| Pentanoic acid, 4-[(3,4-dichlorobenzoyl) amino]-5-[(3-methoxypropyl) pentylamino]-5-oxo-, (+/-)- | loxiglumide; CR-1505 | Rotta Research | WO 87/03869 | |
| Androstane, 2,3-epithio-17-[(1-methoxycyclopentyl)oxy]-, (2alpha,3alpha,5alpha,17beta)- | mepitiostane; S-10364; Thioderon | Shionogi | US 3567713 | |
| Phenol, 4-[1-[4-[2- | miproxifene phosphate; | Taiho | WO 87/07609 | 20 mg/day |
| (dimethylamino) ethoxy]phenyl]-2-[4-(1-methylethyl) phenyl]-1-butenyl]-, dihydrogen phosphate (ester), (E)- | DP-TAT-59; TAT-59 | | | |
| Luteinizing hormone-releasing factor (pig), 6-[3-(2-naphthalenyl)-D-alanine]- | nafarelin; NAG, Syntex; Nasanyl; RS-94991; RS-94991-298; Synarel; Synarela; Synrelina | Roche | EP 21/234 | |
| 2,4-Imidazolidinedione, 5,5-dimethyl-3-[4-nitro-3-(trifluoromethyl) pheyl]- | nilutamide; Anandron; Nilandron; Notostran; RU-23908 | Hoechst Marion Roussel | US 4472382 | |
| | obesity gene; diabetes gene; leptin | Lilly | WO 96/24670 | |
| L-Cysteinamide, D-phenylalanyl-L-cysteinyl-L-phenylalanyl-D-tryptophyl-L-lysyl-L-threonyl-N-[2-hydroxy-1-(hydroxymethyl) propyl]-, cyclic (2-7)-disulfide, [R-(R*,R*)]- | octreotide; Longastatina; octreotide pamoate; Sandostatin; Stadostatin LAR; Sandostatina; Sandostatine; SMS-201-995 | Novartis | EP 29/579 | |
| Pyrrolidine, 1-[2-(p-(7-methoxy-2,2-dimethyl-3-phenyl-4-chromanyl) phenoxy)ethyl]-, trans- | ormelox-ifene; 6720-CDRI; Centron; Choice-7; centchroman; Saheli | Central Drug Research Inst. | DE 2329201 | |
| 2-Oxapregna-4,6-diene-3,20-dione, 17-(acetyloxy)-6-chloro- | osaterone acetate; Hipros; TZP-4238 | Teikoku Hormone | EP 193871 | |
| Pregn-4-ene-3,20-dione | progesterone; Crinone | Columbia Laboratories | | |
| Sulfamide, N,N-diethyl-N'-(1,2,3,4,4a,5,10,10a-octahydro-6-hydroxy-1-propylbenzo[g] | quinagolide; CV-205-502; Norprolac; SDZ-205-502 | Novartis | EP 77754 | |

TABLE 9-continued

Hormonal agents

| Compound | Common Name/ Trade Name | Company | Reference | Dosage |
|---|---|---|---|---|
| quinolin-3-yl)-, (3alpha,4aalpha, 10abeta)- (+/-)- L-Proline, 1- (N2-(N-(N-(N-(N-(N-(N-acetyl-3-(2-naphthalenyl)-D-alanyl)-4-chloro-D-phenylalanyl)-D-tryptophyl)-L-seryl)-L-tyrosyl)-O-(6-deoxy-alpha-L-mannopyranosyl)-D-seryl)-L-leucyl)-L-arginyl)-, 2-(aminocarbonyl) hydrazide- | ramorelix; Hoe-013; Hoe-013C; Hoe-2013 | Hoechst Marion Roussel | EP 451791 | |
| | somatostatin analogues | Tulane University | | |
| Ethanamine, 2-[4-(1,2-diphenyl-1-butenyl)phenoxy]-N,N-dimethyl-, (Z)- | taxomifen; Ceadan; ICI-46474; Kessar; Nolgen; Nolvadex; Tafoxen; Tamofen; Tamoplex; Tamoxasta; Tamoxen; Tomaxen | Zeneca | US 4536516 | |
| | tamoxifen methiodide | Pharmos | | |
| Ethanamine, 2-[4-(1,2-diphenyl-1-butenyl)phenoxy]-N,N-dimethyl-, (z)- | tamoxifen | Douglas | | |
| D-Alaninamide, N-acetyl-3-(2-naphthalenyl)-D-alanyl-4-chloro-D-phenylalanyl-3-(3-pyridinyl)-D-alanyl-L-seryl-L-tyrosyl-N6-(aminocarbonyl)-D-lysyl-L-leucyl-N6-(1-methylethyl)-L-lysyl-L-prolyl- | teverelix; Antarelix | Asta Medica | | |
| Ethanamine, 2-[4-(4-chloro-1,2-diphenyl-1-butenyl)phenoxy]-N,N-dimethyl-, (Z)- | toremifene; Estrimex Fareston; FC-1157; FC-1157a; NK-622 | Orion Pharma | EP 95875 | 60 mg po |
| Luteinizing hormone-releasing factor (pig), 6-D-tryptophan- | triptorelin; ARVEKAP; AY-25650; BIM-21003; BN-52104; Decapeptyl; WY-42422 | Debio-pharm | US 4010125 | |
| L-Tryptophanamide, D-phenylalanyl-L-cysteinyl-L-tyrosyl-D-tryptophyl-L-lysyl-L-valyl-L-cysteinyl-, cyclic (2-7)-dsulfide- | vapreotide; BMY-41606; Octastatin; RC-160 | Debio-pharm | EP 203031 | 500 microg sc tid |
| 1H-Benzotriazole, 6-[(4-chlorophenyl)-1H-1,2,4-triazol-1-ylmethyl]-1-methyl- | vorozole; R-76713; R-83842; Rivizor | Johnson & Johnson | EP 293978 | 2.5 mg/day |

A sixth family of antineoplastic agents which may be used in combination with the present invention consists of a miscellaneous family of antineoplastic agents including, but not limited to alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, anti-neoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, calcium carbonate, Calcet, Calci-Chew, Calci-Mix, Roxane calcium carbonate tablets, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Cell Pathways CP-461, Yakult Honsha CPT-11, crisnatol, curaderm, cytochalasin B, cytarabine, cytocytin, Merz D-609, DABIS maleate, dacarbazine, datelliptinium, DFMO, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel, Encore Pharmaceuticals E7869, elliprabin, elliptinium acetate, Tsumura EPMTC, ergotamine, etoposide, etretinate, Eulexin®, Cell Pathways Exisulind® (sulindac sulphone or CP-246), fenretinide, Merck Research Labs Finasteride, Florical, Fujisawa FR-57704, gallium nitrate, gemcitabine, genkwadaphnin, Gerimed, Chugai GLA-43, Glaxo GR-63178, grifolan NMF-5N, hexadecylphosphocholine, Green Cross HO-221, homoharringtonine, hydroxyurea, BTG ICRF-187, ilmofosine, irinotecan, isoglutamine, isotretinoin, Otsuka JI-36, Ramot K-477, ketoconazole, Otsuak K-76COONa, Kureha Chemical K-AM, MECT Corp KI-8110, American Cyanamid L-623, leucovorin, levamisole, leukoregulin, lonidamine, Lundbeck LU-23-112, Lilly LY-186641, Materna, NCI (US) MAP, marycin, Merrel Dow MDL-27048, Medco MEDR-340, megestrol, merbarone, merocyanine derivatives, methylanilinoacridine, Molecular Genetics MGI-136, minactivin, mitonafide, mitoquidone, Monocal, mopidamol, motretinide, Zenyaku Kogyo MST-16, Mylanta, N-(retinoyl)amino acids, Nilandron; Nisshin Flour Milling N-021, N-acylated-dehydroalanines, nafazatrom, Taisho NCU-190, Nephro-Calci tablets, nocodazole derivative, Normosang, NCI NSC-145813, NCI NSC-361456, NCI NSC-604782, NCI NSC-95580, octreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, retinoids, Encore Pharmaceuticals R-flurbiprofen, Sandostatin; Sapporo Breweries RBS, restrictin-P, retelliptine, retinoic acid, Rhone-Poulenc RP-49532, Rhone-Poulenc RP-56976, Scherring-Plough SC-57050, Scherring-Plough SC-57068, seienium(selenite and selenomethionine), Smith-Kline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, Sugen SU-101, Sugen SU-5416, Sugen SU-6668, sulindac, sulindac sulfone; superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, Yamanouchi YM-534, Zileuton, ursodeoxycholic acid, and Zanosar.

Preferred miscellaneous agents that may be used in the present invention include, but are not limited to, those identified in Table No. 6, below.

TABLE No. 6

Miscellaneous agents

| Compound | Common Name/ Trade Name | Company | Reference | Dosage |
|---|---|---|---|---|
| Flutamide; 2-methyl-N-(4-nitro-3-(trifluoromethyl)phenyl) propanamide | EULEXIN ® | Schering Corp | | 750 mg/d in 3 8-hr doses. |
| | Ketoconazole | | U.S. Pat. No. 4144346 | |
| | leucovorin | | U.S. Pat. No. 4148999 | |
| | irinotecan | | U.S. Pat. No. 4604463 | |
| | levamisole | | GB 11/20406 | |
| | megestrol | | U.S. Pat. No. 4696949 | |
| | paclitaxel | | U.S. Pat. No. 5641803 | |
| Nilutamide 5,5-dimethyl 3-(4-nitro 3-(trifluoromethyl) phenyl) | Nilandron | Hoechst Marion Roussel | | A total daily dose of 300 mg for 30 days followed |

TABLE No. 6-continued

Miscellaneous agents

| Compound | Common Name/ Trade Name | Company | Reference | Dosage |
|---|---|---|---|---|
| 2,4-imidazolidinedione | | | | thereafter by three tablets (50 mg each) once a day for a total daily dosage of 150 mg. |
| | Vinorelbine vinblastine vincristine | | EP 0010458 | |
| Octreotide acetate L-cysteinamide, D-phenylalanyl-L-cysteinyl-L-phenylalanyl-D-tryptophyl-L-lysyl-L-threonyl-NSAIDs-(2-hydroxy-1 (hydroxymethyl) propyl)-, cyclic-disulfide; (R-(R*,R*) acetate salt | Sandostatin | Sandoz Pharmaceuticals | | s.c. or i.v. administration Acromegaly: 50–300 mcgm tid. Carcinoid tumors: 100–600 mcgm/d (mean = 300 mcgm/d) Vipomas: 200–300 mcgm in first two weeks of therapy |
| Streptozocin Streptozocin 2-deoxy-2-(((methylnitro samino)-carbonyl) amino)-alpha(and beta)-D-glucopyranose) | Zanosar | Pharmacia & Upjohn | | i.v. 1000 mg/M2 of body surface per week for two weeks. |
| | topotecan | | U.S. Pat. No. 5004758 EP 804927 | |
| Selenium L-selenomethionine | ACE ® | J. R. Carlson Laboratories | | |
| calcium carbonate | | | | |
| sulindac sulfone | Exisuland ® | | U.S. Pat. No. 5858694 | |
| ursodeoxycholic acid | | | U.S. Pat. No. 5843929 | |
| | Cell Pathways CP-461 | | | |

Some additional preferred antineoplastic agents include those described in the individual patents listed in Table No. 7 below, and are hereby individually incorporated by reference.

TABLE No. 7

Antineoplastic agents

| | | | |
|---|---|---|---|
| EP 0296749 | EP 0882734 | EP 00253738 | GB 02/135425 |
| WO 09/832762 | EP 0236940 | U.S. Pat. No. 5338732 | U.S. Pat. No. 4418068 |
| U.S. Pat. No. 4692434 | U.S. Pat. No. 5464826 | U.S. Pat. No. 5061793 | EP 0702961 |
| EP 0702961 | EP 0702962 | EP 0095875 | EP 0010458 |
| EP 0321122 | U.S. Pat. No. 5041424 | JP 60019790 | WO 09/512606 |
| U.S. Pat. No. 4,808614 | U.S. Pat. No. 4526988 | CA 2128644 | U.S. Pat. No. 5455270 |
| WO 99/25344 | WO 96/27014 | U.S. Pat. No. 5695966 | DE 19547958 |
| WO 95/16693 | WO 82/03395 | U.S. Pat. No. 5789000 | U.S. Pat. No. 5902610 |
| EP 189990 | U.S. Pat. No. 4500711 | FR 24/74032 | U.S. Pat. No. 5925699 |
| WO 99/25344 | U.S. Pat. No. 4537883 | U.S. Pat. No. 4808614 | U.S. Pat. No. 5464826 |
| U.S. Pat. No. 5366734 | U.S. Pat. No. 4767628 | U.S. Pat. No. 4100274 | U.S. Pat. No. 4584305 |
| U.S. Pat. No. 4336381 | JP 5050383 | JP 5050384 | JP 5064281 |
| JP 51146482 | JP 5384981 | U.S. Pat. No. 5472949 | U.S. Pat. No. 5455270 |
| U.S. Pat. No. 4140704 | U.S. Pat. No. 4537883 | U.S. Pat. No. 4814470 | U.S. Pat. No. 3590028 |
| U.S. Pat. No. 4564675 | U.S. Pat. No. 4526988 | U.S. Pat. No. 4100274 | U.S. Pat. No. 4604463 |
| U.S. Pat. No. 4144346 | U.S. Pat. No. 4749713 | U.S. Pat. No. 4148999 | GB 11/20406 |
| U.S. Pat. No. 4696949 | U.S. Pat. No. 4310666 | U.S. Pat. No. 5641803 | U.S. Pat. No. 4418068 |
| U.S. Pat. No. 5,004758 | EP 0095875 | EP 0010458 | U.S. Pat. No. 4935437 |
| U.S. Pat. No. 4,278689 | U.S. Pat. No. 4820738 | U.S. Pat. No. 4413141 | U.S. Pat. No. 5843917 |
| U.S. Pat. No. 5,858694 | U.S. Pat. No. 4330559 | U.S. Pat. No. 5851537 | U.S. Pat. No. 4499072 |
| U.S. Pat. No. 5,217886 | WO 98/25603 | WO 98/14188 | |

Table No. 8 provides illustrative examples of median dosages for selected cancer agents that may be used in combination with an antiangiogenic agent. It should be noted that specific dose regimen for the chemotherapeutic agents below depends upon dosing considerations based upon a variety of factors including the type of neoplasia; the stage of the neoplasm; the age, weight, sex, and medical condition of the patient; the route of administration; the renal and hepatic function of the patient; and the particular combination employed.

TABLE No. 8

Median dosages for selected cancer agents.

| NAME OF CHEMOTHERAPEUTIC AGENT | MEDIAN DOSAGE |
|---|---|
| Asparaginase | 10,000 units |
| Bleomycin Sulfate | 15 units |
| Carboplatin | 50–450 mg. |
| Carmustine | 100 mg. |
| Cisplatin | 10–50 mg. |
| Cladribine | 10 mg. |
| Cyclophosphamide (lyophilized) | 100 mg.–2 gm. |
| Cyclophosphamide (non-lyophilized) | 100 mg.–2 gm. |
| Cytarabine (lyophilized powder) | 100 mg.–2 gm. |
| Dacarbazine | 100 mg.–200 mg. |
| Dactinomycin | 0.5 mg. |
| Daunorubicin | 20 mg. |
| Diethylstilbestrol | 250 mg. |
| Doxorubicin | 10–150 mg. |
| Etidronate | 300 mg. |
| Etoposide | 100 mg. |
| Floxuridine | 500 mg. |
| Fludarabine Phosphate | 50 mg. |
| Fluorouracil | 500 mg.–5 gm. |
| Goserelin | 3.6 mg. |
| Granisetron Hydrochloride | 1 mg. |
| Idarubicin | 5–10 mg. |
| Ifosfamide | 1–3 gm. |
| Leucovorin Calcium | 50–350 mg. |
| Leuprolide | 3.75–7.5 mg. |
| Mechlorethamine | 10 mg. |
| Medroxyprogesterone | 1 gm. |
| Melphalan | 50 gm. |
| Methotrexate | 20 mg.–1 gm. |

TABLE No. 8-continued

Median dosages for selected cancer agents.

| NAME OF CHEMOTHERAPEUTIC AGENT | MEDIAN DOSAGE |
|---|---|
| Mitomycin | 5–40 mg. |
| Mitoxantrone | 20–30 mg. |
| Ondansetron Hydrochloride | 40 mg. |
| Paclitaxel | 30 mg. |
| Pamidronate Disodium | 30–90 mg. |
| Pegaspargase | 750 units |
| Plicamycin | 2,500 mcgm. |
| Streptozocin | 1 gm. |
| Thiotepa | 15 mg. |
| Teniposide | 50 mg. |
| Vinblastine | 10 mg. |
| Vincristine | 1–5 mg. |
| Aldesleukin | 22 million units |
| Epoetin Alfa | 2,000–10,000 units |
| Filgrastim | 300–480 mcgm. |
| Immune Globulin | 500 mg.–10 gm. |
| Interferon Alpha-2a | 3–36 million units |
| Interferon Alpha-2b | 3–50 million units |
| Levamisole | 50 mg. |
| Octreotide | 1,000–5,000 mcgm. |
| Sargramostim | 250–500 mcgm. |

The anastrozole used in the therapeutic combinations of the present invention can be prepared in the manner set forth in U.S. Pat. No. 4,935,437. The capecitabine used in the therapeutic combinations of the present invention can be prepared in the manner set forth in U.S. Pat. No. 5,472,949. The carboplatin used in the therapeutic combinations of the present invention can be prepared in the manner set forth in U.S. Pat. No. 5,455,270. The Cisplatin used in the therapeutic combinations of the present invention can be prepared in the manner set forth in U.S. Pat. No. 4,140,704. The cyclophoshpamide used in the therapeutic combinations of the present invention can be prepared in the manner set forth in U.S. Pat. No. 4,537,883. The eflornithine (DFMO) used in the therapeutic combinations of the present invention can be prepared in the manner set forth in U.S. Pat. No. 4,413,141. The docetaxel used in the therapeutic combinations of the present invention can be prepared in the manner set forth in U.S. Pat. No. 4,814,470. The doxorubicin used in the therapeutic combinations of the present invention can be prepared in the manner set forth in U.S. Pat. No. 3,590,028. The etoposide used in the therapeutic combinations of the present invention can be prepared in the manner set forth in U.S. Pat. No. 4,564,675. The fluorouricil used in the therapeutic combinations of the present invention can be prepared in the manner set forth in U.S. Pat. No. 4,336,381. The gemcitabine used in the therapeutic combinations of the present invention can be prepared in the manner set forth in U.S. Pat. No. 4,526,988. The goserelin used in the therapeutic combinations of the present invention can be prepared in the manner set forth in U.S. Pat. No. 4,100,274. The irinotecan used in the therapeutic combinations of the present invention can be prepared in the manner set forth in U.S. Pat. No. 4,604,463. The ketoconazole used in the therapeutic combinations of the present invention can be prepared in the manner set forth in U.S. Pat. No. 4,144,346. The letrozole used in the therapeutic combinations of the present invention can be prepared in the manner set forth in U.S. Pat. No. 4,749,713. The leucovorin used in the therapeutic combinations of the present invention can be prepared in the manner set forth in U.S. Pat. No. 4,148,999. The levamisole used in the therapeutic combinations of the present invention can be prepared in the manner set forth in GB 11/20,406. The megestrol used in the therapeutic combinations of the present invention can be prepared in the manner set forth in U.S. Pat. No. 4,696,949. The mitoxantrone used in the therapeutic combinations of the present invention can be prepared in the manner set forth in U.S. Pat. No. 4,310,666. The paclitaxel used in the therapeutic combinations of the present invention can be prepared in the manner set forth in U.S. Pat. No. 5,641,803. The Retinoic acid used in the therapeutic combinations of the present invention can be prepared in the manner set forth in U.S. Pat. No. 4,843,096. The tamoxifen used in the therapeutic combinations of the present invention can be prepared in the manner set forth in U.S. Pat. No. 4,418,068. The topotecan used in the therapeutic combinations of the present invention can be prepared in the manner set forth in U.S. Pat. No. 5,004,758. The toremifene used in the therapeutic combinations of the present invention can be prepared in the manner set forth in EP 00/095,875. The vinorelbine used in the therapeutic combinations of the present invention can be prepared in the manner set forth in EP 00/010,458. The sulindac sulfone used in the therapeutic combinations of the present invention can be prepared in the manner set forth in U.S. Pat. No. 5,858,694. The selenium (selenomethionine) used in the therapeutic combinations of the present invention can be prepared in the manner set forth in EP 08/04,927. The ursodeoxycholic acid used in the therapeutic combinations of the present invention can be prepared in the manner set forth in WO 97/34,608. Ursodeoxycholic acid can also be prepared according to the manner set forth in EP 05/99,282. Finally, ursodeoxycholic acid can be prepared according to the manner set forth in U.S. Pat. No. 5,843,929.

Still more preferred antineoplastic agents include: anastrozole, calcium carbonate, capecitabine, carboplatin, cisplatin, Cell Pathways CP-461, cyclophosphamide, docetaxel, doxorubicin, etoposide, Exisulind®, fluorouracil (5-FU), fluoxymestrine, gemcitabine, goserelin, irinotecan, ketoconazole, letrozol, leucovorin, levamisole, megestrol, mitoxantrone, paclitaxel, raloxifene, retinoic acid, tamoxifen, thiotepa, topotecan, toremifene, vinorelbine, vinblastine, vincristine, selenium (selenomethionine), ursodeoxycholic acid, sulindac sulfone and eflornithine (DFMO).

The phrase "taxane" includes a family of diterpene alkaloids all of which contain a particular eight (8) member "taxane" ring structure. Taxanes such as paclitaxel prevent the normal post division breakdown of microtubules which form to pull and separate the newly duplicated chromosome pairs to opposite poles of the cell prior to cell division. In cancer cells which are rapidly dividing, taxane therapy causes the microtubules to accumulate which ultimately prevents further division of the cancer cell. Taxane therapy also affects other cell processes dependant on microtubules such as cell motility, cell shape and intracellular transport. The major adverse side-effects associated with taxane therapy can be classified into cardiac effects, neurotoxicity, haematological toxicity, and hypersensitivity reactions. (See Exp. Opin. Thera. Patents (1998) 8(5), hereby incorporated by reference). Specific adverse side-effects include neutropenia, alopecia, bradycardia, cardiac conduction defects, acute hypersensitivity reactions, neuropathy, mucositis, dermatitis, extravascular fluid accumulation, arthralgias, and myalgias. Various treatment regimens have been developed in an effort to minimize the side effects of taxane therapy, but adverse side-effects remain the limiting factor in taxane therapy.

Taxane derivatives have been found to be useful in treating refractory ovarian carcinoma, urothelial cancer, breast carcinoma, melanoma, non-small-cell lung carcinoma, gastric, and colon carcinomas, squamous carcinoma of the head and neck, lymphoblastic, myeloblastic leukemia, and carcinoma of the esophagus.

Paclitaxel is typically administered in a 15–420 mg/m$^2$ dose over a 6 to 24 hour infusion. For renal cell carcinoma, squamous carcinoma of head and neck, carcinoma of esophagus, small and non-small cell lung cancer, and breast cancer, paclitaxel is typically administered as a 250 mg/m$^2$ 24 hour infusion every 3 weeks. For refractory ovarian cancer paclitaxel is typically dose escalated starting at 110 mg/m$^2$. Docetaxel is typically administered in a 60–100 mg/M$^2$ i.v. over 1 hour, every three weeks. It should be noted, however, that specific dose regimen depends upon dosing considerations based upon a variety of factors including the type of neoplasia; the stage of the neoplasm; the age, weight, sex, and medical condition of the patient; the route of administration; the renal and hepatic function of the patient; and the particular agents and combination employed.

In one embodiment, paclitaxel is used in the present invention in combination with a matrix metalloproteinase inhibitor and with cisplatin, cyclophosphamide, or doxorubicin for the treatment of breast cancer. In another embodiment paciltaxel is used in combination with a matrix metalloproteinase inhibitor, cisplatin or carboplatin, and ifosfamide for the treatment of ovarian cancer.

In another embodiment docetaxal is used in the present invention in combination with a matrix metalloproteinase inhibitor and in combination with cisplatin, cyclophosphamide, or doxorubicin for the treatment of ovary and breast cancer and for patients with locally advanced or metastatic breast cancer who have progressed during anthracycline based therapy.

The following references listed in Table No. 9 below, hereby individually incorporated by reference herein, describe various taxanes and taxane derivatives suitable for use in the present invention, and processes for their manufacture.

TABLE No. 9

Taxanes and taxane derivatives

| | | | |
|---|---|---|---|
| EP 694539 | EP 683232 | EP 639577 | EP 627418 |
| EP 604910 | EP 797988 | EP 727492 | EP 767786 |
| EP 767376 | U.S. Pat. No. 5886026 | U.S. Pat. No. 5880131 | U.S. Pat. No. 5879929 |
| U.S. Pat. No. 5871979 | U.S. Pat. No. 5869680 | U.S. Pat. No. 5871979 | U.S. Pat. No. 5854278 |
| U.S. Pat. No. 5840930 | U.S. Pat. No. 5840748 | U.S. Pat. No. 5827831 | U.S. Pat. No. 5824701 |
| U.S. Pat. No. 5821363 | U.S. Pat. No. 5821263 | U.S. Pat. No. 5811292 | U.S. Pat. No. 5808113 |
| U.S. Pat. No. 5808102 | U.S. Pat. No. 5807888 | U.S. Pat. No. 5780653 | U.S. Pat. No. 5773461 |
| U.S. Pat. No. 5770745 | U.S. Pat. No. 5767282 | U.S. Pat. No. 5763628 | U.S. Pat. No. 5760252 |
| U.S. Pat. No. 5760251 | U.S. Pat. No. 5756776 | U.S. Pat. No. 5750737 | U.S. Pat. No. 5744592 |
| U.S. Pat. No. 5739362 | U.S. Pat. No. 5728850 | U.S. Pat. No. 5728725 | U.S. Pat. No. 5723634 |
| U.S. Pat. No. 5721268 | U.S. Pat. No. 5717115 | U.S. Pat. No. 5716981 | U.S. Pat. No. 5714513 |
| U.S. Pat. No. 5710287 | U.S. Pat. No. 5705508 | U.S. Pat. No. 5703247 | U.S. Pat. No. 5703117 |
| U.S. Pat. No. 5700669 | U.S. Pat. No. 5693666 | U.S. Pat. No. 5688977 | U.S. Pat. No. 5684175 |
| U.S. Pat. No. 5683715 | U.S. Pat. No. 5679807 | U.S. Pat. No. 5677462 | U.S. Pat. No. 5675025 |
| U.S. Pat. No. 5670673 | U.S. Pat. No. 5654448 | U.S. Pat. No. 5654447 | U.S. Pat. No. 5646176 |
| U.S. Pat. No. 5637732 | U.S. Pat. No. 5637484 | U.S. Pat. No. 5635531 | U.S. Pat. No. 5631278 |
| U.S. Pat. No. 5629433 | U.S. Pat. No. 5622986 | U.S. Pat. No. 5618952 | U.S. Pat. No. 5616740 |
| U.S. Pat. No. 5616739 | U.S. Pat. No. 5614645 | U.S. Pat. No. 5614549 | U.S. Pat. No. 5608102 |
| U.S. Pat. No. 5599820 | U.S. Pat. No. 5594157 | U.S. Pat. No. 5587489 | U.S. Pat. No. 5580899 |
| U.S. Pat. No. 5574156 | U.S. Pat. No. 5567614 | U.S. Pat. No. 5565478 | U.S. Pat. No. 5560872 |
| U.S. Pat. No. 5556878 | U.S. Pat. No. 5547981 | U.S. Pat. No. 5539103 | U.S. Pat. No. 5532363 |
| U.S. Pat. No. 5530020 | U.S. Pat. No. 5508447 | U.S. Pat. No. 5489601 | U.S. Pat. No. 5484809 |
| U.S. Pat. No. 5475011 | U.S. Pat. No. 5473055 | U.S. Pat. No. 5470866 | U.S. Pat. No. 5466834 |
| U.S. Pat. No. 5449790 | U.S. Pat. No. 5442065 | U.S. Pat. No. 5440056 | U.S. Pat. No. 5430160 |
| U.S. Pat. No. 5412116 | U.S. Pat. No. 5412092 | U.S. Pat. No. 5411984 | U.S. Pat. No. 5407816 |
| U.S. Pat. No. 5407674 | U.S. Pat. No. 5405972 | U.S. Pat. No. 5399726 | U.S. Pat. No. 5395850 |
| U.S. Pat. No. 5384399 | U.S. Pat. No. 5380916 | U.S. Pat. No. 5380751 | U.S. Pat. No. 5367086 |
| U.S. Pat. No. 5356928 | U.S. Pat. No. 5356927 | U.S. Pat. No. 5352806 | U.S. Pat. No. 5350866 |
| U.S. Pat. No. 5344775 | U.S. Pat. No. 5338872 | U.S. Pat. No. 5336785 | U.S. Pat. No. 5319112 |
| U.S. Pat. No. 5296506 | U.S. Pat. No. 5294737 | U.S. Pat. No. 5294637 | U.S. Pat. No. 5284865 |
| U.S. Pat. No. 5284864 | U.S. Pat. No. 5283253 | U.S. Pat. No. 5279949 | U.S. Pat. No. 5274137 |
| U.S. Pat. No. 5274124 | U.S. Pat. No. 5272171 | U.S. Pat. No. 5254703 | U.S. Pat. No. 5254580 |
| U.S. Pat. No. 5250683 | U.S. Pat. No. 5243045 | U.S. Pat. No. 5229526 | U.S. Pat. No. 5227400 |
| U.S. Pat. No. 5200534 | U.S. Pat. No. 5194635 | U.S. Pat. No. 5175,315 | U.S. Pat. No. 5136060 |
| U.S. Pat. No. 5015744 | WO 98/38862 | WO 95/24402 | WO 93/21173 |
| EP 681574 | EP 681575 | EP 568203 | EP 642503 |
| EP 667772 | EP 668762 | EP 679082 | EP 681573 |
| EP 688212 | EP 690712 | EP 690853 | EP 710223 |
| EP 534708 | EP 534709 | EP 605638 | EP 669918 |
| EP 855909 | EP 605638 | EP 428376 | EP 428376 |
| EP 534707 | EP 605637 | EP 679156 | EP 689436 |
| EP 690867 | EP 605637 | EP 690867 | EP 687260 |
| EP 690711 | EP 400971 | EP 690711 | EP 400971 |
| EP 690711 | EP 884314 | EP 568203 | EP 534706 |
| EP 428376 | EP 534707 | EP 400971 | EP 669918 |
| EP 605637 | U.S. Pat. No. 5015744 | U.S. Pat. No. 5175315 | U.S. Pat. No. 5243045 |
| U.S. Pat. No. 5283253 | U.S. Pat. No. 5250683 | U.S. Pat. No. 5254703 | U.S. Pat. No. 5274124 |
| U.S. Pat. No. 5284864 | U.S. Pat. No. 5284865 | U.S. Pat. No. 5350866 | U.S. Pat. No. 5227400 |
| U.S. Pat. No. 5229526 | U.S. Pat. No. 4876399 | U.S. Pat. No. 5136060 | U.S. Pat. No. 5336785 |
| U.S. Pat. No. 5710287 | U.S. Pat. No. 5714513 | U.S. Pat. No. 5717115 | U.S. Pat. No. 5721268 |
| U.S. Pat. No. 5723634 | U.S. Pat. No. 5728725 | U.S. Pat. No. 5728850 | U.S. Pat. No. 5739362 |
| U.S. Pat. No. 5760219 | U.S. Pat. No. 5760252 | U.S. Pat. No. 5384399 | U.S. Pat. No. 5399726 |
| U.S. Pat. No. 5405972 | U.S. Pat. No. 5430160 | U.S. Pat. No. 5466834 | U.S. Pat. No. 5489601 |
| U.S. Pat. No. 5532363 | U.S. Pat. No. 5539103 | U.S. Pat. No. 5574156 | U.S. Pat. No. 5587489 |
| U.S. Pat. No. 5618952 | U.S. Pat. No. 5637732 | U.S. Pat. No. 5654447 | U.S. Pat. No. 4942184 |
| U.S. Pat. No. 5059699 | U.S. Pat. No. 5157149 | U.S. Pat. No. 5202488 | U.S. Pat. No. 5750736 |
| U.S. Pat. No. 5202488 | U.S. Pat. No. 5549830 | U.S. Pat. No. 5281727 | U.S. Pat. No. 5019504 |
| U.S. Pat. No. 4857653 | U.S. Pat. No. 4924011 | U.S. Pat. No. 5733388 | U.S. Pat. No. 5696153 |
| WO 93/06093 | WO 93/06094 | WO 94/10996 | WO 9/10997 |
| WO 94/11362 | WO 94/15599 | WO 94/15929 | WO 94/17050 |
| WO 94/17051 | WO 94/17052 | WO 94/20088 | WO 94/20485 |
| WO 94/21250 | WO 94/21251 | WO 94/21252 | WO 94/21623 |
| WO 94/21651 | WO 95/03265 | WO 97/09979 | WO 97/42181 |
| WO 99/08986 | WO 99/09021 | WO 93/06079 | U.S. Pat. No. 5202448 |
| U.S. Pat. No. 5019504 | U.S. Pat. No. 4657653 | U.S. Pat. No. 4924011 | WO 97/15571 |
| WO 96/38138 | U.S. Pat. No. 5489589 | EP 781778 | WO 96/11683 |
| EP 639577 | EP 747385 | U.S. Pat. No. 5422364 | WO 95/11020 |
| EP 747372 | WO 96/36622 | U.S. Pat. No. 5599820 | WO 97/10234 |
| WO 96/21658 | WO 97/23472 | U.S. Pat. No. 5550261 | WO 95/20582 |
| WO 97/28156 | WO 96/14309 | WO 97/32587 | WO 96/28435 |
| WO 96/03394 | WO 95/25728 | WO 94/29288 | WO 96/00724 |
| WO 95/02400 | EP 694539 | WO 95/24402 | WO 93/10121 |
| WO 97/19086 | WO 97/20835 | WO 96/14745 | WO 96/36335 |

U.S. Pat. No. 5,019,504 describes the isolation of paclitaxel and related alkaloids from culture grown *Taxus brevifolia* cells.

U.S. Pat. No. 5,675,025 describes methods for synthesis of Taxol®, Taxol® analogues and intermediates from baccatin III.

U.S. Pat. No. 5,688,977 describes the synthesis of Docetaxel from 10-deacetyl baccatin III.

U.S. Pat. No. 5,202,488 describes the conversion of partially purified taxane mixture to baccatin III.

U.S. Pat. No. 5,869,680 describes the process of preparing taxane derivatives.

U.S. Pat. No. 5,856,532 describes the process of the production of Taxol®.

U.S. Pat. No. 5,750,737 describes the method for paclitaxel synthesis.

U.S. Pat. No. 6,688,977 describes methods for docetaxel synthesis.

U.S. Pat. No. 5,677,462 describes the process of preparing taxane derivatives.

U.S. Pat. No. 5,594,157 describes the process of making Taxol® derivatives.

Some preferred taxanes and taxane derivatives are described in the patents listed in Table No. 10 below, and are hereby individually incorporated by reference herein.

TABLE No. 10

Some preferred taxanes and taxane derivatives

| | | | |
|---|---|---|---|
| U.S. Pat. No. 5015744 | U.S. Pat. No. 5136060 | U.S. Pat. No. 5175315 | U.S. Pat. No. 5200534 |
| U.S. Pat. No. 5194635 | U.S. Pat. No. 5227400 | U.S. Pat. No. 4924012 | U.S. Pat. No. 5641803 |
| U.S. Pat. No. 5059699 | U.S. Pat. No. 5157049 | U.S. Pat. No. 4942184 | U.S. Pat. No. 4960790 |
| U.S. Pat. No. 5202488 | U.S. Pat. No. 5675025 | U.S. Pat. No. 5688977 | U.S. Pat. No. 5750736 |
| U.S. Pat. No. 5684175 | U.S. Pat. No. 5019504 | U.S. Pat. No. 4814470 | WO 95/01969 |

The phrase "retinoid" includes compounds which are natural and synthetic analogues of retinol (Vitamin A). The retinoids bind to one or more retinoic acid receptors to initiate diverse processes such as reproduction, development, bone formation, cellular proliferation and differentiation, apoptosis, hematopoiesis, immune function and vision. Retinoids are required to maintain normal differentiation and proliferation of almost all cells and have been shown to reverse/suppress carcinogenesis in a variety of in vitro and in vivo experimental models of cancer, see (Moon et al., Ch. 14 Retinoids and cancer. In The Retinoids, Vol. 2. Academic Press, Inc. 1984). Also see Roberts et al. Cellular biology and biochemistry of the retinoids. In The Retinoids, Vol. 2. Academic Press, Inc. 1984, hereby incorporated by reference), which also shows that vesanoid (tretinoin trans retinoic acid) is indicated for induction of remission in patients with acute promyelocytic leukemia (APL).

A synthetic description of retinoid compounds, hereby incorporated by reference, is described in: Dawson M I and Hobbs P D. The synthetic chemistry of retinoids: in The retinoids, $2^{nd}$ edition. M B Sporn, A B Roberts, and D S Goodman (eds). New York: Raven Press, 1994, pp 5–178.

Lingen et al. describe the use of retinoic acid and interferon alpha against head and neck squamous cell carcinoma (Lingen, M W et al., Retinoic acid and interferon alpha act synergistically as antiangiogenic and antitumor agents against human head and neck squamous cell carcinoma. Cancer Research 58 (23) 5551–5558 (1998), hereby incorporated by reference).

Iurlaro et al. describe the use of beta interferon and 13-cis retinoic acid to inhibit angiogenesis. (Iurlaro, M et al., Beta interferon inhibits HIV-1 Tat-induced angiogenesis: synergism with 13-cis retinoic acid. European Journal of Cancer 34 (4) 570–576 (1998), hereby incorporated by reference).

Majewski et al. describe Vitamin D3 and retinoids in the inhibition of tumor cell-induced angiogenesis. (Majewski, S et al., Vitamin D3 is a potent inhibitor of tumor cell-induced angiogenesis. J. Invest. Dermatology. Symposium Proceedings, 1 (1), 97–101 (1996), hereby incorporated by reference.

Majewski et al. describe the role of retinoids and other factors in tumor angiogenesis. Majewski, S et al., Role of cytokines, retinoids and other factors in tumor angiogenesis. Central-European journal of Immunology 21 (4) 281–289 (1996), hereby incorporated by reference).

Bollag describes retinoids and alpha-interferon in the prevention and treatment of neoplastic disease. (Bollag W. Retinoids and alpha-interferon in the prevention and treatment of preneoplastic and neoplastic diseases. Chemotherapie Journal, (Suppl) 5 (10) 55–64 (1996), hereby incorporated by reference.

Bigg, H F et al. describe all-trans retinoic acid with basic fibroblast growth factor and epidermal growth factor to stimulate tissue inhibitor of metalloproteinases from fibroblasts. (Bigg, H F et al., All-trans-retoic acid interacts synergystically with basic fibroblast growth factor and epidermal growth factor to stimulate the production of tissue inhibitor of metalloproteinases from fibroblasts. Arch. Biochem. Biophys. 319 (1) 74–83 (1995), hereby incorporated by reference).

Nonlimiting examples of retinoids that may be used in the present invention are identified in Table No. 11 below.

TABLE No. 11

Retinoids

| Compound | Common Name/ Trade Name | Company | Reference | Dosage |
|---|---|---|---|---|
| CD-271 | Adapaline | | EP 199636 | |
| Tretinoin trans retinoic acid | Vesanoid | Roche Holdings | | 45 mg/M²/day as two evenly divided doses until complete remission |
| 2,4,6,8-Nonatetraenoic acid, 9-(4-methoxy-2,3,6-trimethyl-phenyl)-3,7-dimethyl-ethyl | etretinate isoetretin; Ro-10-9359; Ro-13-7652; Tegison; Tigason | Roche Holdings | US 4215215 | .25–1.5 mg/kg/day |

TABLE No. 11-continued

Retinoids

| Compound | Common Name/ Trade Name | Company | Reference | Dosage |
|---|---|---|---|---|
| ester, (all-E)- | | | | |
| Retinoic acid, 13-cis- | isotretinoin Accutane; Isotrex; Ro-4-3780; Roaccutan; Roaccutane | Roche Holdings | US 4843096 | .5 to 2 mg/kg/day |
| | Roche Ro-40-0655 | Roche Holdings | | |
| | Roche Ro-25-6760 | Roche Holdings | | |
| | Roche Ro-25-9022 | Roche Holdings | | |
| | Roche Ro-25-9716 | Roche Holdings | | |
| Benzoic acid, 4-[[3,5-bis(tri-methyl-silyl)-benzoyl]amino]- | TAC-101 | Taiho Pharmaceutical | | |
| Retinamide, N-(4-hydroxy-phenyl)- | fenretinide 4-HPR; HPR; McN-R-1967 | | | 50–400 mg/kg/day |
| (2E,4E,6E)-7-(3,5-Di-tert-butylphenyl)-3-methylocta-2,4,6-trienoic acid | LGD-1550 ALRT-1550; ALRT-550; LG-1550 | Ligand Pharmaceuticas; Allergan USA | | 20 microg/m2/day to 400 microg/m2/day administered as a single daily oral dose |
| | Molecular Design MDI-101 | | US 4885311 | |
| | Molecular Design MDI-403 | | US 4677120 | |
| Benzoic acid, 4-(1-(5,6,7,8-tetrahydro-3,5,5,8,8- | bexarotene LG-1064; LG-1069; LGD-1069; Targretin; | | WO 94/15901 | |
| pentamethyl-2-naphtha-lenyl)ethenyl)-Benzoic acid, 4-(1-(5,6,7,8-tetrahydro-3,5,8,8-pentamethyl-2-naphthalenyl)ethenyl)-(2E,4E)-3-methyl-5-[3-(5,5,8,8 tetramethyl-5,6,7,8-tetrahydro-naphthalen-2-yl)-thiopen-2-yl]-penta-2,4-dienoic acid | Targretin Oral; Targretin Topical Gel bexarotene, soft gel, bexarotene, Ligand; bexaroten | R P Scherer | WO 96/05165 | |
| | SR-11262 F | Hoffmann-La Roche Ltd | | |
| | BMS-181162 | Bristol Myers Squibb | EP 476682 | |
| N-(4-hydroxy-phenyl) retinamide | IIT Research Institute | | Cancer Research 39, 1339–1346 (1979) | |
| | AGN-193174 | Allergan USA | WO 96/33716 | |

The following individual patent references listed in Table No. 12 below, hereby individually incorporated by reference, describe various retinoid and retinoid derivatives suitable for use in the present invention described herein, and processes for their manufacture.

TABLE No. 12

Retinoids

| | | | |
|---|---|---|---|
| U.S. Pat. No. 4215215 | U.S. Pat. No. 4885311 | U.S. Pat. No. 4677120 | U.S. Pat. No. 4105681 |
| U.S. Pat. No. 5260059 | U.S. Pat. No. 4503035 | U.S. Pat. No. 5827836 | U.S. Pat. No. 3878202 |
| U.S. Pat. No. 4843096 | WO 96/05165 | WO 97/34869 | WO 97/49704 |
| U.S. Pat. No. 5547947 | EP 552624 | EP 728742 | EP 331983 |
| EP 19/9636 | WO 96/33716 | WO 97/24116 | WO 97/09297 |
| WO 98/36742 | WO 97/25969 | WO 96/11686 | WO 94/15901 |
| WO 97/24116 | CH 61/6134 | DE 2854354 | EP 579915 |
| EP 476682 | | | |

Some preferred retinoids include Accutane; Adapalene; Allergan AGN-193174; Allergan AGN-193676; Allergan AGN-193836; Allergan AGN-193109; Aronex AR-623; BMS-181162; Galderma CD-437; Eisai ER-34617; Etrinate; Fenretinide; Ligand LGD-1550; lexacalcitol; Maxia Pharmaceuticals MX-781; mofarotene; Molecular Design MDI-101; Molecular Design MDI-301; Molecular Design MDI-403; Motretinide; Eisai 4-(2-[5-(4-methyl-7-ethylbenzofuran-2-yl)pyrrolyl])benzoic acid; Johnson & Johnson N-[4-[2-thyl-1-(1H-imidazol-1-yl)butyl]phenyl]-2-benzothiazolamine; Soriatane; Roche SR-11262; Tocoretinate; Advanced Polymer Systems trans-retinoic acid; UAB Research Foundation UAB-8; Tazorac; TopiCare; Taiho TAC-101; and Vesanoid.

cGMP phosphodiesterase inhibitors, including Sulindac sulfone (Exisuland®) and CP-461 for example, are apoptosis inducers and do not inhibit the cyclooxygenase pathways. cGMP phosphodiesterase inhibitors increase apoptosis in tumor cells without arresting the normal cycle of cell division or altering the cell's expression of the p53 gene.

Ornithine decarboxylase is a key enzyme in the polyamine synthesis pathway that is elevated in most tumors and premalignant lesions. Induction of cell growth and proliferation is associated with dramatic increases in ornithine decarboxylase activity and subsequent polyamine synthesis. Further, blocking the formation of polyamines slows or arrests growth in transformed cells. Consequently, polyamines are thought to play a role in tumor growth. Difluoromethylornithine (DFMO) is a potent inhibitor of ornithine decarboxylase that has been shown to inhibit carcinogen-induced cancer development in a variety of rodent models (Meyskens et al. Development of Difluoromethylornithine (DFMO) as a chemoprevention agent. Clin. Cancer Res. 1999 May, 5(%):945–951, hereby incorporated by reference, herein). DFMO is also known as 2-difluoromethyl-2,5-diaminopentanoic acid, or 2-difluoromethyl-2,5-diaminovaleric acid, or a-(difluoromethyl) ornithine; DFMO is marketed under the tradename Elfornithine®. Therefore, the use of DFMO in combination with COX-2 inhibitors is contemplated to treat or prevent cancer, including but not limited to colon cancer or colonic polyps.

Populations with high levels of dietary calcium have been reported to be protected from colon cancer. In vivo, calcium carbonate has been shown to inhibit colon cancer via a mechanism of action independent from COX-2 inhibition. Further, calcium carbonate is well tolerated. A combination therapy consisting of calcium carbonate and a selective COX-2 inhibitor is contemplated to treat or prevent cancer, including but not limited to colon cancer or colonic polyps.

Several studies have focused attention on bile acids as a potential mediator of the dietary influence on colorectal cancer risk. Bile acids are important detergents for fat solubilization and digestion in the proximal intestine. Specific transprot processes in the apical domain of the terminal ileal enterocyte and basolateral domain of the hepatocyte account for the efficient conservation in the enterohepatic circulation. Only a small fraction of bile acids enter the colon; however, perturbations of the cycling rate of bile acids by diet (e.g. fat) or surgery may increase the fecal bile load and perhaps account for the associated increased risk of colon cancer. (Hill M J, Bile flow and colon cancer. 238 Mutation Review, 313 (1990). Ursodeoxycholate (URSO), the hydrophilic 7-beta epimer of chenodeoxycholate, is non cytotoxic in a variety of cell model systems including colonic epithelia. URSO is also virtually free of side effects. URSO, at doses of 15 mg/kg/day used primarily in biliary cirrhosis trials were extremely well tolerated and without toxicity. (Pourpon et al., A multicenter, controlled trial of ursodiol for the treatment of primary biliary cirrhosis. 324 New Engl. J. Med. 1548 (1991)). While the precise mechanism of URSO action is unknown, beneficial effects of URSO therapy are related to the enrichment of the hepatic bile acid pool with this hydrophilic bile acid. It has thus been hypothesized that bile acids more hydrophilic than URSO will have even greater beneficial effects than URSO. For example, tauroursodeoxycholate (TURSO) the taurine conjugate of URSO. Non-steroidal anti-inflammatory drugs (NSAIDs) can inhibit the neoplastic transformation of colorectal epithelium. The likely mechanism to explain this chemopreventive effect is inhibition of prostaglandin synthesis. NSAIDs inhibit cyclooxygenase, the enzyme that converts arachidonic acid to prostaglandins and thromboxanes. However, the potential chemopreventive benefits of NSAIDs such as sulindac or mesalamine are tempered by their well known toxicities and moderately high risk of intolerance. Abdominal pain, dispepsia, nausea, diarrhea, constipation, rash, dizziness, or headaches have been reported in up to 9% of patients. The elderly appear to be particularly vulnerable as the incidence of NSAID-induced gastroduodenal ulcer disease, including gastrointestinal bleeding, is higher in those over the age of 60; this is also the age group most likely to develop colon cancer, and therefore most likely to benefit from chemoprevention. The gastrointestinal side effects associated with NSAID use result from the inhibition of cyclooxygenase-1, an enzyme responsible for maintenance of the gastric mucosa. Therefore, the use of COX-2 inhibitors in combination with URSO is contemplated to treat or prevent cancer, including but not limited to colon cancer or colonic polyps; it is contemplated that this treatment will result in lower gastrointestinal side effects than the combination of standard NSAIDs and URSO.

An additional class of antineoplastic agents that may be used in the present invention include nonsteroidal antiinflammatory drugs (NSAIDs). NSAIDs have been found to prevent the production of prostaglandins by inhibiting enzymes in the human arachidonic acid/prostaglandin pathway, including the enzyme cyclooxygenase (COX). However, for the purposes of the present invention the definition of an NSAID does not include the "cyclooxygenase-2 inhibitors" described herein. Thus the phrase "nonsteroidal antiinflammatory drug" or "NSAID" includes agents that specifically inhibit cyclooxygenase-1, without significant inhibition of cyclooxygenase-2; or inhibit cyclooxygenase-1 and cyclooxygenase-2 at substantially the same potency; or inhibit neither cyclooxygenase-1 or cyclooxygenase-2. The potency and selectivity for the enzyme cyclooxygenase-1 and cyclooxygenase-2 can be determined by assays well known in the art, see for example, Cromlish and Kennedy, Biochemical Pharmacology, Vol. 52, pp 1777–1785, 1996.

Examples of NSAIDs that can be used in the combinations of the present invention include sulindac, indomethacin, naproxen, diclofenac, tolectin, fenoprofen, phenylbutazone, piroxicam, ibuprofen, ketophen, mefenamic acid, tolmetin, flufenamic acid, nimesulide, niflumic acid, piroxicam, tenoxicam, phenylbutazone, fenclofenac, flurbiprofen, ketoprofen, fenoprofen, acetaminophen, salicylate and aspirin.

The term "clinical tumor" includes neoplasms that are identifiable through clinical screening or diagnostic procedures including, but not limited to, palpation, biopsy, cell proliferation index, endoscopy, mammography, digital mammography, ultrasonography, computed tomagraphy (CT), magnetic resonance imaging (MRI), positron emmission tomaagraphy (PET), radiography, radionuclide evaluation, CT- or MRI-guided aspiration cytology, and imaging-guided needle biopsy, among others. Such diagnostic techniques are well known to those skilled in the art and are described in Cancer Medicine 4$^{th}$ Edition, Volume One. J. F. Holland, R. C. Bast, D. L. Morton, E. Frei III, D. W. Kufe, and R. R. Weichselbaum (Editors). Williams & Wilkins, Baltimore (1997).

The term "tumor marker" or "tumor biomarker" encompasses a wide variety of molecules with divergent characteristics that appear in body fluids or tissue in association with a clinical tumor and also includes tumor-associated chromosomal changes. Tumor markers fall primarily into three categories: molecular or cellular markers, chromosomal markers, and serological or serum markers. Molecular and chromosomal markers complement standard parameters used to describe a tumor (i.e. histopathology, grade, tumor size) and are used primarily in refining disease diagnosis and prognosis after clinical manifestation. Serum markers can often be measured many months before clinical tumor detection and are thus useful as an early diagnostic test, in patient monitoring, and in therapy evaluation.

Molecular Tumor Markers

Molecular markers of cancer are products of cancer cells or molecular changes that take place in cells because of activation of cell division or inhibition of apoptosis. Expression of these markers can predict a cell's malignant potential. Because cellular markers are not secreted, tumor tissue samples are generally required for their detection. Non-limiting examples of molecular tumor markers that can be used in the present invention are listed in Table No. 1, below.

TABLE 1

Non-limiting Examples of Molecular Tumor Markers

| Tumor | Marker |
| --- | --- |
| Breast | p53 |
| Breast, Ovarian | ErbB-2/Her-2 |
| Breast | S phase and ploidy |
| Breast | pS2 |
| Breast | MDR2 |
| Breast | urokinase plasminogen activator |
| Breast, Colon, Lung | myc family |

Chromosomal Tumor Markers

Somatic mutations and chromosomal aberrations have been associated with a variety of tumors. Since the identification of the Philadelphia Chromosome by Nowel and Hungerford, a wide effort to identify tumor-specific chromosomal alterations has ensued. Chromosomal cancer markers, like cellular markers, are can be used in the diagnosis and prognosis of cancer. In addition to the diagnostic and prognostic implications of chromosomal alterations, it is hypothesized that germ-line mutations can be used to predict the likelihood that a particular person will develop a given type of tumor. Non-limiting examples of chromosomal tumor markers that can be used in the present invention are listed in Table No. 2, below.

TABLE 2

Non-limiting Examples of Chromosomal Tumor Markers

| Tumor | Marker |
| --- | --- |
| Breast | 1p36 loss |
| Breast | 6q24-27 loss |
| Breast | 11q22-23 loss |
| Breast | 11q13 amplification |
| Breast | TP53 mutation |
| Colon | Gain of chromosome 13 |
| Colon | Deletion of short arm of chromosome 1 |
| Lung | Loss of 3p |
| Lung | Loss of 13q |
| Lung | Loss of 17p |
| Lung | Loss of 9p |

Serological Tumor Markers

Serum markers including soluble antigens, enzymes and hormones comprise a third category of tumor markers. Monitoring serum tumor marker concentrations during therapy provides an early indication of tumor recurrence and of therapy efficacy. Serum markers are advantageous for patient surveillance compared to chromosomal and cellular markers because serum samples are more easily obtainable than tissue samples, and because serum assays can be performed serially and more rapidly. Serum tumor markers can be used to determine appropriate therapeutic doses within individual patients. For example, the efficacy of a combination regimen consisting of chemotherapeutic and antiangiogenic agents can be measured by monitoring the relevant serum cancer marker levels. Moreover, an efficacious therapy dose can be achieved by modulating the therapeutic dose so as to keep the particular serum tumor marker concentration stable or within the reference range, which may vary depending upon the indication. The amount of therapy can then be modulated specifically for each patient so as to minimize side effects while still maintaining stable, reference range tumor marker levels. Table No. 3 provides non-limiting examples of serological tumor markers that can be used in the present invention.

TABLE 3

Non-limiting Examples of Serum Tumor Markers

| Cancer Type | Marker |
| --- | --- |
| Germ Cell Tumors | a-fetoprotein (AFP) |
| Germ Cell Tumors | human chorionic gonadotrophin (hCG) |
| Germ Cell Tumors | placental alkaline phosphatase (PLAP) |
| Germ Cell Tumors | lactate dehydrogenase (LDH) |
| Prostate | prostate specific antigen (PSA) |
| Breast | carcinoembryonic antigen (CEA) |
| Breast | MUC-1 antigen (CA15-3) |
| Breast | tissue polypeptide antigen (TPA) |
| Breast | tissue polypeptide specific antigen (TPS) |
| Breast | CYFRA 21.1 |
| Breast | soluble erb-B-2 |
| Ovarian | CA125 |
| Ovarian | OVX1 |
| Ovarian | cancer antigen CA72-4 |
| Ovarian | TPA |
| Ovarian | TPS |

TABLE 3-continued

Non-limiting Examples of Serum Tumor Markers

| Cancer Type | Marker |
|---|---|
| Gastrointestinal | CD44v6 |
| Gastrointestinal | CEA |
| Gastrointestinal | cancer antigen CA19-9 |
| Gastrointestinal | NCC-ST-439 antigen (Dukes C) |
| Gastrointestinal | cancer antigen CA242 |
| Gastrointestinal | soluble erb-B-2 |
| Gastrointestinal | cancer antigen CA195 |
| Gastrointestinal | TPA |
| Gastrointestinal | YKL-40 |
| Gastrointestinal | TPS |
| Esophageal | CYFRA 21-1 |
| Esophageal | TPA |
| Esophageal | TPS |
| Esophageal | cancer antigen CA19-9 |
| Gastric Cancer | CEA |
| Gastric Cancer | cancer antigen CA19-9 |
| Gastric Cancer | cancer antigen CA72-4 |
| Lung | neruon specific enolase (NSE) |
| Lung | CEA |
| \Lung | CYFRA 21-1 |
| Lung | cancer antigen CA 125 |
| Lung | TPA |
| Lung | squamous cell carcinoma antigen (SCC) |
| Pancreatic cancer | ca19-9 |
| Pancreatic cancer | ca50 |
| Pancreatic cancer | ca119 |
| Pancreatic cancer | ca125 |
| Pancreatic cancer | CEA |
| Pancreatic cancer | |
| Renal Cancer | CD44v6 |
| Renal Cancer | E-cadherin |
| Renal Cancer | PCNA (proliferating cell nuclear antigen) |

EXAMPLES

Germ Cell Cancers

Non-limiting examples of tumor markers useful in the present invention for the detection of germ cell cancers include, but are not limited to, a-fetoprotein (AFP), human chorionic gonadotrophin (hCG) and its beta subunit (hCGb), lactate dehydrogenase (LDH), and placental alkaline phosphatase (PLAP).

AFP has an upper reference limit of approximately –10 kU/L after the first year of life and may be elevated in germ cell tumors, hepatocellular carcinoma and also in gastric, colon, biliary, pancreatic and lung cancers. AFP serum half life is approximately five days after orchidectomy. According to EGTM recommendations, AFP serum levels less than 1,000 kU/L correlate with a good prognosis, AFP levels between 1,000 and 10,000 kU/L, inclusive, correlate with intermediate prognosis, and AFP levels greater than 10,000 U/L correlate with a poor prognosis.

HCG is synthesized in the placenta and is also produced by malignant cells. Serum hCG concentrations may be increased in pancreatic adenocarcinomas, islet cell tumors, tumors of the small and large bowel, hepatoma, stomach, lung, ovaries, breast and kidney. Because some tumors only hCGb, measurement of both hCG and hCGb is recommended. Normally, serum hCG in men and pre-menopausal women is as high as –5 U/L while post-menopausal women have levels up to –10 U/L. Serum half life of hCG ranges from 16–24 hours. According to the EGTM, hCG serum levels under 5000 U/L correlate with a good prognosis, levels between 5000 and 50000 U/L, inclusively correlate with an intermediate prognosis, and hCG serum levels greater than 50000 U/L correlate with a poor prognosis. Further, normal hCG half lives correlate with good prognosis while prolonged half lives correlate with poor prognosis.

LDH is an enzyme expressed in cardiac and skeletal muscle as well as in other organs. The LDH-1 isoenzyme is most commonly found in testicular germ cell tumors but can also occur in a variety of benign conditions such as skeletal muscle disease and myocardial infarction. Total LDH is used to measure independent prognostic value in patients with advanced germ cell tumors. LDH levels less than 1.5× the reference range are associated with a good prognosis, levels between 1.5 and 10× the reference range, inclusive, are associated with an intermediate prognosis, and levels more than 10× the reference range are associated with a poor prognosis.

PLAP is a enzyme of alkaline phosphatase normally expressed by placental syncytiotrophoblasts. Elevated serum concentrations of PLAP are found in seminomas, non-seminomatous tumors, and ovarian tumors, and may also provide a marker for testicular tumors. PLAP has a normal half life after surgical resection of between 0.6 and 2.8 days.

Prostate Cancer

A nonlimiting example of a tumor marker useful in the present invention for the detection of prostate cancer is prostate specific antigen (PSA). PSA is a glycoprotein that is almost exclusively produced in the prostate. In human serum, uncomplexed f-PSA and a complex of f-PSA with a1-anthichymotrypsin make up total PSA (t-PSA). T-PSA is useful in determining prognosis in patients that are not currently undergoing anti-androgen treatment. Rising t-PSA levels via serial measurement indicate the presence of residual disease.

Breast Cancer

Non-limiting examples of serum tumor markers useful in the present invention for the detection of breast cancer include, but is not limited to carcinoembryonic antigen (CEA) and MUC-1 (CA 15.3). Serum CEA and CA15.3 levels are elevated in patients with node involvement compared to patients without node involvement, and in patients with larger tumors compared to smaller tumors. Normal range cutoff points (upper limit) are 5–10 mg/L for CEA and 35–60 u/ml for CA15.3. Additional specificity (99.3%) is gained by confirming serum levels with two serial increases of more than 15%.

Ovarian Cancer

A non-limiting example of a tumor marker useful in the present invention for the detection of ovarian cancer is CA125. Normally, women have serum CA125 levels between 0–35 kU/L; 99% of post-menopausal women have levels below 20 kU/L. Serum concentration of CA125 after chemotherapy is a strong predictor of outcome as elevated CA125 levels are found in roughly 80% of all patients with epithelial ovarian cancer. Further, prolonged CA125 half-life or a less than 7-fold decrease during early treatment is also a predictor of poor disease prognosis.

Gastrointestinal Cancers

A non-limiting example of a tumor marker useful in the present invention for the detection of colon cancer is carcinoembryonicantigen (CEA). CEA is a glycoprotein produced during embryonal and fetal development and has a high sensitivity for advanced carcinomas including those of the colon, breast, stomach and lung. High pre- or postoperative concentrations (>2.5 ng/ml) of CEA are associated with worse prognosis than are low concentrations. Further, some studies in the literature report that slow rising CEA levels indicates local recurrence while rapidly increasing levels suggests hepatic metastasis.

Lung Cancer

Examples of serum markers useful in the present invention to monitor lung cancer therapy include, but are not limited to, CEA, cytokeratin 19 fragments (CYFRA 21-1), and Neuron Specific Enolase (NSE).

NSE is a glycolytic isoenzyme of enolase produced in central and peripheral neurons and malignant tumors of neuroectodermal origin. At diagnosis, NSE concentrations greater than 25 ng/mL are suggestive of malignancy and lung cancer while concentrations greater than 100 ng/mL are suggestive of small cell lung cancer.

CYFRA 21-1 is a tumor marker test which uses two specific monoclonal antibodies against a cytokeratin 19 fragment. At diagnosis, CYFRA 21-1 concentrations greater than 10 ng/mL are suggestive of malignancy while concentrations greater than 30 ng/mL are suggestive of lung cancer.

Accordingly, dosing of the matrix metalloproteinase inhibitor and antineoplastic agent may be determined and adjusted based on measurement of tumor markers in body fluids or tissues, particularly based on tumor markers in serum. For example, a decrease in serum marker level relative to baseline serum marker prior to administration of the matrix metalloproteinase inhibitor and antineoplastic agent indicates a decrease in cancer-associated changes and provides a correlation with inhibition of the cancer. In one embodiment, therefore, the method of the present invention comprises administering the matrix metalloproteinase inhibitor and antineoplastic agent at doses that in combination result in a decrease in one or more tumor markers, particularly a decrease in one or more serum tumor markers, in the mammal relative to baseline tumor marker levels.

Similarly, decreasing tumor marker concentrations or serum half lives after administration of the combination indicates a good prognosis, while tumor marker concentrations which decline slowly and do not reach the normal reference range predict residual tumor and poor prognosis. Further, during follow-up therapy, increases in tumor marker concentration predicts recurrent disease many months before clinical manifestation.

In addition to the above examples, Table No. 4, below, lists several references, hereby individually incorporated by reference herein, that describe tumor markers and their use in detecting and monitoring tumor growth and progression.

TABLE 4

Tumor marker references.

European Group on Tumor Markers Publications Committee. Consensus Recommendations. Anticancer Research 19: 2785–2820 (1999)
Human Cytogenetic Cancer Markers. Sandra R. Wolman and Stewart Sell (eds.). Totowa, New Jersey: Humana Press. 1997
Cellular Markers of Cancer. Carleton Garrett and Stewart Sell (eds.). Totowa, New Jersey: Human Press. 1995

Also included in the combination of the invention are the isomeric forms, prodrugs and tautomers of the described compounds and the pharmaceutically-acceptable salts thereof. Illustrative pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, b-hydroxybutyric, galactaric and galacturonic acids.

Suitable pharmaceutically-acceptable base addition salts of compounds of the present invention include metallic ion salts and organic ion salts. More preferred metallic ion salts include, but are not limited to appropriate alkali metal (group Ia) salts, alkaline earth metal (group Ia) salts and other physiological acceptable metal ions. Such salts can be made from the ions of aluminum, calcium, lithium, magnesium, potassium, sodium and zinc. Preferred organic salts can be made from tertiary amines and quaternary ammonium salts, including in part, trimethylamine, diethylamine, N,N'-dibenzylethylenediamine, chloroprocaine, choline, diethanolamine, ethylenediamine, meglumine (N-methylglucamine) and procaine. All of the above salts can be prepared by those skilled in the art by conventional means from the corresponding compound of the present invention.

Administration Regimen

Any effective treatment regimen can be utilized and readily determined and repeated as necessary to effect treatment. In clinical practice, the compositions containing an MMP inhibitor alone or in combination with other therapeutic agents are administered in specific cycles until a response is obtained.

For patients who initially present without advanced or metastatic cancer, an MMP inhibitor in combination with another antiangiogenic agent or one or more anticancer agents may be used as an immediate initial therapy prior to surgery, chemotherapy, or radiation therapy, and as a continuous post-treatment therapy in patients at risk for recurrence or metastasis (for example, in adenocarcinoma of the prostate, risk for metastasis is based upon high PSA, high Gleason's score, locally extensive disease, and/or pathological evidence of tumor invasion in the surgical specimen). The goal in these patients is to inhibit the growth of potentially metastatic cells from the primary tumor during surgery or radiotherapy and inhibit the growth of tumor cells from undetectable residual primary tumor.

For patients who initially present with advanced or metastatic cancer, an MMP inhibitor in combination with another MMP inhibitor or one or more anticancer agents of the present invention is used as a continuous supplement to, or possible replacement for hormonal ablation. The goal in these patients is to slow or prevent tumor cell growth from both the untreated primary tumor and from the existing metastatic lesions.

In addition, the invention may be particularly efficacious during post-surgical recovery, where the present compositions and methods may be particularly effective in lessening the chances of recurrence of a tumor engendered by shed cells that cannot be removed by surgical intervention.

Combinations with Other Treatments

MMP inhibitors may be used in conjunction with other treatment modalities, including, but not limited to surgery and radiation, hormonal therapy, chemotherapy, immunotherapy, antiangiogenic therapy and cryotherapy. The present invention may be used in conjunction with any current or future therapy.

The following discussion highlights some agents in this respect, which are illustrative, not limitative. A wide variety of other effective agents also may be used.

Surgery and Radiation

In general, surgery and radiation therapy are employed as potentially curative therapies for patients under 70 years of age who present with clinically localized disease and are expected to live at least 10 years.

For example, approximately 70% of newly diagnosed prostate cancer patients fall into this category. Approximately 90% of these patients (65% of total patients) undergo surgery, while approximately 10% of these patients (7% of total patients) undergo radiation therapy. Histopathological examination of surgical specimens reveals that approximately 63% of patients undergoing surgery (40% of total patients) have locally extensive tumors or regional (lymph node) metastasis that was undetected at initial diagnosis. These patients are at a significantly greater risk of recurrence. Approximately 40% of these patients will actually develop recurrence within five years after surgery. Results after radiation are even less encouraging. Approximately 80% of patients who have undergone radiation as their primary therapy have disease persistence or develop recurrence or metastasis within five years after treatment. Currently, most of these surgical and radiotherapy patients generally do not receive any immediate follow-up therapy. Rather, for example, they are monitored frequently for elevated Prostate Specific Antigen ("PSA"), which is the primary indicator of recurrence or metastasis prostate cancer.

Thus, there is considerable opportunity to use the present invention in conjunction with surgical intervention.

Hormonal Therapy

Hormonal ablation is the most effective palliative treatment for the 10% of patients presenting with metastatic prostate cancer at initial diagnosis. Hormonal ablation by medication and/or orchiectomy is used to block hormones that support the further growth and metastasis of prostate cancer. With time, both the primary and metastatic tumors of virtually all of these patients become hormone-independent and resistant to therapy. Approximately 50% of patients presenting with metastatic disease die within three years after initial diagnosis, and 75% of such patients die within five years after diagnosis. Continuous supplementation with NAALADase inhibitor based drugs are used to prevent or reverse this potentially metastasis-permissive state.

Among hormones which may be used in combination with the present inventive compounds, diethylstilbestrol (DES), leuprolide, flutamide, cyproterone acetate, ketoconazole and amino glutethimide are preferred.

Immunotherapy

The MMP inhibitors may also be used in combination with monoclonal antibodies in treating cancer. For example monoclonal antibodies may be used in treating prostate cancer. A specific example of such an antibody includes cell membrane-specific anti-prostate antibody.

The present invention may also be used with immunotherapies based on polyclonal or monoclonal antibody-derived reagents, for instance. Monoclonal antibody-based reagents are most preferred in this regard. Such reagents are well known to persons of ordinary skill in the art. Radiolabelled monoclonal antibodies for cancer therapy, such as the recently approved use of monoclonal antibody conjugated with strontium-89, also are well known to persons of ordinary skill in the art.

Antiangiogenic Therapy

The MMP inhibitors may also be used in combination with other antiangiogenic agents in treating cancer. Antiangiogenic agents include but are not limited to COX-2 inhibitors, integrin antagonists, angiostatin, endostatin, thrombospondin-1, and interferon alpha. Examples of preferred antiangiogenic agents include, but are not limited to vitaxin, celecoxib, rofecoxib, JTE-522, EMD-121974, and D-2163 (BMS-275291).

Cryotherapy

Cryotherapy recently has been applied to the treatment of some cancers. Methods and compositions of the present invention also could be used in conjunction with an effective therapy of this type.

All of the various cell types of the body can be transformed into benign or malignant neoplasia or tumor cells and are contemplated as objects of the invention. A "benign" tumor cell denotes the non-invasive and non-metastasized state of a neoplasm. In man the most frequent neoplasia site is lung, followed by colorectal, breast, prostate, bladder, pancreas, and then ovary. Other prevalent types of cancer include leukemia, central nervous system cancers, including brain cancer, melanoma, lymphoma, erythroleukemia, uterine cancer, and head and neck cancer. Examples 1 through 8 are provided to illustrate contemplated therapeutic combinations, and are not intended to limit the scope of the invention.

Illustrations

The following non-limiting illustrative examples (1 through 9) describe various cancer diseases and therapeutic approaches that may be used in the present invention, and are for illustrative purposes only. Preferred MMP inhibitors of the below non-limiting illustrations include but are not limited to Compound M1, Compound M2, Compound M3, Compound M4, Compound M5, Compound M6, Compound M7, Compound M8, Marimastat, Bay-12-9566, AG-3340, Metastat, and D-2163 (BMS-275291).

Example 1

Lung Cancer

In many countries including Japan, Europe and America, the number of patients with lung cancer is fairly large and continues to increase year after year and is the most frequent cause of cancer death in both men and women. Although there are many potential causes for lung cancer, tobacco use, and particularly cigarette smoking, is the most important. Additionally, etiologic factors such as exposure to asbestos, especially in smokers, or radon are contributory factors. Also occupational hazards such as exposure to uranium have been identified as an important factor. Finally, genetic factors have also been identified as another factor that increase the risk of cancer.

Lung cancers can be histologically classified into non-small cell lung cancers (e.g. squamous cell carcinoma (epidermoid), adenocarcinoma, large cell carcinoma (large cell anaplastic), etc.) and small cell lung cancer (oat cell). Non-small cell lung cancer (NSCLC) has different biological properties and responses to chemotherapeutics from those of small cell lung cancer (SCLC). Thus, chemotherapeutic formulas and radiation therapy are different between these two types of lung cancer.

Non-Small Cell Lung Cancer

Where the location of the non-small cell lung cancer tumor can be easily excised (stage I and II disease) surgery is the first line of therapy and offers a relatively good chance for a cure. However, in more advanced disease (stage IIIa and greater), where the tumor has extended to tissue beyond the bronchopulmonary lymph nodes, surgery may not lead to complete excision of the tumor. In such cases, the patient's chance for a cure by surgery alone is greatly diminished. Where surgery will not provide complete removal of the NSCLC tumor, other types of therapies must be utilized.

Today radiation therapy is the standard treatment to control unresectable or inoperable NSCLC. Improved results have been seen when radiation therapy has been combined with chemotherapy, but gains have been modest and the search continues for improved methods of combining modalities.

Radiation therapy is based on the principle that high-dose radiation delivered to a target area will result in the death of reproductive cells in both tumor and normal tissues. The radiation dosage regimen is generally defined in terms of radiation absorbed dose (rad), time and fractionation, and must be carefully defined by the oncologist. The amount of radiation a patient receives will depend on various consideration but the two most important considerations are the location of the tumor in relation to other critical structures or organs of the body, and the extent to which the tumor has spread. A preferred course of treatment for a patient undergoing radiation therapy for NSCLC will be a treatment schedule over a 5 to 6 week period, with a total dose of 50 to 60 Gy administered to the patient in a single daily fraction of 1.8 to 2.0 Gy, 5 days a week. A Gy is an abbreviation for Gray and refers to 100 rad of dose.

However, as NSCLC is a systemic disease, and radiation therapy is a local modality, radiation therapy as a single line of therapy is unlikely to provide a cure for NSCLC, at least for those tumors that have metastasized distantly outside the zone of treatment. Thus, the use of radiation therapy with other modality regimens have important beneficial effects for the treatment of NSCLC.

Generally, radiation therapy has been combined temporally with chemotherapy to improve the outcome of treatment. There are various terms to describe the temporal relationship of administering radiation therapy in combination with MMP inhibitors and chemotherapy, and the following examples are the preferred treatment regimens and are provided for illustration only and are not intended to limit the use of other combinations. "Sequential" therapy refers to the administration of chemotherapy and/or MMP therapy and/or radiation therapy separately in time in order to allow the separate administration of either chemotherapy and/or MMP inhibitors, and/or radiation therapy. "Concomitants therapy refers to the administration of chemotherap" and/or a MMP inhibitor, and/or radiation therapy on the same day. Finally, "alternating therapy refers to the administration of radiation therapy on the days in which chemotherapy and/or MMP inhibitor would not have been administered if it was given alone.

It is reported that advanced non-small cell lung cancers do not respond favorably to single-agent chemotherapy and useful therapies for advanced inoperable cancers have been limited. (Journal of Clinical oncology, vol. 10, pp. 829–838 (1992)).

Japanese Patent Kokai 5-163293 refers to some specified antibiotics of 16-membered-ring macrolides as a drug delivery carrier capable of transporting anthoracycline-type anticancer drugs into the lungs for the treatment of lung cancers. However, the macrolide antibiotics specified herein are disclosed to be only a drug carrier, and there is no reference to the therapeutic use of macrolides against non-small cell lung cancers.

WO 93/18,652 refers to the effectiveness of the specified 16-membered-ring macrolides such as bafilomycin, etc. in treating non-small cell lung cancers, but they have not yet been clinically practicable.

Pharmacology, vol. 41, pp. 177–183 (1990) describes that a long-term use of erythromycin increases productions of interleukins 1, 2 and 4, all of which contribute to host immune responses, but there is no reference to the effect of this drug on non-small cell lung cancers.

Teratogenesis, Carcinogenesis, and Mutagenesis, vol. 10, pp. 477–501 (1990) describes that some of antimicrobial drugs can be used as an anticancer agent, but does not refer to their application to non-small cell lung cancers.

In addition, interleukins are known to have an antitumor effect, but have not been reported to be effective against non-small cell lung cancers.

Any 14- or 15-membered-ring macrolides have not been reported to be effective against non-small cell lung cancers.

However, several chemotherapeutic agents have been shown to be efficacious against NSCLC. Preferred chemotherapeutic agents that can be used in the present invention against NSCLC include etoposide, carboplatin, methotrexate, 5-Fluorouracil, epirubicin, doxorubicin, taxol, inhibitor of normal mitotic activity; and cyclophosphamide. Even more preferred chemotherapeutic agents active against NSCLC include cisplatin, ifosfamide, mitomycin C, epirubicin, vinblastine, and vindesine.

Other agents that are under investigation for use against NSCLC include: camptothecins, a topoisomerase 1 inhibitor; navelbine (vinorelbine), a microtubule assebly inhibitor; gemcitabine, a deoxycytidine analogue; fotemustine, a nitrosourea compound; and edatrexate, a antifol.

The overall and complete response rates for NSCLC has been shown to increase with use of combination chemotherapy as compared to single-agent treatment. Haskel C M: Chest. 99: 1325, 1991; Bakowski M T: Cancer Treat Rev 10:159, 1983; Joss R A: Cancer Treat Rev 11:205, 1984.

A preferred therapy for the treatment of NSCLC is a combination of therapeutically effective amounts of one or more MMP inhibitors in combination with the following combinations of antineoplastic agents: 1) itosfamide, cisplatin, etoposide; 2) cyclophoshamide, doxorubicin, cisplatin; 3) isofamide, carboplatin, etoposide; 4) bleomycin, etoposide, cisplatin; 5) isofamide, mitomycin, cisplatin; 6) cisplatin, vinblastine; 7) cisplatin, vindesine; 8) mitomycin C, vinblastine, cisplatin; 9) mitomycin C, vindesine, cisplatin; 10) isofamide, etoposide; 11) etoposide, cisplatin; 12) isofamide, mitomycin C; 13) flurouracil, cisplatin, vinblastine; 14) carboplatin, etoposide; or radiation therapy.

Accordingly, apart from the conventional concept of anticancer therapy, there is a strong need for the development of therapies practicably effective for the treatment of non-small cell lung cancers.

Small Cell Lung Cancer

Approximately 15 to 20 percent of all cases of lung cancer reported worldwide is small cell lung cancer (SCLC). Ihde DC: Cancer 54:2722, 1984. Currently, treatment of SCLC incorporates multi-modal therapy, including chemotherapy, radiation therapy and surgery. Response rates of localized or disseminated SCLC remain high to systemic chemotherapy, however, persistence of the primary tumor and persistence of the tumor in the associated lymph nodes has led to the integration of several therapeutic modalities in the treatment of SCLC.

A preferred therapy for the treatment of lung cancer is a combination of therapeutically effective amounts of one or more MMP inhibitors in combination with the following antineoplastic agents: vincristine, cisplatin, carboplatin, cyclophosphamide, epirubicin (high dose), etoposide (VP-16) I.V., etoposide (VP-16) oral, isofamide, teniposide (VM-26), and doxorubicin. Other preferred single-agents chemotherapeutic agents that may be used in the present invention include BCNU (carmustine), vindesine, hexamethylmelamine (altretamine), methotrexate, nitrogen mustard, and CCNU (lomustine). Other chemotherapeutic agents under investigation that have shown activity againe SCLC include iroplatin, gemcitabine, lonidamine, and taxol. Single-agent chemotherapeutic agents that have not shown activity against SCLC include mitoguazone, mitomycin C, aclarubicin, diaziquone, bisantrene, cytarabine, idarubicin, mitomxantrone, vinblastine, PCNU and esorubicin.

The poor results reported from single-agent chemotherapy has led to use of combination chemotherapy.

A preferred therapy for the treatment of NSCLC is a combination of therapeutically effective amounts of one or more MMP inhibitors in combination with the following combinations of antineoplastic agents: 1) etoposide (VP-16), cisplatin; 2) cyclophosphamide, adrianmycin [(doxorubicin), vincristine, etoposide (VP-16)]; 3) Cyclophosphamide, adrianmycin(doxorubicin), vincristine; 4) Etoposide (VP-16), ifosfamide, cisplatin; 5) etoposide (VP-16), carboplatin; 6) cisplatin, vincristine (Oncovin), doxorubicin, etoposide.

Additionally, radiation therapy in conjunction with the preferred combinations of MMP inhibitors and/or systemic chemotherapy is contemplated to be effective at increasing the response rate for SCLC patients. The typical dosage regimen for radiation therapy ranges from 40 to 55 Gy, in 15 to 30 fractions, 3 to 7 times week. The tissue volume to be irradiated is determined by several factors and generally the hilum and subcarnial nodes, and bilateral mdiastinal nodes up to the thoracic inlet are treated, as well as the primary tumor up to 1.5 to 2.0 cm of the margins.

Example 2

Colorectal Cancer

Survival from colorectal cancer depends on the stage and grade of the tumor, for example precursor adenomas to metastatic adenocarcinoma. Generally, colorectal cancer can be treated by surgically removing the tumor, but overall survival rates remain between 45 and 60 percent. Colonic excision morbidity rates are fairly low and is generally associated with the anastomosis and not the extent of the removal of the tumor and local tissue. In patients with a high risk of reoccurrence, however, chemotherapy has been incorporated into the treatment regimen in order to improve survival rates.

Tumor metastasis prior to surgery is generally believed to be the cause of surgical intervention failure and up to one year of chemotherapy is required to kill the non-excised tumor cells. As severe toxicity is associated with the chemotherapeutic agents, only patients at high risk of recurrence are placed on chemotherapy following surgery. Thus, the incorporation of an antiangiogenesis inhibitor into the management of colorectal cancer will play an important role in the treatment of colorectal cancer and lead to overall improved survival rates for patients diagnosed with colorectal cancer.

A preferred combination therapy for the treatment of colorectal cancer is surgery, followed by a regimen of one or more chemotherapeutic agents and an MMP inhibitor cycled over a one year time period. A more preferred combination therapy for the treatment of colorectal cancer is a regimen of one or more MMP inhibitors, followed by surgical removal of the tumor from the colon or rectum and then followed be a regimen of one or more chemotherapeutic agents and one or more MMP inhibitors, cycled over a one year time period. An even more preferred therapy for the treatment of colon cancer is a combination of therapeutically effective amounts of one or more MMP inhibitors.

A more preferred therapy for the treatment of colon cancer is a combination of therapeutically effective amounts of one or more MMP inhibitors in combination with the following antineoplastic agents: fluorouracil, and Levamisole. Preferably, fluorouracil and Levamisole are used in combination.

Example 3

Breast Cancer

Today, among women in the United States, breast cancer remains the most frequent diagnosed cancer. One in 8 women in the United States are at risk of developing breast cancer in their lifetime. Age, family history, diet, and genetic factors have been identified as risk factors for breast cancer. Breast cancer is the second leading cause of death among women.

Different chemotherapeutic agents are known in art for treating breast cancer. Cytotoxic agents used for treating breast cancer include doxorubicin, cyclophosphamide, methotrexate, 5-fluorouracil, mitomycin C, mitoxantrone, taxol, and epirubicin. CANCER SURVEYS, Breast Cancer volume 18, Cold Spring Harbor Laboratory Press, 1993.

In the treatment of locally advanced noninflammatory breast cancer, MMP inhibitors can be used to treat the disease in combination with other MMP inhibitors, or in combination with surgery, radiation therapy, chemotherapeutic agents, or with other antiangiogenic agents. Preferred combinations of chemotherapeutic agents, radiation therapy and surgery that can be used in combination with the present invention include, but are not limited to the following combinations: 1) doxorubicin, vincristine, radical mastectomy; 2) doxorubicin, vincristine, radiation therapy; 3) cyclophosphamide, doxorubicin, 5-flourouracil, vincristine, prednisone, mastecomy; 4) cyclophosphamide, doxorubicin, 5-flourouracil, vincristine, prednisone, radiation therapy; 5) cyclophosphamide, doxorubicin, 5-flourouracil, premarin, tamoxifen, radiation therapy for pathologic complete response; 6) cyclophosphamide, doxorubicin, 5-flourouracil, prematin, tamoxifen, mastectomy, radiation therapy for pathologic partial response; 7) mastectomy, radiation therapy, levamisole; 8) mastectomy, radiation therapy; 9) mastectomy, vincristine, doxorubicin, cyclophosphamide, levamisole; 10) mastectomy, vincristine, doxorubicin, cyclophosphamide; 11) mastecomy, cyclophosphamide, doxorubicin, 5-fluorouracil, tamoxifen, halotestin, radiation therapy; 12) mastecomy, cyclophosphamide, doxorubicin, 5-fluorouracil, tamoxifen, halotestin.

In the treatment of locally advanced inflammatory breast cancer, MMP inhibitors can be used to treat the disease in combination with other antiangiogenic agents, or in combination with surgery, radiation therapy or with chemotherapeutic agents. Preferred combinations of chemotherapeutic agents, radiation therapy and surgery that can be used in combination with the present invention include, but or not limited to the following combinations: 1) cyclophosphamide, doxorubicin, 5-fluorouracil, radiation therapy; 2) cyclophosphamide, doxorubicin, 5-fluorouracil, mastectomy, radiation therapy; 3) 5-flurouracil, doxorubicin, clyclophosphamide, vincristine, prednisone, mastectomy, radiation therapy; 4) 5-flurouracil, doxorubicin, clyclophosphamide, vincristine, mastectomy, radiation therapy; 5) cyclophosphamide, doxorubicin, 5-fluorouracil, vincristine, radiation therapy; 6) cyclophosphamide, doxorubicin, 5-fluorouracil, vincristine, mastectomy, radiation therapy; 7) doxorubicin, vincristine, methotrexate, radiation therapy, followed by vincristine, cyclophosphamide, 5-florouracil; 8) doxorubicin, vincristine, cyclophosphamide, methotrexate, 5-florouracil, radiation therapy, followed by vincristine, cyclophosphamide, 5-florouracil; 9) surgery, followed by cyclophosphamide, methotrexate, 5-fluorouracil, predinsone, tamoxifen, followed by radiation therapy, followed by cyclophosphamide, methotrexate, 5-fluorouracil, predinsone, tamoxifen, doxorubicin, vincristine, tarnoxifen; 10) surgery, followed by cyclophosphamide, methotrexate, 5-fluorouracil, followed by radiation therapy, followed by cyclophosphamide, methotrexate, 5-fluorouracil, predinsone, tamoxifen, doxorubicin, vincristine, tamoxifen; 11) surgery, followed by cyclophosphamide, methotrexate, 5-fluorouracil, predinsone, tamoxifen, followed by radiation therapy, followed by cyclophosphamide, methotrexate, 5-fluorouracil, doxorubicin, vincristine, tamoxifen; 12) surgery, followed by cyclophosphamide, methotrexate, 5-fluorouracil, followed by radiation therapy, followed by cyclophosphamide, methotrexate, 5-fluorouracil, predinsone, tamoxifen, doxorubicin, vincristine; 13) surgery, followed by cyclophosphamide, methotrexate, 5-fluorouracil, predinsone, tamoxifen, followed by radiation therapy, followed by cyclophosphamide, methotrexate, 5-fluorouracil, predinsone, tamoxifen, doxorubicin, vincristine, tamoxifen; 14) surgery, followed by cyclophosphamide, methotrexate, 5-fluorouracil, followed by radiation therapy, followed by cyclophosphamide, methotrexate, 5-fluorouracil, predinsone, tamoxifen, doxorubicin, vincristine; 15) surgery, followed by cyclophosphamide, methotrexate, 5-fluorouracil, predinsone, tamoxifen, followed by radiation therapy, followed by cyclophosphamide, methotrexate, 5-fluorouracil, doxorubicin, vincristine; 16) 5-florouracil, doxorubicin, cyclophosphamide followed by mastectomy, followed by 5-florouracil, doxorubicin, cyclophosphamide, followed by radiation therapy.

In the treatment of metastatic breast cancer, MMP inhibitors can be used to treat the disease in combination with other MMP inhibitors, or in combination with surgery, radiation therapy or with chemotherapeutic agents. Preferred combinations of chemotherapeutic agents that can be used in combination with the angiogenesis inhibitors of the present invention include, but are not limited to the following combinations: 1) cyclosphosphamide, methotrexate, 5-fluorouracil; 2) cyclophosphamide, adriamycin, 5-fluorouracil; 3) cyclosphosphamide, methotrexate, 5-flurouracil, vincristine, prednisone; 4) adriamycin, vincristine; 5) thiotepa, adriamycin, vinblastine; 6) mitomycin, vinblastine; 7) cisplatin, etoposide.

Example 4

Prostate Cancer

Prostate cancer is now the leading form of cancer among men and the second most frequent cause of death from cancer in men. It is estimated that more than 165,000 new cases of prostate cancer were diagnosed in 1993, and more than 35,000 men died from prostate cancer in that year. Additionally, the incidence of prostate cancer has increased by 50% since 1981, and mortality from this disease has continued to increase. Previously, most men died of other illnesses or diseases before dying from their prostate cancer. We now face increasing morbidity from prostate cancer as men live longer and the disease has the opportunity to progress.

Current therapies for prostate cancer focus exclusively upon reducing levels of dihydrotestosterone to decrease or prevent growth of prostate cancer. In addition to the use of digital rectal examination and transrectal ultrasonography, prostate-specific antigen (PSA) concentration is frequently used in the diagnosis of prostate cancer.

A preferred therapy for the treatment of prostate cancer is a combination of therapeutically effective amounts of one or more MMP inhibitors.

U.S. Pat. No. 4,472,382 discloses treatment of benign prostatic hyperplasia (BPH) with an antiandrogen and certain peptides which act as LH-RH agonists.

U.S. Pat. No. 4,596,797 discloses aromatase inhibitors as a method of prophylaxis and/or treatment of prostatic hyperplasia.

U.S. Pat. No. 4,760,053 describes a treatment of certain cancers which combines an LHRH agonist with an antiandrogen and/or an antiestrogen and/or at least one inhibitor of sex steroid biosynthesis.

U.S. Pat. No. 4,775,660 discloses a method of treating breast cancer with a combination therapy which may include surgical or chemical prevention of ovarian secretions and administering an antiandrogen and an antiestrogen.

U.S. Pat. No. 4,659,695 discloses a method of treatment of prostate cancer in susceptible male animals including humans whose testicular hormonal secretions are blocked by surgical or chemical means, e.g. by use of an LHRH agonist, which comprises administering an antiandrogen, e.g. flutamide, in association with at least one inhibitor of sex steroid biosynthesis, e.g. aminoglutethimide and/or ketoconazole.

Prostate Specific Antigen

One well known prostate cancer marker is Prostate Specific Antigen (PSA). PSA is a protein produced by prostate cells and is frequently present at elevated levels in the blood of men who have prostate cancer. PSA has been shown to correlate with tumor burden, serve as an indicator of metastatic involvement, and provide a parameter for following the response to surgery, irradiation, and androgen replacement therapy in prostate cancer patients. It should be noted that Prostate Specific Antigen (PSA) is a completely different protein from Prostate Specific Membrane Antigen (PSMA). The two proteins have different structures and functions and should not be confused because of their similar nomenclature.

Prostate Specific Membrane Antigen (PSMA)

In 1993, the molecular cloning of a prostate-specific membrane antigen (PSMA) was reported as a potential prostate carcinoma marker and hypothesized to serve as a target for imaging and cytotoxic treatment modalities for prostate cancer. Antibodies against PSMA have been described and examined clinically for diagnosis and treatment of prostate cancer. In particular, Indium-111 labeled PSMA antibodies have been described and examined for diagnosis of prostate cancer and itrium-labelled PSMA antibodies have been described and examined for the treatment of prostate cancer.

Example 5

Bladder Cancer

The classification of bladder cancer is divided into three main classes: 1) superficial disease, 2) muscle-invasive disease, and 3) metastatic disease.

Currently, transurethral resection (TUR), or segmental resection, account for first line therapy of superficial bladder cancer, i.e., disease confined to the mucosa or the lamina propria. However, intravesical therapies are necessary, for example, for the treatment of high-grade tumors, carcinoma in situ, incomplete resections, recurrences, and multifocal papillary. Recurrence rates range from up to 30 to 80 percent, depending on stage of cancer.

Therapies that are currently used as intravesical therapies include chemotherapy, immuontherapy, bacille Calmette-Guerin (BCG) and photodynamic therapy. The main objective of intravesical therapy is twofold: to prevent recurrence in high-risk patients and to treat disease that cannot by resected. The use of intravesical therapies must be balanced with its potentially toxic side effects. Additionally, BCG requires an unimpaired-immune system to induce an anti-tumor effect. Chemotherapeutic agents that are known to be inactive against superficial bladder cancer include Cisplatin, actinomycin D, 5-fluorouracil, bleomycin, and cyclophosphamide methotrxate.

In the treatment of superficial bladder cancer, MMP inhibitors can be used to treat the disease in combination with other MMP inhibitors, or in combination with surgery (TUR), chemotherapy and intravesical therapies.

A preferred therapy for the treatment of superficial bladder cancer is a combination of therapeutically effective amounts of one or more MMP inhibitors in combination with: thiotepa (30 to 60 mg/day), mitomycin C (20 to 60 mg/day), and doxorubicin (20 to 80 mg/day).

A preferred intravesicle immunotherapeutic agent that may be used in the present invention is BCG. A preferred daily dose ranges from 60 to 120 mg, depending on the strain of the live attenuated tuberculosis organism used.

A preferred photodynamic therapeutic agent that may be used with the present invention is Photofrin I, a photosensitizing agent, administered intravenously. It is taken up by the low-density lipoprotein receptors of the tumor cells and is activated by exposure to visible light. Additionally, neomydium YAG laser activation generates large amounts of cytotoxic free radicals and singlet oxygen.

In the treatment of muscle-invasive bladder cancer, MMP inhibitors can be used to treat the disease in combination with other MMP inhibitors, or in combination with surgery (TUR), intravesical chemotherapy, radiation therapy, and radical cystectomy with pelvic lymph node dissection.

A preferred radiation dose for the treatment of bladder cancer is between 5,000 to 7,000 cGY in fractions of 180 to 200 cGY to the tumor. Additionally, 3,500 to 4,700 cGY total dose is administered to the normal bladder and pelvic contents in a four-field technique. Radiation therapy should be considered only if the patient is not a surgical candidate, but may be considered as preoperative therapy.

A preferred combination of surgery and chemotherapeutic agents that can be used in combination with the MMP inhibitors of the present invention is cystectomy in conjunction with five cycles of cisplatin (70 to 100 mg/m(square)); doxorubicin (50 to 60 mg/m(square); and cyclophosphamide (500 to 600 mg/m(square).

A more preferred therapy for the treatment of superficial bladder cancer is a combination of therapeutically effective amounts of one or more MMP inhibitors.

An even more preferred combination for the treatment of superficial bladder cancer is a combination of therapeutically effective amounts of one or more MMP inhibitors in combination with the following combinations of antineoplastic agents: 1) cisplatin, doxorubicin, cyclophosphamide; and 2) cisplatin, 5-fluorouracil. An even more preferred combination of chemotherapeutic agents that can be used in combination with radiation therapy and MMP inhibitors is a combination of cisplatin, methotrexate, vinblastine.

Currently no curative therapy exists for metastatic bladder cancer. The present invention contemplates an effective treatment of bladder cancer leading to improved tumor inhibition or regression, as compared to current therapies.

In the treatment of metastatic bladder cancer, MMP inhibitors can be used to treat the disease in combination with other MMP inhibitors, or in combination with surgery, radiation therapy or with chemotherapeutic agents.

A preferred therapy for the treatment of metastatic bladder cancer is a combination of therapeutically effective amounts of one or more MMP inhibitors.

A more preferred combination for the treatment of metastatic bladder cancer is a combination of therapeutically effective amounts of one or more MMP inhibitors in combination with the following antineoplasitc agents: 1) cisplatin and methotrexate; 2) doxorubicin, vinblastine, cyclophoshamide, and 5-fluorouracil; 3) vinblastine, doxorubicin, cisplatin, methotrexate; 4) vinblastine, cisplatin, methotrexate; 5) cyclophosphamide, doxorubicin, cisplatin; 6) 5-fluorouracil, cisplatin.

Example 6

Pancreas Cancer

Approximately 2% of new cancer cases diagnoses in the United States is pancreatic cancer. Pancreatic cancer is generally classified into two clinical types: 1) adenocarcinoma (metastatic and non-metastatic), and 2) cystic neoplasms (serous cystadenomas, mucinous cystic neoplasms, papilary cystic neoplasms, acinar cell systadenocarcinoma, cystic choriocarcinoma, cystic teratomas, angiomatous neoplasms).

Preferred combinations of therapy for the treatment of non-metastatic adenocarcinoma that may be used in the present invention include the use of an MMP inhibitor along with preoperative bilary tract decompression (patients presenting with obstructive jaundice); surgical resection, including standard resection, extended or radial resection and distal pancreatectomy (tumors of body and tail); adjuvant radiation; antiangiogenic therapy; and chemotherapy.

For the treatment of metastatic adenocarcinoma, a preferred combination therapy consists of an MMP inhibitor of the present invention in combination with continuous treatment of 5-fluorouracil, followed by weekly cisplatin therapy.

A more preferred combination therapy for the treatment of cystic neoplasms is the use of an MMP inhibitor along with resection.

Example 7

Ovary Cancer

Celomic epithelial carcinoma accounts for approximately 90% of ovarian cancer cases. A preferred therapy for the treatment of ovary cancer is a combination of therapeutically effective amounts of one or more MMP inhibitors.

Preferred single agents that can be used in combination with an MMP inhibitor include, but are not limited to: alkylating agents, ifosfamide, cisplatin, carboplatin, taxol, doxorubicin, 5-fluorouracil, methotrexate, mitomycin, hexamethylmelamine, progestins, antiestrogens, prednimustine, dihydroxybusulfan, galactitol, interferon alpha, and interferon gama.

Preferred combinations for the treatment of celomic epithelial carcinoma is a combination of therapeutically effective amounts of one or more MMP inhibitors in combination with the following combinations of antineoplastic agents: 1)

cisplatin, doxorubicin, cyclophosphamide; 2) hexamthylmelamine, cyclosphamide, doxorubicin, cisplatin; 3) cyclophosphamide, hexamehtylmelamine, 5-flurouracil, cisplatin; 4) melphalan, hexamethylmelamine, cyclophosphamide; 5) melphalan, doxorubicin, cyclophosphamide; 6) cyclophosphamide, cisplatin, carboplatin; 7) cyclophosphamide, doxorubicin, hexamethylmelamine, cisplatin; 8) cyclophosphamide, doxorubicin, hexamethylmelamine, carboplatin; 9) cyclophosphamide, cisplatin; 10) hexamethylmelamine, doxorubicin, carboplatin; 11) cyclophosphamide, hexamethlmelamine, doxorubicin, cisplatin; 12) carboplatin, cyclophosphamide; 13) cisplatin, cyclophosphamide.

Germ cell ovarian cancer accounts for approximately 5% of ovarian cancer cases. Germ cell ovarian carcinomas are classified-into two main groups: 1) dysgerminoma, and nondysgerminoma. Nondysgerminoma is further classified into teratoma, endodermal sinus tumor, embryonal carcinoma, chloricarcinoma, polyembryoma, and mixed cell tumors.

A preferred therapy for the treatment of germ cell carcinoma is a combination of therapeutically effective amounts of one or more MMP inhibitors.

A more preferred therapy for the treatment of germ cell carcinoma is a combination of therapeutically effective amounts of one or more MMP inhibitors in combination with one or more of the following combinations of antineoplastic agents: 1) vincristine, actinomycin D, cyclophosphamide; 2) bleomycin, etoposide, cisplatin; 3) vinblastine, bleomycin, cisplatin.

Cancer of the fallopian tube is the least common type of ovarian cancer, accounting for approximately 400 new cancer cases per year in the United States. Papillary serous adenocarcinoma accounts for approximately 90% of all malignancies of the ovarian tube.

A preferred therapy for the treatment of fallopian tube cancer is a combination of therapeutically effective amounts of one or more MMP inhibitors.

A more preferred therapy for the treatment of fallopian tube cancer is a combination of therapeutically effective amounts of one or more MMP inhibitors in combination with the following of antineoplastic agents: alkylating agents, ifosfamide, cisplatin, carboplatin, taxol, doxorubicin, 5-fluorouracil, methotrexate, mitomycin, hexamethylmelamine, progestins, antiestrogens, prednimustine, dihydroxybusulfan, galactitol, interferon alpha, and interferon gama.

An even more preferred therapy for the treatment of fallopian tube cancer is a combination of therapeutically effective amounts of one or more MMP inhibitors in combination with the following combinations of antineoplastic agents: 1) cisplatin, doxorubicin, cyclophosphamide; 2) hexamthylmelamine, cyclosphamide, doxorubicin, cisplatin; 3) cyclophosphamide, hexamehtylmelamine, 5-flurouracil, cisplatin; 4) melphalan, hexamethylmelamine, cyclophosphamide; 5) melphalan, doxorubicin, cyclophosphamide; 6) cyclophosphamide, cisplatin, carboplatin; 7) cyclophosphamide, doxorubicin, hexamethylmelamine, cisplatin; 8) cyclophosphamide, doxorubicin, hexamethylmelamine, carboplatin; 9) cyclophQsphamide, cisplatin; 10) hexamethylmelamine, doxorubicin, carboplatin; 11) cyclophosphamide, hexamethlmelamine, doxorubicin, cisplatin; 12) carboplatin, cyclophosphamide; 13) cisplatin, cyclophosphamide.

Example 8

Central Nervous System Cancers

Central nervous system cancer accounts for approximately 2% of new cancer cases in the United States. Common intracranial neoplasms include glioma, meninginoma, neurinoma, and adenoma.

A preferred therapy for the treatment of central nervous system cancers is a combination of therapeutically effective amounts of one or more MMP inhibitors.

A preferred therapy for the treatment of malignant glioma is a combination of therapeutically effective amounts of one or more MMP inhibitors in combination with the following combinations of therapies and antineoplastic agents: 1) radiation therapy, BCNU (carmustine); 2) radiation therapy, methyl CCNU (lomustine); 3) radiation therapy, medol; 4) radiation therapy, procarbazine; 5) radiation therapy, BCNU, medrol; 6) hyperfraction radiation therapy, BCNU; 7) radiation therapy, misonidazole, BCNU; 8) radiation therapy, streptozotocin; 9) radiation therapy, BCNU, procarbazine; 10) radiation therapy, BCNU, hydroxyurea, procarbazine, VM-26; 11) radiation therapy, BNCU, 5-flourouacil; 12) radiation therapy, Methyl CCNU, dacarbazine; 13) radiation therapy, misonidazole, BCNU; 14) diaziquone; 15) radiation therapy, PCNU; 16) procarbazine (matulane), CCNU, vincristine. A preferred dose of radiation therapy is about 5,500 to about 6,000 cGY. Preferred radiosensitizers include misonidazole, intra-arterial Budr and intravenous iododeoxyuridine (IUdR). It is also contemplated that radiosurgery may be used in combinations with antiangiogenesis agents.

Example 9

Additional examples of combinations are listed in Table No 17, below.

TABLE 17

| Combination therapies | | |
|---|---|---|
| MMP Inhibitor | Antineoplastic Agent | Indication |
| Compound M1 | Anastrozole | Breast |
| Compound M1 | Capecitabine | Breast |
| Compound M1 | Docetaxel | Breast |
| Compound M1 | Gemcitabine | Breast, Pancreas |
| Compound M1 | Letrozole | Breast |
| Compound M1 | Megestrol | Breast |
| Compound M1 | Paclitaxel | Breast |
| Compound M1 | Tamoxifen | Breast |
| Compound M1 | Toremifene | Breast |
| Compound M1 | Vinorelbine | Breast, Lung |
| Compound M1 | Topotecan | Lung |
| Compound M1 | Etoposide | Lung |
| Compound M1 | Fluorouracil | Colon |
| Compound M1 | Irinotecan (CPT-11) | Colon, Bladder |
| Compound M1 | Retinoids | Colon |
| Compound M1 | DFMO | Colon |
| Compound M1 | Ursodeoxycholic acid | Colon |
| Compound M1 | calcium carbonate | Colon |
| Compound M1 | selenium | Colon |
| Compound M1 | sulindac sulfone | Colon |
| Compound M1 | Carboplatin | Brain |
| Compound M1 | Goserelin Acetate | Prostate |
| Compound M1 | Cisplatin | |
| Compound M1 | Ketoconazole | Prostate |
| Compound M2 | Anastrozole | Breast |
| Compound M2 | Capecitabine | Breast |

TABLE 17-continued

Combination therapies

| MMP Inhibitor | Antineoplastic Agent | Indication |
|---|---|---|
| Compound M2 | Docetaxel | Breast |
| Compound M2 | Gemcitabine | Breast, Pancreas |
| Compound M2 | Letrozole | Breast |
| Compound M2 | Megestrol | Breast |
| Compound M2 | Paclitaxel | Breast |
| Compound M2 | Tamoxifen | Breast |
| Compound M2 | Toremifene | Breast |
| Compound M2 | Vinorelbine | Breast, Lung |
| Compound M2 | Topotecan | Lung |
| Compound M2 | Etoposide | Lung |
| Compound M2 | Fluorouracil | Colon |
| Compound M2 | Irinotecan (CPT-11) | Colon, Bladder |
| Compound M2 | Retinoids | Colon |
| Compound M2 | DFMO | Colon |
| Compound M2 | Ursodeoxycholic acid | Colon |
| Compound M2 | calcium carbonate | Colon |
| Compound M2 | selenium | Colon |
| Compound M2 | sulindac sulfone | Colon |
| Compound M2 | Carboplatin | Brain |
| Compound M2 | Goserelin Acetate | Prostate |
| Compound M2 | Cisplatin | |
| Compound M2 | Ketoconazole | Prostate |
| Compound M3 | Anastrozole | Breast |
| Compound M3 | Capecitabine | Breast |
| Compound M3 | Docetaxel | Breast |
| Compound M3 | Gemcitabine | Breast, Pancreas |
| Compound M3 | Letrozole | Breast |
| Compound M3 | Megestrol | Breast |
| Compound M3 | Paclitaxel | Breast |
| Compound M3 | Tamoxifen | Breast |
| Compound M3 | Toremifene | Breast |
| Compound M3 | Vinorelbine | Breast, Lung |
| Compound M3 | Topotecan | Lung |
| Compound M3 | Etoposide | Lung |
| Compound M3 | Fluorouracil | Colon |
| Compound M3 | Irinotecan (CPT-11) | Colon, Bladder |
| Compound M3 | Retinoids | Colon |
| Compound M3 | DFMO | Colon |
| Compound M3 | Ursodeoxycholic acid | Colon |
| Compound M3 | calcium carbonate | Colon |
| Compound M3 | selenium | Colon |
| Compound M3 | sulindac sulfone | Colon |
| Compound M3 | Carboplatin | Brain |
| Compound M3 | Goserelin Acetate | Prostate |
| Compound M3 | Cisplatin | |
| Compound M3 | Ketoconazole | Prostate |
| Compound M4 | Anastrozole | Breast |
| Compound M4 | Capecitabine | Breast |
| Compound M4 | Docetaxel | Breast |
| Compound M4 | Gemcitabine | Breast, Pancreas |
| Compound M4 | Letrozole | Breast |
| Compound M4 | Megestrol | Breast |
| Compound M4 | Paclitaxel | Breast |
| Compound M4 | Tamoxifen | Breast |
| Compound M4 | Toremifene | Breast |
| Compound M4 | Vinorelbine | Breast, Lung |
| Compound M4 | Topotecan | Lung |
| Compound M4 | Etoposide | Lung |
| Compound M4 | Fluorouracil | Colon |
| Compound M4 | Irinotecan (CPT-11) | Colon, Bladder |
| Compound M4 | Retinoids | Colon |
| Compound M4 | DFMO | Colon |
| Compound M4 | Ursodeoxycholic acid | Colon |
| Compound M4 | calcium carbonate | Colon |
| Compound M4 | selenium | Colon |
| Compound M4 | sulindac sulfone | Colon |
| Compound M4 | Carboplatin | Brain |
| Compound M4 | Goserelin Acetate | Prostate |
| Compound M4 | Cisplatin | |
| Compound M4 | Ketoconazole | Prostate |
| Compound M5 | Anastrozole | Breast |
| Compound M5 | Capecitabine | Breast |
| Compound M5 | Docetaxel | Breast |
| Compound M5 | Gemcitabine | Breast, Pancreas |
| Compound M5 | Letrozole | Breast |
| Compound M5 | Megestrol | Breast |
| Compound M5 | Paclitaxel | Breast |
| Compound M5 | Tamoxifen | Breast |
| Compound M5 | Toremifene | Breast |
| Compound M5 | Vinorelbine | Breast, Lung |
| Compound M5 | Topotecan | Lung |
| Compound M5 | Etoposide | Lung |
| Compound M5 | Fluorouracil | Colon |
| Compound M5 | Irinotecan (CPT-11) | Colon, Bladder |
| Compound M5 | Retinoids | Colon |
| Compound M5 | DFMO | Colon |
| Compound M5 | Ursodeoxycholic acid | Colon |
| Compound M5 | calcium carbonate | Colon |
| Compound M5 | selenium | Colon |
| Compound M5 | sulindac sulfone | Colon |
| Compound M5 | Carboplatin | Brain |
| Compound M5 | Goserelin Acetate | Prostate |
| Compound M5 | Cisplatin | |
| Compound M5 | Ketoconazole | Prostate |
| Compound M7 | Anastrozole | Breast |
| Compound M7 | Capecitabine | Breast |
| Compound M7 | Docetaxel | Breast |
| Compound M7 | Gemcitabine | Breast, Pancreas |
| Compound M7 | Letrozole | Breast |
| Compound M7 | Megestrol | Breast |
| Compound M7 | Paclitaxel | Breast |
| Compound M7 | Tamoxifen | Breast |
| Compound M7 | Toremifene | Breast |
| Compound M7 | Vinorelbine | Breast, Lung |
| Compound M7 | Topotecan | Lung |
| Compound M7 | Etoposide | Lung |
| Compound M7 | Fluorouracil | Colon |
| Compound M7 | Irinotecan (CPT-11) | Colon, Bladder |
| Compound M7 | Retinoids | Colon |
| Compound M7 | DFMO | Colon |
| Compound M7 | Ursodeoxycholic acid | Colon |
| Compound M7 | calcium carbonate | Colon |
| Compound M7 | selenium | Colon |
| Compound M7 | sulindac sulfone | Colon |
| Compound M7 | Carboplatin | Brain |
| Compound M7 | Goserelin Acetate | Prostate |
| Compound M7 | Cisplatin | |
| Compound M7 | Ketoconazole | Prostate |
| Marimastat | Anastrozole | Breast |
| Marimastat | Capecitabine | Breast |
| Marimastat | Docetaxel | Breast |
| Marimastat | Gemcitabine | Breast, Pancreas |
| Marimastat | Letrozole | Breast |
| Marimastat | Megestrol | Breast |
| Marimastat | Paclitaxel | Breast |
| Marimastat | Tamoxifen | Breast |
| Marimastat | Toremifene | Breast |

TABLE 17-continued

Combination therapies

| MMP Inhibitor | Antineoplastic Agent | Indication |
|---|---|---|
| Marimastat | Vinorelbine | Breast, Lung |
| Marimastat | Topotecan | Lung |
| Marimastat | Etoposide | Lung |
| Marimastat | Fluorouracil | Colon |
| Marimastat | Irinotecan (CPT-11) | Colon, Bladder |
| Marimastat | Retinoids | Colon |
| Marimastat | DFMO | Colon |
| Marimastat | Ursodeoxycholic acid | Colon |
| Marimastat | calcium carbonate | Colon |
| Marimastat | selenium | Colon |
| Marimastat | sulindac sulfone | Colon |
| Marimastat | Carboplatin | Brain |
| Marimastat | Goserelin Acetate | Prostate |
| Marimastat | Cisplatin | |
| Marimastat | Ketoconazole | Prostate |
| Bay-12-9566 | Anastrozole | Breast |
| Bay-12-9566 | Capecitabine | Breast |
| Bay-12-9566 | Docetaxel | Breast |
| Bay-12-9566 | Gemcitabine | Breast, Pancreas |
| Bay-12-9566 | Letrozole | Breast |
| Bay-12-9566 | Megestrol | Breast |
| Bay-12-9566 | Paclitaxel | Breast |
| Bay-12-9566 | Tamoxifen | Breast |
| Bay-12-9566 | Toremifene | Breast |
| Bay-12-9566 | Vinorelbine | Breast, Lung |
| Bay-12-9566 | Topotecan | Lung |
| Bay-12-9566 | Etoposide | Lung |
| Bay-12-9566 | Fluorouracil | Colon |
| Bay-12-9566 | Irinotecan (CPT-11) | Colon, Bladder |
| Bay-12-9566 | Retinoids | Colon |
| Bay-12-9566 | DFMO | Colon |
| Bay-12-9566 | Ursodeoxycholic acid | Colon |
| Bay-12-9566 | calcium carbonate | Colon |
| Bay-12-9566 | selenium | Colon |
| Bay-12-9566 | sulindac sulfone | Colon |
| Bay-12-9566 | Carboplatin | Brain |
| Bay-12-9566 | Goserelin Acetate | Prostate |
| Bay-12-9566 | Cisplatin | |
| Bay-12-9566 | Ketoconazole | Prostate |
| AG-3340 | Anastrozole | Breast |
| AG-3340 | Capecitabine | Breast |
| AG-3340 | Docetaxel | Breast |
| AG-3340 | Gemcitabine | Breast, Pancreas |
| AG-3340 | Letrozole | Breast |
| AG-3340 | Megestrol | Breast |
| AG-3340 | Paclitaxel | Breast |
| AG-3340 | Tamoxifen | Breast |
| AG-3340 | Toremifene | Breast |
| AG-3340 | Vinorelbine | Breast, Lung |
| AG-3340 | Topotecan | Lung |
| AG-3340 | Etoposide | Lung |
| AG-3340 | Fluorouracil | Colon |
| AG-3340 | Irinotecan (CPT-11) | Colon, Bladder |
| AG-3340 | Retinoids | Colon |
| AG-3340 | DFMO | Colon |
| AG-3340 | Ursodeoxycholic acid | Colon |
| AG-3340 | calcium carbonate | Colon |
| AG-3340 | selenium | Colon |
| AG-3340 | sulindac sulfone | Colon |
| AG-3340 | Carboplatin | Brain |
| AG-3340 | Goserelin Acetate | Prostate |
| AG-3340 | Cisplatin | |
| AG-3340 | Ketoconazole | Prostate |
| Metastat | Anastrozole | Breast |
| Metastat | Capecitabine | Breast |
| Metastat | Docetaxel | Breast |
| Metastat | Gemcitabine | Breast, Pancreas |
| Metastat | Letrozole | Breast |
| Metastat | Megestrol | Breast |
| Metastat | Paclitaxel | Breast |
| Metastat | Tamoxifen | Breast |
| Metastat | Toremifene | Breast |
| Metastat | Vinorelbine | Breast, Lung |
| Metastat | Topotecan | Lung |
| Metastat | Etoposide | Lung |
| Metastat | Fluorouracil | Colon |
| Metastat | Irinotecan (CPT-11) | Colon, Bladder |
| Metastat | Retinoids | Colon |
| Metastat | DFMO | Colon |
| Metastat | Ursodeoxycholic acid | Colon |
| Metastat | calcium carbonate | Colon |
| Metastat | selenium | Colon |
| Metastat | sulindac sulfone | Colon |
| Metastat | Carboplatin | Brain |
| Metastat | Goserelin Acetate | Prostate |
| Metastat | Cisplatin | |
| Metastat | Ketoconazole | Prostate |
| D-2163 | Anastrozole | Breast |
| D-2163 | Capecitabine | Breast |
| D-2163 | Docetaxel | Breast |
| D-2163 | Gemcitabine | Breast, Pancreas |
| D-2163 | Letrozole | Breast |
| D-2163 | Megestrol | Breast |
| D-2163 | Paclitaxel | Breast |
| D-2163 | Tamoxifen | Breast |
| D-2163 | Toremifene | Breast |
| D-2163 | Vinorelbine | Breast, Lung |
| D-2163 | Topotecan | Lung |
| D-2163 | Etoposide | Lung |
| D-2163 | Fluorouracil | Colon |
| D-2163 | Irinotecan (CPT-11) | Colon, Bladder |
| D-2163 | Retinoids | Colon |
| D-2163 | DFMO | Colon |
| D-2163 | Ursodeoxycholic acid | Colon |
| D-2163 | calcium carbonate | Colon |
| D-2163 | selenium | Colon |
| D-2163 | sulindac sulfone | Colon |
| D-2163 | Carboplatin | Brain |
| D-2163 | Goserelin Acetate | Prostate |
| D-2163 | Cisplatin | |
| D-2163 | Ketoconazole | Prostate |

Additional examples of combinations are listed in Table No 18, below.

TABLE 18

Additional combination therapies

| MMP Inhibitor | Antineoplastic Agents | Indication |
|---|---|---|
| Compound M1 | Doxorubicin and Cyclophosphamide | Breast |

TABLE 18-continued

Additional combination therapies

| MMP Inhibitor | Antineoplastic Agents | Indication |
|---|---|---|
| Compound M1 | Cyclophosphamide, Doxorubicin, and Fluorouracil | Breast |
| Compound M1 | Cyclophosphamide, Fluorouracil and Mitoxantrone | Breast |
| Compound M1 | Mitoxantrone, Flourouracil and Leucovorin | Breast |
| Compound M1 | Vinblastine, Doxorubicin, Thiotepa, and Fluoxymestrone | Breast |
| Compound M1 | Cyclophosphamide, Methotrexate Fluorouracil | Breast |
| Compound M1 | Doxorubicin, Cyclophosphamide, Methotrexate, Fluorouracil | Breast |
| Compound M1 | Vinblastine, Doxorubicin, Thiotepa, Fluoxymesterone | Breast |
| Compound M1 | Fluorouracil, Levamisole | Colon |
| Compound M1 | Leucovorin, Fluorouracil | Colon |
| Compound M1 | Cyclophosphamide, Doxorubicin, Etoposide | Lung |
| Compound M1 | Cyclophosphamide, Doxorubicin, Vincristine | Lung |
| Compound M1 | Etoposide, Carboplatin | Lung |
| Compound M1 | Etoposide, Cisplatin | Lung |
| Compound M1 | Paclitaxel, Carboplatin | Lung |
| Compound M1 | Gemcitabine, Cisplatin | Lung |
| Compound M1 | Paclitaxel, Cisplatin | Lung |
| Compound M2 | Doxorubicin and Cyclophosphamide | Breast |
| Compound M2 | Cyclophosphamide, Doxorubicin, and Fluorouracil | Breast |
| Compound M2 | Cyclophosphamide, Fluorouracil and Mitoxantrone | Breast |
| Compound M2 | Mitoxantrone, Flourouracil and Leucovorin | Breast |
| Compound M2 | Vinblastine, Doxorubicin, Thiotepa, and Fluoxymestrone | Breast |
| Compound M2 | Cyclophosphamide, Methotrexate, Fluorouracil | Breast |
| Compound M2 | Doxorubicin, Cyclophosphamide, Methotrexate, Fluorouracil | Breast |
| Compound M2 | Vinblastine, Doxorubicin, Thiotepa, Fluoxymesterone | Breast |
| Compound M2 | Fluorouracil, Levamisole | Colon |
| Compound M2 | Leucovorin, Fluorouracil | Colon |
| Compound M2 | Cyclophosphamide, Doxorubicin, Etoposide | Lung |
| Compound M2 | Cyclophosphamide, Doxorubicin, Vincristine | Lung |
| Compound M2 | Etoposide, Carboplatin | Lung |
| Compound M2 | Etoposide, Cisplatin | Lung |
| Compound M2 | Paclitaxel, Carboplatin | Lung |
| Compound M2 | Gemcitabine, Cisplatin | Lung |
| Compound M2 | Paclitaxel, Cisplatin | Lung |
| Compound M3 | Doxorubicin and Cyclophosphamide | Breast |
| Compound M3 | Cyclophosphamide, Doxorubicin, and Fluorouracil | Breast |
| Compound M3 | Cyclophosphamide, Fluorouracil and Mitoxantrone | Breast |
| Compound M3 | Mitoxantrone, Flourouracil and Leucovorin | Breast |
| Compound M3 | Vinblastine, Doxorubicin, Thiotepa, and Fluoxymestrone | Breast |
| Compound M3 | Cyclophosphamide, Methotrexate, Fluorouracil | Breast |
| Compound M3 | Doxorubicin, Cyclophosphamide, Methotrexate, Fluorouracil | Breast |
| Compound M3 | Vinblastine, Doxorubicin, Thiotepa, Fluoxymesterone | Breast |
| Compound M3 | Fluorouracil, Levamisole | Colon |
| Compound M3 | Leucovorin, Fluorouracil | Colon |
| Compound M3 | Cyclophosphamide, Doxorubicin, Etoposide | Lung |
| Compound M3 | Cyclophosphamide, Doxorubicin, Vincristine | Lung |
| Compound M3 | Etoposide, Carboplatin | Lung |
| Compound M3 | Etoposide, Cisplatin | Lung |
| Compound M3 | Paclitaxel, Carboplatin | Lung |
| Compound M3 | Gemcitabine, Cisplatin | Lung |
| Compound M3 | Paclitaxel, Cisplatin | Lung |
| Compound M4 | Doxorubicin and Cyclophosphamide | Breast |
| Compound M4 | Cyclophosphamide, Doxorubicin, and Fluorouracil | Breast |
| Compound M4 | Cyclophosphamide, Fluorouracil and Mitoxantrone | Breast |
| Compound M4 | Mitoxantrone, Flourouracil and Leucovorin | Breast |
| Compound M4 | Vinblastine, Doxorubicin, Thiotepa, and Fluoxymestrone | Breast |
| Compound M4 | Cyclophosphamide, Methotrexate, Fluorouracil | Breast |
| Compound M4 | Doxorubicin, Cyclophosphamide, Methotrexate, Fluorouracil | Breast |
| Compound M4 | Vinblastine, Doxorubicin, Thiotepa, Fluoxymesterone | Breast |
| Compound M4 | Fluorouracil, Levamisole | Colon |
| Compound M4 | Leucovorin, Fluorouracil | Colon |
| Compound M4 | Cyclophosphamide, Doxorubicin, Etoposide | Lung |
| Compound M4 | Cyclophosphamide, Doxorubicin, Vincristine | Lung |
| Compound M4 | Etoposide, Carboplatin | Lung |
| Compound M4 | Etoposide, Cisplatin | Lung |
| Compound M4 | Paclitaxel, Carboplatin | Lung |
| Compound M4 | Gemcitabine, Cisplatin | Lung |
| Compound M4 | Paclitaxel, Cisplatin | Lung |
| Compound M5 | Doxorubicin and Cyclophosphamide | Breast |
| Compound M5 | Cyclophosphamide, Doxorubicin, and Fluorouracil | Breast |
| Compound M5 | Cyclophosphamide, Fluorouracil and Mitoxantrone | Breast |
| Compound M5 | Mitoxantrone, Flourouracil and Leucovorin | Breast |
| Compound M5 | Vinblastine, Doxorubicin, Thiotepa, and Fluoxymestrone | Breast |

TABLE 18-continued

Additional combination therapies

| MMP Inhibitor | Antineoplastic Agents | Indication |
|---|---|---|
| Compound M5 | Cyclophosphamide, Methotrexate, Fluorouracil | Breast |
| Compound M5 | Doxorubicin, Cyclophosphamide, Methotrexate, Fluorouracil | Breast |
| Compound M5 | Vinblastine, Doxorubicin, Thiotepa, Fluoxymesterone | Breast |
| Compound M5 | Fluorouracil, Levamisole | Colon |
| Compound M5 | Leucovorin, Fluorouracil | Colon |
| Compound M5 | Cyclophosphamide, Doxorubicin, Etoposide | Lung |
| Compound M5 | Cyclophosphamide, Doxorubicin, Vincristine | Lung |
| Compound M5 | Etoposide, Carboplatin | Lung |
| Compound M5 | Etoposide, Cisplatin | Lung |
| Compound M5 | Paclitaxel, Carboplatin | Lung |
| Compound M5 | Gemcitabine, Cisplatin | Lung |
| Compound M5 | Paclitaxel, Cisplatin | Lung |
| Compound M7 | Doxorubicin and Cyclophosphamide | Breast |
| Compound M7 | Cyclophosphamide, Doxorubicin, and Fluorouracil | Breast |
| Compound M7 | Cyclophosphamide, Fluorouracil and Mitoxantrone | Breast |
| Compound M7 | Mitoxantrone, Flourouracil and Leucovorin | Breast |
| Compound M7 | Vinblastine, Doxorubicin, Thiotepa, and Fluoxymestrone | Breast |
| Compound M7 | Cyclophosphamide, Methotrexate, Fluorouracil | Breast |
| Compound M7 | Doxorubicin, Cyclophosphamide, Methotrexate, Fluorouracil | Breast |
| Compound M7 | Vinblastine, Doxorubicin, Thiotepa, Fluoxymesterone | Breast |
| Compound M7 | Fluorouracil, Levamisole | Colon |
| Compound M7 | Leucovorin, Fluorouracil | Colon |
| Compound M7 | Cyclophosphamide, Doxorubicin, Etoposide | Lung |
| Compound M7 | Cyclophosphamide, Doxorubicin, Vincristine | Lung |
| Compound M7 | Etoposide, Carboplatin | Lung |
| Compound M7 | Etoposide, Cisplatin | Lung |
| Compound M7 | Paclitaxel, Carboplatin | Lung |
| Compound M7 | Gemcitabine, Cisplatin | Lung |
| Compound M7 | Paclitaxel, Cisplatin | Lung |
| Bay-12-9566 | Doxorubicin and Cyclophosphamide | Breast |
| Bay-12-9566 | Cyclophosphamide, Doxorubicin, and Fluorouracil | Breast |
| Bay-12-9566 | Cyclophosphamide, Fluorouracil and Mitoxantrone | Breast |
| Bay-12-9566 | Mitoxantrone, Flourouracil and Leucovorin | Breast |
| Bay-12-9566 | Vinblastine, Doxorubicin, Thiotepa, and Fluoxymestrone | Breast |
| Bay-12-9566 | Cyclophosphamide, Methotrexate, Fluorouracil | Breast |
| Bay-12-9566 | Doxorubicin, Cyclophosphamide, Methotrexate, Fluorouracil | Breast |
| Bay-12-9566 | Vinblastine, Doxorubicin, Thiotepa, Fluoxymesterone | Breast |
| Bay-12-9566 | Fluorouracil, Levamisole | Colon |
| Bay-12-9566 | Leucovorin, Fluorouracil | Colon |
| Bay-12-9566 | Cyclophosphamide, Doxorubicin, Etoposide | Lung |
| Bay-12-9566 | Cyclophosphamide, Doxorubicin, Vincristine | Lung |
| Bay-12-9566 | Etoposide, Carboplatin | Lung |
| Bay-12-9566 | Etoposide, Cisplatin | Lung |
| Bay-12-9566 | Paclitaxel, Carboplatin | Lung |
| Bay-12-9566 | Gemcitabine, Cisplatin | Lung |
| Bay-12-9566 | Paclitaxel, Cisplatin | Lung |
| Metastat | Doxorubicin and Cyclophosphamide | Breast |
| Metastat | Cyclophosphamide, Doxorubicin, and Fluorouracil | Breast |
| Metastat | Cyclophosphamide, Fluorouracil and Mitoxantrone | Breast |
| Metastat | Mitoxantrone, Flourouracil and Leucovorin | Breast |
| Metastat | Vinblastine, Doxorubicin, Thiotepa, and Fluoxymestrone | Breast |
| Metastat | Cyclophosphamide, Methotrexate, Fluorouracil | Breast |
| Metastat | Doxorubicin, Cyclophosphamide, Methotrexate, Fluorouracil | Breast |
| Metastat | Vinblastine, Doxorubicin, Thiotepa, Fluoxymesterone | Breast |
| Metastat | Fluorouracil, Levamisole | Colon |
| Metastat | Leucovorin, Fluorouracil | Colon |
| Metastat | Cyclophosphamide, Doxorubicin, Etoposide | Lung |
| Metastat | Cyclophosphamide, Doxorubicin, Vincristine | Lung |
| Metastat | Etoposide, Carboplatin | Lung |
| Metastat | Etoposide, Cisplatin | Lung |
| Metastat | Paclitaxel, Carboplatin | Lung |
| Metastat | Gemcitabine, Cisplatin | Lung |
| Metastat | Paclitaxel, Cisplatin | Lung |
| D-2163 | Doxorubicin and Cyclophosphamide | Breast |
| D-2163 | Cyclophosphamide, Doxorubicin, and Fluorouracil | Breast |
| D-2163 | Cyclophosphamide, Fluorouracil and Mitoxantrone | Breast |
| D-2163 | Mitoxantrone, Flourouracil and Leucovorin | Breast |
| D-2163 | Vinblastine, Doxorubicin, Thiotepa, and Fluoxymestrone | Breast |
| D-2163 | Cyclophosphamide, Methotrexate, Fluorouracil | Breast |
| D-2163 | Doxorubicin, Cyclophosphamide, Methotrexate, Fluorouracil | Breast |
| D-2163 | Vinblastine, Doxorubicin, Thiotepa, Fluoxymesterone | Breast |
| D-2163 | Fluorouracil, Levamisole | Colon |
| D-2163 | Leucovorin, Fluorouracil | Colon |
| D-2163 | Cyclophosphamide, Doxorubicin, Etoposide | Lung |

TABLE 18-continued

Additional combination therapies

| MMP Inhibitor | Antineoplastic Agents | Indication |
|---|---|---|
| D-2163 | Cyclophosphamide, Doxorubicin, Vincristine | Lung |
| D-2163 | Etoposide, Carboplatin | Lung |
| D-2163 | Etoposide, Cisplatin | Lung |
| D-2163 | Paclitaxel, Carboplatin | Lung |
| D-2163 | Gemcitabine, Cisplatin | Lung |
| D-2163 | Paclitaxel, Cisplatin | Lung |
| D-1927 | Doxorubicin and Cyclophosphamide | Breast |
| D-1927 | Cyclophosphamide, Doxorubicin, and Fluorouracil | Breast |
| D-1927 | Cyclophosphamide, Fluorouracil and Mitoxantrone | Breast |
| D-1927 | Mitoxantrone, Flourouracil and Leucovorin | Breast |
| D-1927 | Vinblastine, Doxorubicin, Thiotepa, and Fluoxymestrone | Breast |
| D-1927 | Cyclophosphamide, Methotrexate, Fluorouracil | Breast |
| D-1927 | Doxorubicin, Cyclophosphamide, Methotrexate, Fluorouracil | Breast |
| D-1927 | Vinblastine, Doxorubicin, Thiotepa, Fluoxymesterone | Breast |
| D-1927 | Fluorouracil, Levamisole | Colon |
| D-1927 | Leucovorin, Fluorouracil | Colon |
| D-1927 | Cyclophosphamide, Doxorubicin, Etoposide | Lung |
| D-1927 | Cyclophosphamide, Doxorubicin, Vincristine | Lung |
| D-1927 | Etoposide, Carboplatin | Lung |
| D-1927 | Etoposide, Cisplatin | Lung |
| D-1927 | Paclitaxel, Carboplatin | Lung |
| D-1927 | Gemcitabine, Cisplatin | Lung |
| D-1927 | Paclitaxel, Cisplatin | Lung |

Biological Evaluation

MMP Inhibitors

1. Pancreatic Cell (PC-3) Model:

In this study, the test groups were a vehicle control, Compound M14, Compound M14 with cisplatin and cisplatin alone with n=10 for each group. The tumors were measured with a caliper and the volume calculated using the formula for the volume of an elipsoid. The cisplatin dose was 10 mpk administered by the intraperitonal route on day 8 post injecion of tumor cells Compound M14, 50 mpk, was first administered about 6:00 pm the evening of the same day that the tumor cells were injected in the morning. The same dose of Compound M14 was administered bid for each following day. Tumor volume ($mm^3$) was measured on day 25. The data below clearly show an improved response with the combination of the MMP inhibitor and cisplatin.

PC3 Model MMP Inhibitor
Combination Study Results

| Agent Administered PC3 Model | Tumor Volume at Day 25 ($mm^3$) |
|---|---|
| vehicle | 860 |
| cisplatin | 630 |
| Compound M14 | 480 |
| Compound M14 with cisplatin | 110 |

2. Breast Tumor Model:

This study was carried out essentially as PC-3 model. MX-1 breast tumor pieces were implanted (with a trocar) into nude mice with n=10 per group. Dosing with Compound M14 (10 mpk or 50 mpk, PO bid) was initiated when the tumors reached a size of 60–120 mg. Dosing was continued for 26 days. Taxol was administered at a dose of 9 mpk for the first five days following the start of dosing by the interperitonal route. The tumors were measured using a caliper and the volume calculated using the formula for the volume of an elipsoid. The results tabulated below clearly show an improved response with combination therapy. An improved response is obtained with lower doses Compound M14.

MX-1 Model MMP Inhibitor
Combination Study Results

| Agent Administered | Tumor Volume at Day 25 ($mm^3$) |
|---|---|
| vehicle | 1920 |
| taxol | 1280 |
| Compound M14 @ 10 mpk | 960 |
| Compound M14 @ 50 mpk | 1260 |
| Compound M14 @ 50 mpk + taxol @ 9 mpk | 480 |
| Compound M14 @ 10 mpk + taxol @ 9 mpk | 240 |

3. MX-1 Adjuvant Model:

Mice were implanted with MX-1 tumors and allowed to grow to 50–100 mm3. The animals were dosed with cyclophosphamide (100 or 80 mpk). This was considered Day 1. Two weeks later the animals were pair matched after tumor regression and dosing BID with the MMPI was begun until the end of the experiment. Tumors were measured weekly. The endpoint for the study was a final tumor size of 1.5 g.

| | Cyclophosphamide Dose (mpk) | MMPI | MMPI Dose (mpk) | MDS | sem |
|---|---|---|---|---|---|
| saline | | | | 23.9 | 1.3 |
| cyclophosphamide | 100 | | | 39.5 | 1.2 |
| cyclophosphamide | 80 | | | 37.2 | 1.5 |
| cyclophosphamide | 100 | Compound M14 | 200 | 52.7 | 2.9 |
| cyclophosphamide | 100 | Compound M14 | 50 | 43.7 | 1.6 |
| cyclophosphamide | 0 | Compound M14 | 200 | 53.9 | 2.9 |
| cyclophosphamide | 80 | Compound M14 | 50 | 44.2 | 1.8 |

MDS=mean days to tumor weight of 1.5 g

4. MX-1 Breast Tumor with Taxol:

Mice were implanted with MX-1 tumors and allowed to grow to 50–100 mg. The animals were pair matched and this was considered Day 1. Treatment with MMPI was begun BID on Day 1 until the end of the experiment. Taxol was injected IP (15 or 9 mpk) QD for 5 days (days 1–5). Tumors were measured weekly until an endpoint of 1.5 g was reached.

| | Taxol Dose (mpk) | MMPI | MMPI Dose (mpk) | MDS | sem |
|---|---|---|---|---|---|
| vehicle | | | | 25.3 | 0.8 |
| mmpi | | Compound M14 | 100 | 32.2 | 2.8 |
| mmpi | | Compound M14 | 20 | 34.7 | 3 |
| taxol + mmpi | 18 | Compound M14 | | 56 | 11 |
| taxol + mmpi | 9 | Compound M14 | | 30.1 | 1.8 |
| taxol + mmpi | 18 | Compound M14 | 100 | 61 | |
| taxol + mmpi | 9 | Compound M14 | 100 | 46.7 | 3.7 |
| taxol + mmpi | 18 | Compound M14 | 20 | 59.3 | 7 |
| taxol + mmpi | 9 | Compound M14 | 20 | 39.3 | 1.9 |

MDS = 1.5 g

5. SK-mes Tumor with Taxol

Mice were implanted with SK-mes tumors and allowed to grow to 50–100 mg. The animals were pair matched and this was considered Day 1. Treatment with MMPI was begun BID on Day 1 until the end of the experiment. Taxol was injected IP (18 or 9 mpk) QD for 5 days (days 1–5). Tumors were measured weekly until an endpoint of 1.0 g was reached.

| | Taxol Dose (mpk) | MMPI | MMPI Dose (mpk) | MDS | sem |
|---|---|---|---|---|---|
| vehicle | | | | 21.2 | 2.1 |
| mmpi | | Compound M14 | 100 | 24.7 | 1.6 |
| mmpi | | Compound M14 | 20 | 18 | 1.1 |
| taxol | 18 | | | 31.5 | 2.4 |
| taxol | 9 | | | 26.1 | 2.3 |
| taxol + mmpi | 18 | Compound M14 | 100 | 43 | 4 |
| taxol + mmpi | 9 | Compound M14 | 100 | 34.8 | 1.9 |
| taxol + mmpi | 18 | Compound M14 | 20 | 39.5 | 3.6 |
| taxol + mmpi | 9 | Compound M14 | 20 | 34.1 | 5.7 |

MDS = 1.0 g

6. HT-29 Tumor with Irinotecan

Mice were implanted with HT-29 tumors and allowed to grow to 50–100 mg. The animals were pair matched and this was considered Day 1. Treatment with MMPI was begun BID on Day 1 until the end of the experiment. Irinotecan was injected IP (100 or 50 mpk) QD for 5 days (days 1–5). Tumors were measured weekly until an endpoint of 1.0 g was reached.

| | Irinotecan Dose (mpk) | MMPI | MMPI Dose (mpk) | MDS | SEM |
|---|---|---|---|---|---|
| vehicle | | | | 36.4 | 4.3 |
| mmpi | | Compound M14 | 100 | 37.9 | 5.0 |
| mmpi | | Compound M14 | 20 | 36 | 4.2 |
| Irinotecan | 100 | | | 36.7 | 2.6 |
| Irinotecan | 50 | | | 38.1 | 3.0 |
| Irinotecan + mmpi | 100 | Compound M14 | 100 | 51.4 | 4.4 |
| Irinotecan + mmpi | 50 | Compound M14 | 100 | 44.4 | 4.0 |
| Irinotecan + mmpi | 100 | Compound M14 | 20 | 40.6 | 4.7 |
| Irinotecan + mmpi | 50 | Compound M14 | 20 | 36.1 | 3.0 |

MDS = 1.0 g

What is claimed is:

1. A combination comprising (a) a matrix metalloproteinase inhibitor and (b) an antineoplastic agent selected from the group consisting of irinotecan, topotecan and combinations thereof, in amounts effective, when used in a combination therapy, for treatment of a neoplasia disorder.

2. The combination of claim 1 wherein the matrix metalloproteinase inhibitor is an inhibitor of gelatinase.

3. The combination of claim 1 wherein the matrix metalloproteinase inhibitor inhibits at least one of MMP-2 and MMP-9.

4. The combination of claim 1 wherein the matrix metalloproteinase inhibitor is a hydroxamate compound.

5. The combination of claim 1 wherein the matrix metalloproteinase inhibitor is selected from the group consisting of marimastat, batimastat, AG-3340, doxycycline and pharmaceutically acceptable salts thereof.

6. A method for treating a neoplasia disorder in a mammal, the method comprising administering to the mammal a therapeutically effective amount of a combination of claim 1 comprising (a) a matrix metalloproteinuse inhibitor and (b) an antineoplastic agent selected from the group consisting of irinotecan, topotecan and combinations thereof.

7. The method of claim 6 wherein the matrix metalloproteinase inhibitor is an inhibitor of gelatinase.

8. The method of claim 6 wherein the matrix metalloproteinase inhibitor inhibits at least one of MMP-2 and MMP-9.

9. The method of claim 6 wherein the matrix metalloproteinase inhibitor is a hydroxamate compound.

10. The method of claim 6 wherein the matrix metalloproteinase inhibitor is selected from the group consisting of marimastat, batimastat, AG-3340, doxycycline and pharmaceutically acceptable salts thereof.

11. The method of claim 6 wherein the combination is administered in a sequential manner.

12. The method of claim 6 wherein the combination is administered in a substantially simultaneous manner.

13. The method of claim 6 wherein the neoplasia disorder is a cancer selected from the group consisting of colorectal cancer, breast cancer, prostate cancer, bladder cancer, ovary cancer, cervical cancer, gastrointestinal cancer, head and neck cancer, and lung cancer.

14. The method of claim 6, further comprising administering to the mammal a therapeutically effective amount of radiation therapy.

* * * * *